United States Patent
Gemba et al.

(10) Patent No.: US 10,149,905 B2
(45) Date of Patent: *Dec. 11, 2018

(54) CHIRAL NUCLEIC ACID ADJUVANT HAVING ANTITUMOR EFFECT AND ANTITUMOR AGENT

(71) Applicants: Shin Nippon Biomedical Laboratories, Ltd., Kagoshima-shi (JP); WAVE LIFE SCIENCES JAPAN, INC., Kagoshima-shi (JP)

(72) Inventors: Takefumi Gemba, Kagoshima (JP); Ryoichi Nagata, Kagoshima (JP); Yusuke Torikai, Kagoshima (JP)

(73) Assignees: SHIN NIPPON BIOMEDICAL LABORATORIES, LTD., Kagoshima-shi (JP); WAVE LIFE SCIENCES JAPAN, INC., Kagoshima-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/111,798

(22) PCT Filed: Jan. 14, 2015

(86) PCT No.: PCT/JP2015/050718
§ 371 (c)(1),
(2) Date: Jul. 14, 2016

(87) PCT Pub. No.: WO2015/108048
PCT Pub. Date: Jul. 23, 2015

(65) Prior Publication Data
US 2016/0331836 A1    Nov. 17, 2016

(30) Foreign Application Priority Data

Jan. 15, 2014   (JP) .................................. 2014-005510

(51) Int. Cl.
*C12N 15/117*    (2010.01)
*A61K 39/39*    (2006.01)
*A61K 31/7088*    (2006.01)
*A61K 39/00*    (2006.01)

(52) U.S. Cl.
CPC .......... *A61K 39/39* (2013.01); *A61K 31/7088* (2013.01); *C12N 15/117* (2013.01); *A61K 2039/55561* (2013.01); *A61K 2039/572* (2013.01); *C12N 2310/17* (2013.01); *C12N 2310/315* (2013.01); *C12N 2310/344* (2013.01); *C12N 2320/31* (2013.01)

(58) Field of Classification Search
CPC ... A61K 39/39; A61K 31/7088; C12N 15/117
See application file for complete search history.

(56) References Cited

U.S. PATENT DOCUMENTS

| | | |
|---|---|---|
| 2,878,264 A | 3/1959 | Lunsford |
| 3,135,766 A | 6/1964 | Gould |
| 3,484,473 A | 12/1969 | Buckman et al. |
| 3,687,808 A | 8/1972 | Merigan et al. |
| 3,745,162 A | 7/1973 | Helsley |
| 4,022,791 A | 5/1977 | Welch, Jr. |
| 4,113,869 A | 9/1978 | Gardner |
| 4,415,732 A | 11/1983 | Caruthers et al. |
| 4,458,066 A | 7/1984 | Caruthers et al. |
| 4,500,707 A | 2/1985 | Caruthers et al. |
| 4,542,142 A | 9/1985 | Martel et al. |
| 4,659,774 A | 4/1987 | Webb et al. |
| 4,663,328 A | 5/1987 | Lafon |
| 4,668,777 A | 5/1987 | Caruthers et al. |
| 4,725,677 A | 2/1988 | Koster et al. |
| 4,735,949 A | 4/1988 | Domagala et al. |
| 4,840,956 A | 6/1989 | Domagala et al. |
| 4,845,205 A | 7/1989 | Huynh Dinh et al. |
| 4,923,901 A | 5/1990 | Koester et al. |

(Continued)

FOREIGN PATENT DOCUMENTS

| | | |
|---|---|---|
| CN | 102675386 A | 9/2012 |
| DE | 1144279 B | 2/1963 |

(Continued)

OTHER PUBLICATIONS

Lee et al. Moelcular Immunology 41, 2004: 955-964.*
Aartsma-Rus, A. et al., Targeted exon skipping as a potential gene correction therapy for Duchenne muscular dystrophy, Neuromuscular Disorders, 12: S71-S77 (2002).
Adams, S.P. et al., Hindered dialkylamino nucleoside phosphite reagents in the synthesis of two DNA 51-mers, Journal of the American Chemical Society, 105(3): 661-663 (1983).
Adarsh, et al., Organelle Specific Targeted Drug Delivery—A Review, International Journal of Research in Pharmaceutical and Biomedical Sciences, 2(3): 895-912 (2011).

(Continued)

*Primary Examiner* — Brian A Whiteman
(74) *Attorney, Agent, or Firm* — Choate, Hall & Stewart LLP; Brenda Herschbach Jerrell; Xiaodong Li

(57) ABSTRACT

Summary
Problem
The purpose of the present invention is to provide: a chiral nucleic acid adjuvant having anti-tumor activity; and an anti-tumor agent.
Solution
The present invention relates to an adjuvant for anti-tumor agent, wherein the adjuvant comprises oligonucleotides which comprise two to four CpG motif each represented by 5'-$X_1$CpG$X_2$-3' and has a length of 14 to 32 nucleotides, wherein a nucleic acid at 3' end side of at least two CpG motifs is connected by phosphorothioate linkage, wherein each nucleic acid at 3' end and 5' end of the oligonucleotide is S type nucleic acid connected by phosphorothioate linkage, and wherein the oligonucleotide comprises at least one nucleic acid without phosphorothioate modification. The present invention relates to an anti-tumor agent containing its adjuvant.

4 Claims, 2 Drawing Sheets

Specification includes a Sequence Listing.

(56) References Cited

U.S. PATENT DOCUMENTS

| | | |
|---|---|---|
| 4,973,679 A | 11/1990 | Caruthers et al. |
| 4,981,957 A | 1/1991 | Lebleu et al. |
| 5,047,524 A | 9/1991 | Andrus et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| 5,141,813 A | 8/1992 | Nelson |
| 5,151,510 A | 9/1992 | Stec et al. |
| 5,175,273 A | 12/1992 | Bischofberger et al. |
| 5,200,553 A | 4/1993 | Nudelman et al. |
| 5,212,295 A | 5/1993 | Cook |
| 5,262,530 A | 11/1993 | Andrus et al. |
| 5,292,875 A | 3/1994 | Stec et al. |
| 5,319,080 A | 6/1994 | Leumann |
| 5,359,044 A | 10/1994 | Cook et al. |
| 5,367,066 A | 11/1994 | Urdea et al. |
| 5,432,272 A | 7/1995 | Benner |
| 5,457,187 A | 10/1995 | Gmeiner et al. |
| 5,457,191 A | 10/1995 | Cook et al. |
| 5,459,255 A | 10/1995 | Cook et al. |
| 5,484,908 A | 1/1996 | Froehler et al. |
| 5,502,177 A | 3/1996 | Matteucci et al. |
| 5,506,212 A | 4/1996 | Hoke et al. |
| 5,512,668 A | 4/1996 | Stec et al. |
| 5,521,302 A | 5/1996 | Cook |
| 5,525,711 A | 6/1996 | Hawkins et al. |
| 5,552,540 A | 9/1996 | Haralambidis |
| 5,576,302 A | 11/1996 | Cook et al. |
| 5,587,361 A | 12/1996 | Cook et al. |
| 5,587,469 A | 12/1996 | Cook et al. |
| 5,594,121 A | 1/1997 | Froehler et al. |
| 5,596,091 A | 1/1997 | Switzer |
| 5,599,797 A | 2/1997 | Cook et al. |
| 5,607,923 A | 3/1997 | Cook et al. |
| 5,614,617 A | 3/1997 | Cook et al. |
| 5,620,963 A | 4/1997 | Cook et al. |
| 5,635,488 A | 6/1997 | Cook et al. |
| 5,643,889 A | 7/1997 | Suhadolnik et al. |
| 5,643,989 A | 7/1997 | Van De Grampel et al. |
| 5,646,267 A | 7/1997 | Stec et al. |
| 5,654,284 A | 8/1997 | Cook et al. |
| 5,661,134 A | 8/1997 | Cook et al. |
| 5,681,940 A | 10/1997 | Wang et al. |
| 5,681,941 A | 10/1997 | Cook et al. |
| 5,708,161 A | 1/1998 | Reese |
| 5,712,378 A | 1/1998 | Wang |
| 5,734,041 A | 3/1998 | Just et al. |
| 5,750,692 A | 5/1998 | Cook et al. |
| 5,795,765 A | 8/1998 | Izu et al. |
| 5,824,503 A | 10/1998 | Kurome et al. |
| 5,846,466 A | 12/1998 | Abe et al. |
| 5,851,840 A | 12/1998 | Sluka et al. |
| 5,852,188 A | 12/1998 | Cook |
| 5,856,465 A | 1/1999 | Stec et al. |
| 5,883,237 A | 3/1999 | Stec et al. |
| 5,898,031 A | 4/1999 | Crooke |
| 5,908,772 A | 6/1999 | Mitta et al. |
| 5,914,396 A | 6/1999 | Cook et al. |
| 5,932,450 A | 8/1999 | Dattagupta et al. |
| 5,936,080 A | 8/1999 | Stec et al. |
| 5,976,855 A | 11/1999 | Svendsen et al. |
| 5,998,602 A | 12/1999 | Torrence et al. |
| 6,004,813 A | 12/1999 | Serlupi-Crescenzi et al. |
| 6,015,886 A | 1/2000 | Dale et al. |
| 6,015,887 A | 1/2000 | Teng |
| 6,017,700 A | 1/2000 | Horn et al. |
| 6,031,092 A | 2/2000 | Just et al. |
| 6,056,973 A | 5/2000 | Allen et al. |
| 6,057,371 A | 5/2000 | Glennon |
| 6,066,500 A | 5/2000 | Bennett et al. |
| 6,080,543 A | 6/2000 | Engel et al. |
| 6,107,094 A | 8/2000 | Crooke |
| 6,124,445 A | 9/2000 | Imbach et al. |
| 6,133,438 A | 10/2000 | Cook et al. |
| 6,140,096 A | 10/2000 | Kofod et al. |
| 6,146,829 A | 11/2000 | Cook et al. |
| 6,147,200 A | 11/2000 | Manoharan et al. |
| 6,159,728 A | 12/2000 | Stockley et al. |
| 6,160,109 A | 12/2000 | Just et al. |
| 6,166,197 A | 12/2000 | Cook et al. |
| 6,172,209 B1 | 1/2001 | Manoharan et al. |
| 6,191,266 B1 | 2/2001 | Wang |
| 6,207,646 B1 | 3/2001 | Krieg et al. |
| 6,214,805 B1 | 4/2001 | Torrence et al. |
| 6,222,025 B1 | 4/2001 | Cook et al. |
| 6,235,887 B1 | 5/2001 | Froehler et al. |
| 6,239,116 B1 | 5/2001 | Krieg et al. |
| 6,239,265 B1 | 5/2001 | Cook |
| 6,242,589 B1 | 6/2001 | Cook et al. |
| 6,248,519 B1 | 6/2001 | Engel et al. |
| 6,265,172 B1 | 7/2001 | St. Clair et al. |
| 6,270,968 B1 | 8/2001 | Dalb.o slashed.ge et al. |
| 6,271,004 B1 | 8/2001 | Warthoe |
| 6,300,069 B1 | 10/2001 | Missel et al. |
| 6,306,627 B1 | 10/2001 | Decker |
| 6,316,024 B1 | 11/2001 | Allen et al. |
| 6,316,626 B1 | 11/2001 | Swayze et al. |
| 6,322,985 B1 | 11/2001 | Kashi et al. |
| 6,326,199 B1 | 12/2001 | Cook et al. |
| 6,339,066 B1 | 1/2002 | Bennett et al. |
| 6,344,356 B1 | 2/2002 | Stemmer |
| 6,369,209 B1 | 4/2002 | Manoharan et al. |
| 6,369,237 B1 | 4/2002 | Verdine et al. |
| 6,380,368 B1 | 4/2002 | Froehler et al. |
| 6,383,808 B1 | 5/2002 | Monia et al. |
| 6,407,223 B1 | 6/2002 | Stec et al. |
| 6,440,739 B1 | 8/2002 | Bennett et al. |
| 6,440,943 B1 | 8/2002 | Cook et al. |
| 6,451,524 B1 | 9/2002 | Ecker |
| 6,455,308 B1 | 9/2002 | Freier |
| 6,468,983 B2 | 10/2002 | Silverman et al. |
| 6,500,945 B2 | 12/2002 | Cook |
| 6,506,594 B1 | 1/2003 | Barany et al. |
| 6,506,894 B1 | 1/2003 | Reese et al. |
| 6,528,262 B1 | 3/2003 | Gilad et al. |
| 6,528,640 B1 | 3/2003 | Beigelman et al. |
| 6,538,126 B1 | 3/2003 | Cho et al. |
| 6,559,279 B1 | 5/2003 | Manoharan et al. |
| 6,562,960 B1 | 5/2003 | Baxter et al. |
| 6,582,936 B1 | 6/2003 | Serafini et al. |
| 6,608,186 B1 | 8/2003 | Miculka et al. |
| 6,610,837 B1 | 8/2003 | Guzaev et al. |
| 6,613,873 B1 | 9/2003 | Buchardt et al. |
| 6,617,438 B1 | 9/2003 | Beigelman et al. |
| 6,632,600 B1 | 10/2003 | Short |
| 6,639,022 B2 | 10/2003 | Michels et al. |
| 6,639,062 B2 | 10/2003 | Manoharan et al. |
| 6,649,750 B1 | 11/2003 | Capaldi et al. |
| 6,682,889 B1 | 1/2004 | Wang et al. |
| 6,699,979 B2 | 3/2004 | Cook |
| 6,737,520 B2 | 5/2004 | Manoharan et al. |
| 6,762,281 B2 | 7/2004 | Manoharan et al. |
| 6,767,739 B2 | 7/2004 | Crooke et al. |
| 6,809,195 B1 | 10/2004 | Sanghvi et al. |
| 6,811,975 B2 | 11/2004 | Cook et al. |
| 6,861,518 B2 | 3/2005 | Just et al. |
| 6,867,294 B1 | 3/2005 | Sanghvi et al. |
| 6,933,146 B2 | 8/2005 | Helliwell et al. |
| 6,933,288 B2 | 8/2005 | Migawa et al. |
| 6,936,432 B2 | 8/2005 | Gopalan et al. |
| 6,943,240 B2 * | 9/2005 | Bauer .................. C07K 14/705 435/320.1 |
| 6,949,520 B1 | 9/2005 | Hartmann et al. |
| 6,977,245 B2 | 12/2005 | Klinman et al. |
| 6,995,259 B1 | 2/2006 | Vargeese et al. |
| 7,015,315 B1 | 3/2006 | Cook et al. |
| 7,018,793 B1 | 3/2006 | Short |
| 7,019,127 B2 | 3/2006 | Reese et al. |
| 7,022,833 B2 | 4/2006 | Reese |
| 7,030,230 B2 | 4/2006 | Ross et al. |
| 7,045,610 B2 | 5/2006 | Dempcy et al. |
| 7,049,122 B2 | 5/2006 | Chang et al. |
| 7,067,497 B2 | 6/2006 | Hanecak et al. |

(56) References Cited

U.S. PATENT DOCUMENTS

| | | |
|---|---|---|
| 7,101,993 B1 | 9/2006 | Cook et al. |
| 7,119,184 B2 | 10/2006 | Manoharan et al. |
| RE39,464 E | 1/2007 | Cook et al. |
| 7,160,920 B2 | 1/2007 | Garvey et al. |
| 7,205,399 B1 | 4/2007 | Vargeese et al. |
| 7,214,491 B2 | 5/2007 | Yadav et al. |
| 7,227,014 B2 | 6/2007 | Crooke et al. |
| 7,259,150 B2 | 8/2007 | Crooke et al. |
| 7,264,932 B2 | 9/2007 | Latham et al. |
| 7,271,156 B2 | 9/2007 | Krieg et al. |
| 7,288,376 B2 | 10/2007 | Sarma et al. |
| 7,303,895 B1 | 12/2007 | O'Regan et al. |
| 7,304,081 B2 | 12/2007 | Yao et al. |
| 7,354,909 B2 | 4/2008 | Klinman et al. |
| 7,381,527 B2 | 6/2008 | Sarma et al. |
| 7,399,845 B2 | 7/2008 | Seth et al. |
| 7,407,943 B2 | 8/2008 | Crooke et al. |
| 7,410,975 B2 | 8/2008 | Lipford et al. |
| 7,414,116 B2 | 8/2008 | Milton et al. |
| 7,425,545 B2 | 9/2008 | Crooke et al. |
| 7,427,672 B2 | 9/2008 | Imanishi et al. |
| 7,432,249 B2 | 10/2008 | Crooke |
| 7,432,250 B2 | 10/2008 | Crooke |
| 7,495,088 B1 | 2/2009 | Brakel et al. |
| 7,501,091 B2 | 3/2009 | Munoz et al. |
| 7,507,808 B2 | 3/2009 | Dobie |
| 7,507,811 B2 | 3/2009 | Khvorova et al. |
| 7,511,131 B2 | 3/2009 | Crooke et al. |
| 7,517,520 B2 | 4/2009 | Manolova et al. |
| 7,534,879 B2 | 5/2009 | van Deutekom |
| 7,537,767 B2 | 5/2009 | Bachmann et al. |
| 7,547,684 B2 | 6/2009 | Seth et al. |
| 7,585,847 B2 | 9/2009 | Bratzler et al. |
| 7,598,031 B2 | 10/2009 | Liew |
| 7,598,227 B2 | 10/2009 | Crooke et al. |
| 7,629,321 B2 | 12/2009 | Crooke |
| 7,662,558 B2 | 2/2010 | Liew |
| 7,666,854 B2 | 2/2010 | Seth et al. |
| 7,666,888 B2 | 2/2010 | Bartberger et al. |
| 7,683,036 B2 | 3/2010 | Esau et al. |
| 7,695,902 B2 | 4/2010 | Crooke |
| 7,696,345 B2 | 4/2010 | Allerson et al. |
| 7,718,623 B2 | 5/2010 | Kitagawa et al. |
| 7,723,508 B2 | 5/2010 | Crooke et al. |
| 7,732,590 B2 | 6/2010 | Bhanot et al. |
| 7,732,660 B2 | 6/2010 | Helliwell et al. |
| 7,741,305 B2 | 6/2010 | Crooke et al. |
| 7,749,700 B2 | 7/2010 | Baird et al. |
| 7,750,131 B2 | 7/2010 | Seth et al. |
| 7,750,141 B2 | 7/2010 | Crooke et al. |
| 7,750,731 B2 | 7/2010 | Poulsen et al. |
| 7,759,318 B1 | 7/2010 | Perera et al. |
| 7,776,344 B2 | 8/2010 | Hartmann et al. |
| 7,776,874 B2 | 8/2010 | Yao et al. |
| 7,777,023 B2 | 8/2010 | Vargeese et al. |
| 7,803,930 B2 | 9/2010 | Crooke et al. |
| 7,807,816 B2 | 10/2010 | Wilton et al. |
| 7,812,003 B2 | 10/2010 | Safe et al. |
| 7,838,287 B2 | 11/2010 | Goldsmith et al. |
| 7,863,252 B2 | 1/2011 | Crooke et al. |
| 7,884,086 B2 | 2/2011 | Bennett et al. |
| 7,884,117 B2 | 2/2011 | Zhang et al. |
| 7,888,324 B2 | 2/2011 | Crooke et al. |
| 7,893,039 B2 | 2/2011 | Swayze et al. |
| 7,919,472 B2 | 4/2011 | Monia et al. |
| 7,947,658 B2 | 5/2011 | Aronin et al. |
| 7,951,934 B2 | 5/2011 | Freier |
| 7,960,541 B2 | 6/2011 | Wilton et al. |
| 7,973,015 B2 | 7/2011 | van Ommen et al. |
| 8,003,619 B2 | 8/2011 | Hartmann et al. |
| 8,008,011 B2 | 8/2011 | Schmutz et al. |
| 8,008,459 B2 | 8/2011 | Goldsmith et al. |
| 8,039,235 B2 | 10/2011 | Lin et al. |
| 8,058,288 B2 | 11/2011 | Yao et al. |
| 8,067,173 B2 | 11/2011 | Liew |
| 8,076,303 B2 | 12/2011 | Iyer et al. |
| 8,084,437 B2 | 12/2011 | Freier et al. |
| 8,084,600 B2 | 12/2011 | Natt et al. |
| 8,088,582 B2 | 1/2012 | Sampath et al. |
| 8,093,222 B2 | 1/2012 | Freier et al. |
| 8,093,225 B2 | 1/2012 | Mamet |
| 8,101,348 B2 | 1/2012 | Tuschl et al. |
| 8,101,358 B2 | 1/2012 | Liew |
| 8,101,585 B2 | 1/2012 | Yu et al. |
| 8,101,743 B2 | 1/2012 | Brown-Driver et al. |
| 8,106,025 B2 | 1/2012 | Bennett et al. |
| 8,110,358 B2 | 2/2012 | Liew |
| 8,110,558 B2 | 2/2012 | Bennett et al. |
| 8,114,597 B2 | 2/2012 | Liew |
| 8,124,745 B2 | 2/2012 | Allerson et al. |
| 8,133,674 B2 | 3/2012 | Liew |
| 8,133,675 B2 | 3/2012 | Liew |
| 8,133,876 B2 | 3/2012 | Bennett et al. |
| 8,138,328 B2 | 3/2012 | Crooke et al. |
| 8,143,230 B2 | 3/2012 | Bhanot et al. |
| 8,148,072 B2 | 4/2012 | Liew |
| 8,158,598 B2 | 4/2012 | Bhanot et al. |
| 8,178,506 B2 | 5/2012 | Lollo et al. |
| 8,188,059 B2 | 5/2012 | Bhanot et al. |
| 8,206,923 B2 | 6/2012 | Garza Gonzalez et al. |
| 8,207,263 B2 | 6/2012 | Popot et al. |
| 8,232,384 B2 | 7/2012 | Wilton et al. |
| 8,257,922 B2 | 9/2012 | Liew |
| 8,258,289 B2 | 9/2012 | Bhanot et al. |
| 8,361,977 B2 | 1/2013 | Baker et al. |
| 8,383,660 B2 | 2/2013 | Chang et al. |
| 8,415,465 B2 | 4/2013 | Freier |
| 8,431,693 B2 | 4/2013 | Manoharan et al. |
| 8,450,474 B2 | 5/2013 | Wilton et al. |
| 8,455,634 B2 | 6/2013 | Wilton et al. |
| 8,455,635 B2 | 6/2013 | Wilton et al. |
| 8,455,636 B2 | 6/2013 | Wilton et al. |
| 8,470,987 B2 | 6/2013 | Wada et al. |
| 8,476,423 B2 | 7/2013 | Wilton et al. |
| 8,481,710 B2 | 7/2013 | Davidson et al. |
| 8,486,907 B2 | 7/2013 | Wilton et al. |
| 8,501,414 B2 | 8/2013 | Danzer et al. |
| 8,524,880 B2 | 9/2013 | Wilton et al. |
| 8,557,549 B2 | 10/2013 | Chang et al. |
| 8,592,566 B2 | 11/2013 | Iwamura et al. |
| 8,632,963 B2 | 1/2014 | Shah et al. |
| 8,633,206 B2 | 1/2014 | Promo et al. |
| 8,647,742 B2 | 2/2014 | Dendukuri et al. |
| 8,648,186 B2 | 2/2014 | Monteleone |
| 8,669,058 B2 | 3/2014 | Liew |
| 8,674,044 B2 | 3/2014 | Popot et al. |
| 8,679,750 B2 | 3/2014 | Hayden et al. |
| 8,680,063 B2 | 3/2014 | Aronin et al. |
| 8,729,036 B2 | 5/2014 | Zamore et al. |
| 8,735,417 B2 | 5/2014 | Altman et al. |
| 8,750,507 B2 | 6/2014 | Roosta et al. |
| 8,754,107 B2 | 6/2014 | George et al. |
| 8,759,507 B2 | 6/2014 | Van Deutekom |
| 8,809,516 B2 | 8/2014 | Manoharan et al. |
| 8,822,671 B2 | 9/2014 | Shimizu et al. |
| 8,859,755 B2 | 10/2014 | Wada et al. |
| 8,877,435 B2 | 11/2014 | Helliwell et al. |
| 8,883,969 B2 | 11/2014 | Ide et al. |
| 8,952,145 B2 | 2/2015 | Freier |
| 8,957,040 B2 | 2/2015 | Bennett et al. |
| 8,957,042 B2 | 2/2015 | Safe et al. |
| 8,975,389 B2 | 3/2015 | Manoharan et al. |
| 8,980,853 B2 | 3/2015 | Bennett et al. |
| 8,987,222 B2 | 3/2015 | Aronin et al. |
| 8,993,738 B2 | 3/2015 | Prakash et al. |
| 9,006,198 B2 | 4/2015 | Bennett et al. |
| 9,018,368 B2 | 4/2015 | Wilton et al. |
| 9,024,007 B2 | 5/2015 | Wilton et al. |
| 9,035,040 B2 | 5/2015 | Wilton et al. |
| 9,040,674 B2 | 5/2015 | Benson et al. |
| 9,057,066 B2 | 6/2015 | Hung et al. |
| 9,121,020 B2 | 9/2015 | Feinstein et al. |
| 9,126,927 B2 | 9/2015 | Yao et al. |
| 9,127,123 B2 | 9/2015 | Livingston et al. |

(56) References Cited

U.S. PATENT DOCUMENTS

| | | | |
|---|---|---|---|
| 9,175,286 B2 | 11/2015 | Wilton et al. |
| 9,249,416 B2 | 2/2016 | Wilton et al. |
| 9,260,716 B2 | 2/2016 | Davidson et al. |
| 9,273,315 B2 | 3/2016 | Hung et al. |
| 9,284,344 B2 | 3/2016 | Kim et al. |
| 9,308,252 B2 | 4/2016 | Suckow et al. |
| 9,353,372 B2 | 5/2016 | Freier |
| 9,382,575 B2 | 7/2016 | Eom et al. |
| 9,394,333 B2 | 7/2016 | Wada et al. |
| 9,422,555 B2 | 8/2016 | Wilton et al. |
| 9,441,229 B2 | 9/2016 | Wilton et al. |
| 9,447,415 B2 | 9/2016 | Wilton et al. |
| 9,453,228 B2 | 9/2016 | Kandimalla et al. |
| 9,476,044 B2 | 10/2016 | Tuschl et al. |
| 9,480,740 B2 | 11/2016 | Reed et al. |
| 9,598,458 B2 | 3/2017 | Shimizu et al. |
| 9,605,019 B2 | 3/2017 | Verdine et al. |
| 9,605,262 B2 | 3/2017 | Wilton et al. |
| 9,611,472 B2 | 4/2017 | Zamore et al. |
| 9,617,547 B2 * | 4/2017 | Gemba ................ C12N 15/117 |
| 9,695,211 B2 | 7/2017 | Wada et al. |
| 2001/0055761 A1 | 12/2001 | Kanemoto et al. |
| 2002/0013792 A1 | 1/2002 | Imielinski et al. |
| 2002/0082227 A1 | 6/2002 | Henry |
| 2002/0137921 A1 | 9/2002 | Cook |
| 2003/0045705 A1 | 3/2003 | Cook et al. |
| 2003/0049662 A1 | 3/2003 | Monia et al. |
| 2003/0050261 A1 | 3/2003 | Krieg et al. |
| 2003/0232978 A1 | 12/2003 | Seeberger et al. |
| 2003/0235845 A1 | 12/2003 | van Ommen et al. |
| 2004/0063647 A1 | 4/2004 | Johnson |
| 2004/0203145 A1 | 10/2004 | Zamore et al. |
| 2004/0213780 A1 | 10/2004 | Krainc |
| 2005/0042646 A1 | 2/2005 | Davidson et al. |
| 2005/0059619 A1 | 3/2005 | Krieg et al. |
| 2005/0096284 A1 | 5/2005 | McSwiggen |
| 2005/0159375 A1 | 7/2005 | Srivastava et al. |
| 2005/0169888 A1 | 8/2005 | Hartmann et al. |
| 2005/0176045 A1 | 8/2005 | Fedorov et al. |
| 2005/0239102 A1 | 10/2005 | Verdine et al. |
| 2005/0277133 A1 | 12/2005 | McSwiggen |
| 2005/0277609 A1 | 12/2005 | Krieg et al. |
| 2006/0003962 A1 | 1/2006 | Ahluwalia et al. |
| 2006/0035858 A1 | 2/2006 | Geary et al. |
| 2006/0041115 A1 | 2/2006 | Ravikumar |
| 2006/0063730 A1 | 3/2006 | Monia et al. |
| 2006/0099616 A1 | 5/2006 | van Ommen et al. |
| 2006/0147952 A1 | 7/2006 | van Ommen et al. |
| 2006/0166910 A1 | 7/2006 | Tuschl et al. |
| 2006/0211644 A1 | 9/2006 | Krieg et al. |
| 2006/0257912 A1 | 11/2006 | Kaemmerer et al. |
| 2007/0099860 A1 | 5/2007 | Sah et al. |
| 2007/0123484 A1 | 5/2007 | Bhat et al. |
| 2007/0149462 A1 | 6/2007 | Iyer et al. |
| 2007/0161547 A1 | 7/2007 | Bhat et al. |
| 2007/0161590 A1 | 7/2007 | Van Bilsen et al. |
| 2007/0249589 A1 | 10/2007 | Aebi et al. |
| 2007/0282097 A1 | 12/2007 | Ohgi et al. |
| 2007/0287831 A1 | 12/2007 | Seth et al. |
| 2007/0299027 A1 | 12/2007 | Hung et al. |
| 2008/0015158 A1 | 1/2008 | Ichiro et al. |
| 2008/0015162 A1 | 1/2008 | Bhanot et al. |
| 2008/0039418 A1 | 2/2008 | Freier |
| 2008/0045473 A1 | 2/2008 | Uhlmann et al. |
| 2008/0064867 A1 | 3/2008 | Leuck et al. |
| 2008/0119426 A1 | 5/2008 | Dale |
| 2008/0200409 A1 | 8/2008 | Wilson et al. |
| 2008/0209581 A1 | 8/2008 | van Ommen et al. |
| 2008/0221055 A1 | 9/2008 | Sah et al. |
| 2008/0221303 A1 | 9/2008 | Katzhendler et al. |
| 2008/0249291 A1 | 10/2008 | Kwon et al. |
| 2008/0274989 A1 | 11/2008 | Davidson et al. |
| 2009/0012120 A1 | 1/2009 | Borhan et al. |
| 2009/0023675 A1 | 1/2009 | McSwiggen et al. |
| 2009/0053148 A1 | 2/2009 | Kandimalla et al. |
| 2009/0053205 A1 | 2/2009 | Kandimalla et al. |
| 2009/0060898 A1 | 3/2009 | Kandimalla et al. |
| 2009/0062224 A1 | 3/2009 | Kim et al. |
| 2009/0076246 A1 | 3/2009 | van Deutekom |
| 2009/0093425 A1 | 4/2009 | Dowdy et al. |
| 2009/0162316 A1 | 6/2009 | Verdine et al. |
| 2009/0186410 A1 | 7/2009 | Aronin et al. |
| 2009/0228998 A1 | 9/2009 | van Ommen et al. |
| 2009/0263413 A1 | 10/2009 | Iwamura et al. |
| 2009/0306176 A1 | 12/2009 | Schlingensiepen et al. |
| 2010/0008937 A1 | 1/2010 | Peer et al. |
| 2010/0008981 A1 | 1/2010 | Kaemmerer et al. |
| 2010/0038543 A1 | 2/2010 | Toda et al. |
| 2010/0069472 A1 | 3/2010 | Hung et al. |
| 2010/0120900 A1 | 5/2010 | van Bilsen et al. |
| 2010/0215642 A1 | 8/2010 | Lan et al. |
| 2010/0273999 A1 | 10/2010 | Jung et al. |
| 2010/0299768 A1 | 11/2010 | Perrin et al. |
| 2010/0325746 A9 | 12/2010 | Kaemmerer et al. |
| 2011/0009477 A1 | 1/2011 | Yu et al. |
| 2011/0015253 A1 | 1/2011 | Wilton et al. |
| 2011/0015258 A1 | 1/2011 | Wilton et al. |
| 2011/0039334 A1 | 2/2011 | Bennett et al. |
| 2011/0046203 A1 | 2/2011 | Wilton et al. |
| 2011/0105587 A1 | 5/2011 | Fishcher et al. |
| 2011/0111491 A1 | 5/2011 | Davidson et al. |
| 2011/0136765 A1 | 6/2011 | Promo et al. |
| 2011/0178284 A1 | 7/2011 | Wada et al. |
| 2011/0201599 A1 | 8/2011 | Bahceci et al. |
| 2011/0212520 A1 | 9/2011 | Davidson et al. |
| 2011/0213010 A1 | 9/2011 | Hayden et al. |
| 2011/0257251 A1 | 10/2011 | Gude-Rodriguez et al. |
| 2011/0263686 A1 | 10/2011 | Wilton et al. |
| 2011/0269814 A1 | 11/2011 | Manoharan et al. |
| 2011/0294124 A1 | 12/2011 | Wada et al. |
| 2011/0294869 A1 | 12/2011 | Petersen |
| 2011/0306652 A1 | 12/2011 | Freier |
| 2011/0312086 A1 | 12/2011 | Van Deutekom |
| 2012/0022144 A1 | 1/2012 | Wilton et al. |
| 2012/0022145 A1 | 1/2012 | Wilton et al. |
| 2012/0029057 A1 | 2/2012 | Wilton et al. |
| 2012/0029058 A1 | 2/2012 | Wilton et al. |
| 2012/0029059 A1 | 2/2012 | Wilton et al. |
| 2012/0029060 A1 | 2/2012 | Wilton et al. |
| 2012/0041050 A1 | 2/2012 | Wilton et al. |
| 2012/0095076 A1 | 4/2012 | Sah et al. |
| 2012/0136039 A1 | 5/2012 | Aronin et al. |
| 2012/0156138 A1 | 6/2012 | Smith |
| 2012/0208864 A1 | 8/2012 | Bhanot et al. |
| 2012/0246747 A1 | 9/2012 | Tuschl et al. |
| 2012/0252879 A1 | 10/2012 | Hung et al. |
| 2012/0308609 A1 | 12/2012 | Gibbon et al. |
| 2012/0316224 A1 | 12/2012 | Verdine et al. |
| 2013/0005794 A1 | 1/2013 | Kaemmerer et al. |
| 2013/0046008 A1 | 2/2013 | Bennett et al. |
| 2013/0072671 A1 | 3/2013 | Van Deutekom |
| 2013/0116310 A1 | 5/2013 | Wilton et al. |
| 2013/0178612 A1 | 7/2013 | Wada et al. |
| 2013/0184450 A1 | 7/2013 | Wada et al. |
| 2013/0189782 A1 | 7/2013 | Hung et al. |
| 2013/0197061 A1 | 8/2013 | Hohjoh et al. |
| 2013/0217755 A1 | 8/2013 | Wilton et al. |
| 2013/0236536 A1 | 9/2013 | Phiasivongsa et al. |
| 2013/0253033 A1 | 9/2013 | Wilton et al. |
| 2013/0253178 A1 | 9/2013 | Shimizu et al. |
| 2013/0253180 A1 | 9/2013 | Wilton et al. |
| 2013/0274313 A1 | 10/2013 | Wilton et al. |
| 2013/0281684 A1 | 10/2013 | Freier |
| 2013/0302806 A1 | 11/2013 | Van Deutekom |
| 2013/0323836 A1 | 12/2013 | Manoharan et al. |
| 2013/0331438 A1 | 12/2013 | Wilton et al. |
| 2014/0080896 A1 | 3/2014 | Nelson et al. |
| 2014/0080898 A1 | 3/2014 | Wilton et al. |
| 2014/0107330 A1 | 4/2014 | Freier et al. |
| 2014/0120088 A1 | 5/2014 | Carpentier |
| 2014/0142160 A1 | 5/2014 | Lee et al. |
| 2014/0155587 A1 | 6/2014 | Wilton et al. |
| 2014/0163213 A1 | 6/2014 | Debelak et al. |
| 2014/0194610 A1 | 7/2014 | Verdine et al. |

(56) References Cited

U.S. PATENT DOCUMENTS

| | | |
|---|---|---|
| 2014/0213635 A1 | 7/2014 | Van Deutekom |
| 2014/0221395 A1 | 8/2014 | Dhanoa |
| 2014/0243515 A1 | 8/2014 | Wilton et al. |
| 2014/0243516 A1 | 8/2014 | Wilton et al. |
| 2014/0256578 A1 | 9/2014 | Hayden et al. |
| 2014/0275212 A1 | 9/2014 | van Deutekom |
| 2014/0309283 A1 | 10/2014 | Wilton et al. |
| 2014/0309284 A1 | 10/2014 | Wilton et al. |
| 2014/0309285 A1 | 10/2014 | Wilton et al. |
| 2014/0323707 A1 | 10/2014 | Seth et al. |
| 2014/0350076 A1 | 11/2014 | van Deutekom |
| 2014/0357698 A1 | 12/2014 | Van Deutekom et al. |
| 2014/0357855 A1 | 12/2014 | Van Deutekom et al. |
| 2014/0373188 A1 | 12/2014 | Zamore et al. |
| 2014/0378527 A1 | 12/2014 | van Deutekom |
| 2015/0051389 A1 | 2/2015 | Seth et al. |
| 2015/0057330 A1 | 2/2015 | Wilton et al. |
| 2015/0080563 A2 | 3/2015 | van Deutekom |
| 2015/0096064 A1 | 4/2015 | Tuschl et al. |
| 2015/0166999 A1 | 6/2015 | Gemba |
| 2015/0197540 A1 | 7/2015 | Shimizu et al. |
| 2015/0211006 A1 | 7/2015 | Butler et al. |
| 2015/0218559 A1 | 8/2015 | Van Deutekom et al. |
| 2015/0275208 A1 | 10/2015 | Oestergaard et al. |
| 2015/0292015 A1 | 10/2015 | Bennett et al. |
| 2015/0307877 A1 | 10/2015 | Freier |
| 2015/0322434 A1 | 11/2015 | van Deutekom |
| 2015/0329859 A1 | 11/2015 | Bennett et al. |
| 2015/0335708 A1 | 11/2015 | Froelich et al. |
| 2015/0353931 A1 | 12/2015 | Wilton et al. |
| 2015/0361424 A1 | 12/2015 | van Deutekom |
| 2015/0376615 A1 | 12/2015 | Wilton et al. |
| 2015/0376616 A1 | 12/2015 | Wilton et al. |
| 2015/0376624 A1 | 12/2015 | Gryaznov et al. |
| 2015/0376625 A1 | 12/2015 | Oestergaard et al. |
| 2016/0002631 A1 | 1/2016 | Wilton et al. |
| 2016/0002632 A1 | 1/2016 | Wilton et al. |
| 2016/0002635 A1 | 1/2016 | Wilton et al. |
| 2016/0017327 A1 | 1/2016 | Rudnicki et al. |
| 2016/0040161 A1 | 2/2016 | Packard et al. |
| 2016/0053256 A1 | 2/2016 | Hung et al. |
| 2016/0076033 A1 | 3/2016 | Torii et al. |
| 2016/0138022 A1 | 5/2016 | Kandimalla et al. |
| 2016/0168570 A1 | 6/2016 | Van Deutekom et al. |
| 2016/0186175 A1 | 6/2016 | Seth et al. |
| 2016/0186178 A1 | 6/2016 | Radovic-Moreno et al. |
| 2016/0186185 A1 | 6/2016 | Prakash et al. |
| 2016/0194349 A1 | 7/2016 | Prakash et al. |
| 2016/0194636 A1 | 7/2016 | Van Deutekom et al. |
| 2016/0251653 A1 | 9/2016 | Davidson et al. |
| 2016/0251658 A1 | 9/2016 | Van Deutekom et al. |
| 2016/0264964 A1 | 9/2016 | Cancilla et al. |
| 2016/0312217 A1 | 10/2016 | Hung et al. |
| 2016/0331835 A1 | 11/2016 | Gemba et al. |
| 2016/0333349 A1 | 11/2016 | Gemba et al. |
| 2016/0347780 A1 | 12/2016 | Wada et al. |
| 2016/0347784 A1 | 12/2016 | Verdine et al. |
| 2016/0355810 A1 | 12/2016 | Van Deutekom |
| 2016/0369273 A1 | 12/2016 | Freier |
| 2017/0009233 A1 | 1/2017 | Wilton et al. |
| 2017/0009234 A1 | 1/2017 | Wilton et al. |
| 2017/0029445 A1 | 2/2017 | Shimizu et al. |
| 2017/0029457 A1 | 2/2017 | Verdine et al. |
| 2017/0037399 A1 | 2/2017 | Meena et al. |
| 2017/0044526 A1 | 2/2017 | Wan et al. |
| 2017/0067050 A1 | 3/2017 | Tuschl et al. |
| 2017/0130224 A1 | 5/2017 | Oestergaard et al. |
| 2017/0275621 A1 | 9/2017 | Butler et al. |

FOREIGN PATENT DOCUMENTS

| | | | |
|---|---|---|---|
| DE | 01934150 A1 | | 1/1970 |
| EP | 0 002 322 A2 | | 6/1979 |
| EP | 192521 A1 | | 8/1986 |
| EP | 269258 A2 | | 6/1988 |
| EP | 0506242 A1 | | 9/1992 |
| EP | 0531447 A1 | | 3/1993 |
| EP | 0604409 A1 | | 7/1994 |
| EP | 0655088 A1 | | 5/1995 |
| EP | 0779893 A2 | | 6/1997 |
| EP | 0831854 A1 | | 4/1998 |
| EP | 0973945 A1 | | 1/2000 |
| EP | 1097162 A2 | | 5/2001 |
| EP | 1100807 A1 | | 5/2001 |
| EP | 1185305 | | 3/2002 |
| EP | 1244682 A1 | | 10/2002 |
| EP | 1311526 A1 | | 5/2003 |
| EP | 1418179 A2 | | 5/2004 |
| EP | 1499627 A2 | | 1/2005 |
| EP | 1539188 A2 | | 6/2005 |
| EP | 1556077 A2 | | 7/2005 |
| EP | 1560840 A2 | | 8/2005 |
| EP | 1562971 A2 | | 8/2005 |
| EP | 1670810 A2 | | 6/2006 |
| EP | 1670896 A2 | | 6/2006 |
| EP | 1795536 A1 | | 6/2007 |
| EP | 1957507 A2 | | 8/2008 |
| EP | 1984381 A2 | | 10/2008 |
| EP | 2021472 A2 | | 2/2009 |
| EP | 2062980 A2 | | 5/2009 |
| EP | 2066684 A2 | | 6/2009 |
| EP | 2149571 A1 | | 2/2010 |
| EP | 2161038 A1 | | 3/2010 |
| EP | 2170917 A2 | | 4/2010 |
| EP | 2173760 A2 | | 4/2010 |
| EP | 2176280 A2 | | 4/2010 |
| EP | 2282744 A1 | | 2/2011 |
| EP | 2285819 A1 | | 2/2011 |
| EP | 2316967 A1 | | 5/2011 |
| EP | 2360166 A1 | | 8/2011 |
| EP | 1 866 319 B1 | | 11/2011 |
| EP | 2399588 A1 | | 12/2011 |
| EP | 2422819 A2 | | 2/2012 |
| EP | 2428227 A1 | | 3/2012 |
| EP | 2462153 A2 | | 6/2012 |
| EP | 2479182 A1 | | 7/2012 |
| EP | 1606407 B1 | | 12/2013 |
| EP | 14193887.8 | | 11/2014 |
| EP | 14198167.0 | | 12/2014 |
| EP | 15182401.8 | | 8/2015 |
| EP | 15191074.2 | | 10/2015 |
| EP | 15191075.9 | | 10/2015 |
| EP | 15191076.7 | | 10/2015 |
| EP | 2982758 A1 | | 2/2016 |
| EP | 2125852 B1 | | 4/2016 |
| EP | 2370451 B1 | | 11/2016 |
| EP | 2 534 262 B1 | | 12/2016 |
| GB | 1448437 A | | 9/1976 |
| GB | 2016273 A | | 9/1979 |
| JP | 3072345 B1 | | 7/2000 |
| JP | 2003/238586 A | | 8/2003 |
| JP | 2009-190983 A | | 8/2009 |
| JP | 4348044 B2 | | 10/2009 |
| JP | 04348077 B2 | | 10/2009 |
| JP | A03-074398 | | 3/2011 |
| JP | 2011/088935 A | | 5/2011 |
| WO | WO-91/10671 A1 | | 7/1991 |
| WO | WO-91/16331 A1 | | 10/1991 |
| WO | WO-91/17755 A1 | | 11/1991 |
| WO | WO-93/08296 A1 | | 4/1993 |
| WO | WO-94/17093 A1 | | 8/1994 |
| WO | WO-94/22890 A1 | | 10/1994 |
| WO | WO-96/02555 A1 | | 2/1996 |
| WO | WO-96/07392 A2 | | 3/1996 |
| WO | WO-96/14329 A1 | | 5/1996 |
| WO | WO-96/19572 A1 | | 6/1996 |
| WO | WO-96/37504 A1 | | 11/1996 |
| WO | WO-96/39413 A1 | | 12/1996 |
| WO | WO-97/06183 A1 | | 2/1997 |
| WO | WO-97/09443 A1 | | 3/1997 |
| WO | WO-97/14710 A1 | | 4/1997 |
| WO | WO-97/47637 A1 | | 12/1997 |
| WO | WO-98/02582 A2 | | 1/1998 |
| WO | WO-98/03542 A1 | | 1/1998 |

(56) References Cited

FOREIGN PATENT DOCUMENTS

| | | |
|---|---|---|
| WO | WO-98/07734 A1 | 2/1998 |
| WO | WO-98/18810 A1 | 5/1998 |
| WO | WO-98/39334 A1 | 9/1998 |
| WO | WO-98/46794 A1 | 10/1998 |
| WO | WO-98/53801 A1 | 12/1998 |
| WO | WO-99/05160 A2 | 2/1999 |
| WO | WO-99/12034 A1 | 3/1999 |
| WO | WO-99/56755 A1 | 11/1999 |
| WO | WO-99/58118 A2 | 11/1999 |
| WO | WO-00/00499 A1 | 1/2000 |
| WO | WO-00/04034 A2 | 1/2000 |
| WO | WO-00/06588 A1 | 2/2000 |
| WO | WO-00/09159 A1 | 2/2000 |
| WO | WO-00/23444 A1 | 4/2000 |
| WO | WO-00/31110 A1 | 6/2000 |
| WO | WO-00/37658 A2 | 6/2000 |
| WO | WO-00/55179 A1 | 9/2000 |
| WO | WO-00/58329 A1 | 10/2000 |
| WO | WO-00/76554 A1 | 12/2000 |
| WO | WO-01/02415 A1 | 1/2001 |
| WO | WO-01/022990 A2 | 4/2001 |
| WO | WO-01/27126 A1 | 4/2001 |
| WO | WO-01/40515 A1 | 6/2001 |
| WO | WO-01/49701 A1 | 7/2001 |
| WO | WO-01/64702 A1 | 9/2001 |
| WO | WO-01/81303 A1 | 11/2001 |
| WO | WO-01/85751 A1 | 11/2001 |
| WO | WO-01/88198 A1 | 11/2001 |
| WO | WO-02/14340 A1 | 2/2002 |
| WO | WO-02/15410 A2 | 2/2002 |
| WO | WO-02/20544 A1 | 3/2002 |
| WO | WO-02/22635 A1 | 3/2002 |
| WO | WO-02/24906 A1 | 3/2002 |
| WO | WO-02/32450 A2 | 4/2002 |
| WO | WO-02/57425 A2 | 7/2002 |
| WO | WO-2002/051716 A1 | 7/2002 |
| WO | WO-02/97134 A2 | 12/2002 |
| WO | WO-02/099317 A1 | 12/2002 |
| WO | WO-03/002065 A2 | 1/2003 |
| WO | WO-03/004602 A2 | 1/2003 |
| WO | WO-03/011887 A2 | 2/2003 |
| WO | WO-03/012057 A2 | 2/2003 |
| WO | WO-03/014306 A2 | 2/2003 |
| WO | WO-03/014307 A2 | 2/2003 |
| WO | WO-03/018600 A2 | 3/2003 |
| WO | WO-03/066633 A1 | 8/2003 |
| WO | WO-03/097662 A1 | 11/2003 |
| WO | WO-03/099840 A1 | 12/2003 |
| WO | WO-03/100017 A2 | 12/2003 |
| WO | WO-03/106477 A1 | 12/2003 |
| WO | WO-2004/000351 A1 | 12/2003 |
| WO | WO-2004/003228 A1 | 1/2004 |
| WO | WO-2004/007718 A2 | 1/2004 |
| WO | WO-2004/014933 A1 | 2/2004 |
| WO | WO-2004/016805 A2 | 2/2004 |
| WO | WO-2004010956 A2 | 2/2004 |
| WO | WO-2004/024919 A1 | 3/2004 |
| WO | WO-2004/039829 A2 | 5/2004 |
| WO | WO-2004041889 A2 | 5/2004 |
| WO | WO-2004044134 A2 | 5/2004 |
| WO | WO-2004044136 A2 | 5/2004 |
| WO | WO-2004044141 A2 | 5/2004 |
| WO | WO-2004044181 A2 | 5/2004 |
| WO | WO-2004/048522 A2 | 6/2004 |
| WO | WO-2004/055162 A2 | 7/2004 |
| WO | WO-2004/083432 A1 | 9/2004 |
| WO | WO-2004/083446 A2 | 9/2004 |
| WO | WO-2004/085454 A1 | 10/2004 |
| WO | WO-2004093783 A2 | 11/2004 |
| WO | WO-2005000201 A2 | 1/2005 |
| WO | WO-2005005599 A2 | 1/2005 |
| WO | WO-2005/014609 A2 | 2/2005 |
| WO | WO-2005013901 A2 | 2/2005 |
| WO | WO-2005/023828 A1 | 3/2005 |
| WO | WO-2005/028494 A1 | 3/2005 |
| WO | WO-2005019418 A2 | 3/2005 |
| WO | WO-2005023825 A2 | 3/2005 |
| WO | WO-2005023995 A2 | 3/2005 |
| WO | WO-2005/039630 A2 | 5/2005 |
| WO | WO-2005/042018 A2 | 5/2005 |
| WO | WO-2005/042716 A2 | 5/2005 |
| WO | WO-2005/070859 A1 | 8/2005 |
| WO | WO-2005/085272 A1 | 9/2005 |
| WO | WO-2005/092909 A1 | 10/2005 |
| WO | WO-2006/000057 A1 | 1/2006 |
| WO | WO-2006020676 A2 | 2/2006 |
| WO | WO 2006/022323 A1 | 3/2006 |
| WO | WO-2006/029258 A2 | 3/2006 |
| WO | WO-2006/031267 A2 | 3/2006 |
| WO | WO-2006031461 A2 | 3/2006 |
| WO | WO-2006044531 A2 | 4/2006 |
| WO | WO-2006/049454 A1 | 5/2006 |
| WO | WO-2006/053861 A1 | 5/2006 |
| WO | WO-2006/065751 A2 | 6/2006 |
| WO | WO-2006/066260 A2 | 6/2006 |
| WO | WO-2006/070284 A1 | 7/2006 |
| WO | WO-2006/080596 A1 | 8/2006 |
| WO | WO-2006/091915 A2 | 8/2006 |
| WO | WO-2006/117400 A2 | 11/2006 |
| WO | WO-2006/121960 A2 | 11/2006 |
| WO | WO-2007/002904 A2 | 1/2007 |
| WO | WO-2007/005941 A2 | 1/2007 |
| WO | WO-2007027775 A2 | 3/2007 |
| WO | WO-2007/041045 A2 | 4/2007 |
| WO | WO-2007/051045 A2 | 5/2007 |
| WO | WO-2007/059041 A2 | 5/2007 |
| WO | WO-2007/064291 A1 | 6/2007 |
| WO | WO-2007/070598 A2 | 6/2007 |
| WO | WO-2007064954 A2 | 6/2007 |
| WO | WO-2007/089584 A2 | 8/2007 |
| WO | WO-2007/089611 A2 | 8/2007 |
| WO | WO-2007/090071 A2 | 8/2007 |
| WO | WO-2007/095316 A2 | 8/2007 |
| WO | WO-2007131232 A2 | 11/2007 |
| WO | WO-2007131237 A2 | 11/2007 |
| WO | WO-2007131238 A2 | 11/2007 |
| WO | WO-2007134014 A2 | 11/2007 |
| WO | WO-2007136988 A2 | 11/2007 |
| WO | WO-2007/139190 A1 | 12/2007 |
| WO | WO-2007143315 A2 | 12/2007 |
| WO | WO-2007143316 A2 | 12/2007 |
| WO | WO-2007143317 A2 | 12/2007 |
| WO | WO-2007146511 A2 | 12/2007 |
| WO | WO-2008/005562 A2 | 1/2008 |
| WO | WO-2008/008476 A2 | 1/2008 |
| WO | WO-2008/021136 A2 | 2/2008 |
| WO | WO-2008017081 A1 | 2/2008 |
| WO | WO-2008/049085 A1 | 4/2008 |
| WO | WO-2008/051763 A1 | 5/2008 |
| WO | WO-2008/068638 A2 | 6/2008 |
| WO | WO-2008/073959 A2 | 6/2008 |
| WO | WO-2008066776 A2 | 6/2008 |
| WO | WO-2008/098104 A1 | 8/2008 |
| WO | WO-2008118883 A1 | 10/2008 |
| WO | WO-2008139262 A2 | 11/2008 |
| WO | WO-2008/148801 A2 | 12/2008 |
| WO | WO-2008/151833 A2 | 12/2008 |
| WO | WO-2009/007855 A2 | 1/2009 |
| WO | WO-2009046141 A2 | 4/2009 |
| WO | WO-2009/086264 A1 | 7/2009 |
| WO | WO-2009/089659 A1 | 7/2009 |
| WO | WO-2009/089689 A1 | 7/2009 |
| WO | WO-2009/098197 A1 | 8/2009 |
| WO | WO-2009/117589 A1 | 9/2009 |
| WO | WO-2009124238 A1 | 10/2009 |
| WO | WO-2009/135322 A1 | 11/2009 |
| WO | WO-2009/143387 A2 | 11/2009 |
| WO | WO-2009143390 A2 | 11/2009 |
| WO | WO-2009143391 A2 | 11/2009 |
| WO | WO-2009143463 A2 | 11/2009 |
| WO | WO-2009/146123 A2 | 12/2009 |
| WO | WO-2009148605 A2 | 12/2009 |
| WO | WO-2010/003133 A2 | 1/2010 |
| WO | WO-2010/039543 A2 | 4/2010 |

(56) References Cited

FOREIGN PATENT DOCUMENTS

| | | |
|---|---|---|
| WO | WO-2010/042636 A2 | 4/2010 |
| WO | WO-2010036696 A1 | 4/2010 |
| WO | WO-2010036698 A1 | 4/2010 |
| WO | WO-2010048552 A2 | 4/2010 |
| WO | WO-2010/064146 A2 | 6/2010 |
| WO | WO-2010/072831 A1 | 7/2010 |
| WO | WO-2010080953 A1 | 7/2010 |
| WO | WO-2010091301 A1 | 8/2010 |
| WO | WO-2010107838 A1 | 9/2010 |
| WO | WO-2010/118263 A1 | 10/2010 |
| WO | WO-2010120262 A1 | 10/2010 |
| WO | WO-2010/129853 A2 | 11/2010 |
| WO | WO-2010/141471 A2 | 12/2010 |
| WO | WO-2011/005761 A1 | 1/2011 |
| WO | WO-2011/005764 A1 | 1/2011 |
| WO | WO-2011/005860 A2 | 1/2011 |
| WO | WO-2011/015572 A1 | 2/2011 |
| WO | WO-2011/015573 A1 | 2/2011 |
| WO | WO-2011/017521 A2 | 2/2011 |
| WO | WO-2011/034072 A1 | 3/2011 |
| WO | WO-2011038288 A1 | 3/2011 |
| WO | WO-2011/045702 A1 | 4/2011 |
| WO | WO-2011085271 A2 | 7/2011 |
| WO | WO-2011/097643 A1 | 8/2011 |
| WO | WO-2011/097644 A2 | 8/2011 |
| WO | WO-2011/108682 A1 | 9/2011 |
| WO | WO-2011/133871 A2 | 10/2011 |
| WO | WO-2011127175 A1 | 10/2011 |
| WO | WO-2011127307 A1 | 10/2011 |
| WO | WO-2011/139699 A2 | 11/2011 |
| WO | WO-2011/139911 A2 | 11/2011 |
| WO | WO-2012/030683 A2 | 3/2012 |
| WO | WO-2012/039448 A1 | 3/2012 |
| WO | WO-2012/073857 A1 | 6/2012 |
| WO | WO-2012/151324 A1 | 11/2012 |
| WO | WO-2013/012758 A1 | 1/2013 |
| WO | WO-2013/022984 A1 | 2/2013 |
| WO | WO-2013/022990 A1 | 2/2013 |
| WO | WO-2014/010250 A1 | 1/2014 |
| WO | WO-2014/010718 A1 | 1/2014 |
| WO | WO-2014/012081 A2 | 1/2014 |
| WO | WO-2014/025805 A1 | 2/2014 |
| WO | WO-2014/028739 A1 | 2/2014 |
| WO | WO-2014/059356 A2 | 4/2014 |
| WO | WO-2014/076195 A1 | 5/2014 |
| WO | WO-2014/076196 A1 | 5/2014 |
| WO | WO-2014/080004 A1 | 5/2014 |
| WO | WO-2014/118267 A1 | 8/2014 |
| WO | WO-2014/118272 A1 | 8/2014 |
| WO | WO-2014/179626 A2 | 11/2014 |
| WO | WO-2014/188001 A1 | 11/2014 |
| WO | WO-2014/207232 A1 | 12/2014 |
| WO | WO-2015/010135 A2 | 1/2015 |
| WO | WO 2015/051214 A1 | 4/2015 |
| WO | WO-2015/051366 A2 | 4/2015 |
| WO | WO-2015/070212 A1 | 5/2015 |
| WO | WO-2015/071388 A1 | 5/2015 |
| WO | WO-2015/089511 A2 | 6/2015 |
| WO | WO-2015/107425 A2 | 7/2015 |
| WO | WO-2015/108046 A1 | 7/2015 |
| WO | WO-2015/108047 A1 | 7/2015 |
| WO | WO-2015/108048 A1 | 7/2015 |
| WO | WO-2015/168172 A1 | 11/2015 |
| WO | WO-2015/171932 A1 | 11/2015 |
| WO | WO-2015/179525 A1 | 11/2015 |
| WO | WO-2016/011226 A1 | 1/2016 |
| WO | WO-2016/020399 A1 | 2/2016 |
| WO | WO-2016/027168 A2 | 2/2016 |
| WO | WO-2016/037191 A1 | 3/2016 |
| WO | WO-2016/079181 A1 | 5/2016 |
| WO | WO-2016/079183 A1 | 5/2016 |
| WO | WO-2016/096938 A1 | 6/2016 |
| WO | WO-2016/102664 A1 | 6/2016 |
| WO | WO-2016/127000 A1 | 8/2016 |
| WO | WO-2016/127002 A1 | 8/2016 |
| WO | WO-2016/130589 A2 | 8/2016 |
| WO | WO-2016/130806 A2 | 8/2016 |
| WO | WO-2016/138017 A1 | 9/2016 |
| WO | WO-2016/141236 A1 | 9/2016 |
| WO | WO-2016/154096 A1 | 9/2016 |
| WO | WO-2016/161374 A1 | 10/2016 |
| WO | WO-2016/164896 A2 | 10/2016 |
| WO | WO-2016/167780 A1 | 10/2016 |
| WO | WO-2016/209862 A1 | 12/2016 |
| WO | WO-2017/004261 A1 | 1/2017 |
| WO | WO-2017/011276 A1 | 1/2017 |
| WO | WO-2017/011286 A1 | 1/2017 |
| WO | WO-2017/015109 A1 | 1/2017 |
| WO | WO-2017/015555 | 1/2017 |
| WO | WO-2017/015575 | 1/2017 |
| WO | WO-2017/019660 A1 | 2/2017 |
| WO | WO-2017/023660 A1 | 2/2017 |
| WO | WO-2017/032726 A1 | 3/2017 |
| WO | WO-2017/035340 A1 | 3/2017 |
| WO | WO-2017/040078 A1 | 3/2017 |
| WO | WO-2017/055423 A1 | 4/2017 |
| WO | WO-2017/062862 A2 | 4/2017 |
| WO | WO-2017/067970 A1 | 4/2017 |
| WO | WO-2017/068087 A1 | 4/2017 |
| WO | WO-2017/081223 A1 | 5/2017 |
| WO | WO-2017/157672 A1 | 9/2017 |
| WO | WO-2017/157899 A1 | 9/2017 |
| WO | WO-2017/160741 A1 | 9/2017 |
| WO | WO-2017/178656 A1 | 10/2017 |
| WO | WO-2017/192679 A1 | 11/2017 |
| WO | WO-2017/194498 A1 | 11/2017 |
| WO | WO-2017/194664 A1 | 11/2017 |
| WO | WO-2017/210647 A1 | 12/2017 |

OTHER PUBLICATIONS

Ager, D.J. The Peterson olefination reaction, Organic Reactions, 38: 1-223 (2004).

Agrawal, S. and Kandimalla, E.R., Antisense and/or Immunostimulatory Oligonucleotide THerapeutics, Current Cancer Drug Targets, Bentham Science, 1(3): 1 page. URL: <http:www.eurekaselect.com/65087/article> [Retrieved Apr. 3, 2016].

Agrawal, S. and Tang, J.Y., GEM 91—an antisense oligonucleotide phosphorothioate as a therapeutic agent for AIDS, Antisense Research and Development, 2(4):261-266 (1992).

Agrawal, S. et al., Mixed-backbone oligonucleotides as second generation antisense oligonucleotides: In vitro and in vivo studies, Proc. Natl. Acad. Sci. USA, 94: 2620-2625 (1997).

Aldaye, F.A. et al., Assembling materials with DNA as the guide, Science, 321(5897): 1795-1799 (2008).

Aldrich Chemical Co. Catalog, 2007-2008 Issue, only p. 1719 supplied: see first full entry at col. 1 (S-methyl methanethiosulfonate), Milwaukee, WI.

Almer et al., Synthesis of Stereochemically Homogeneous Oligoribonucleoside All-Rp-Phosphorothioates by Combining H-Phosphonate Chemistry and Enzymatic Digestion, J. Chem. Soc., Chem. Commun., 1459-1460 (1994).

Almer, et al. A New Approach to Stereospecific Synthesis of P-chiral Phosphorothioates. Preparation of Diastereomeric Dithymidyl-(3'-5') Phosphorothioates, Chem. Commun., (3): 290-1 (2004).

Almer, et al. Solid Support Synthesis of all-Rp-oligo(ribonucleoside phosphorothioate)s, Nucleic Acids Research 24(19): 3811-3820 (1996).

Almer, H. et al., Synthesis of Diribonucleoside Phosphorothioates via Sterospecific Sulfurization of H-Phosphonate Diesters, J. Org. Chem., 57(23): 6163-6169 (1992).

Altschul, S.F. et al., Basic local alignment search tool, Journal of Molecular Biology, 215(3):403-410 (1990).

Altschul, S.F. et al., Gapped BLAST and PSI-BLAST: a new generation of protein database search programs, Nucleic Acids Research, 25(17):3389-3402 (1997).

Alul, R.H. et al., Oxalyl-CPG: a labile support for synthesis of sensitive oligonucleotide, Nucleic Acids Research, 19(7):1527-1532 (1991).

(56) References Cited

OTHER PUBLICATIONS

Alvarez, K. et al., Photocleavable Protecting Groups as Nucleobase Protections Allowed the Solid-Phase Synthesis of Base-Sensitive SATE-Prooligonucleotides, Journal of Organic Chemistry, 64(17): 6319-6328(1999).
Amarzguioui et al., Tolerance for mutations and chemical modifications in a siRNA, Nucleic Acids Research 31(2): 589-595 (2003).
Arai, K. et al., Synthesis and properties of novel 2'-O-alkoxymethyl-modified nucleic acids, Bioorganic & Medicinal Chemistry Letters, 21(21): 6285-6287 (2011).
Aristarkhova, L.N. et al., Investigation in the field of thiosulfonic acids. 28. alkyl esters of cyclopentane- and cyclohexanethiosulfonic acids, Journal of Organic Chemistry of the USSR, 6: 2454-2458 (1970).
Athyros, V.G. et al., Antisense technology for the prevention or the treatment of cardiovascular disease: the next blockbuster?, Expert Opin. Investig. Drugs, 17(7): 969-72 (2008).
Ausin, C. et al., Assesment of heat-sensitive thiophosphate protecting groups in the development of thermolytic DNA oligonucleotide prodrugs, Tetrahedron, 66(1):68-79 (2010).
Bachelin et al., Structure of a Stereoregular Phosphorothioate DNA/RNA duplex, Nat. Struct. Biol., 5(4): 271-276 (1998).
Baek, M-S. et al., In Vitro Metabolic Stabilities and Metabolism of 2'-O-(Methoxyethyl) Partially Modified Phosphorothioate Antisense Oligonucleotides in Preincubated Rat or Human Whole Liver Homogenates, Oligonucleotides, 20(6): 309-316 (2010).
Ballas, Z.K. et al., Induction of NK Activity in Murine and Human Cells by CpG Motifs in Oligodeoxynucleotides and Bacterial DNA, J. Immunoll., 57: 1840-1845 (1996).
Barber, I. et al., The Prooligonucleotides Approach I: Esterase-Mediated Reversibility of Dithymidine S-Alkyl Phosphorothiolates to Dithymidine Phosphorothioates, Bioorganic and Medicinal Chemistry Letters, 5(6):563-568 (1995).
Barber, I. et al., The Prooligonucleotides Approach II: Synthesis and stability studies of chimeric oligonucleotide models, Bioorganic and Medicinal Chemistry Letters, 5(14):1441-1444 (1995).
Barnes, P.J. and Peterson, S. Efficacy and Safety of Inhaled Corticosteroids in Asthma, Am. Rev. Respir. Dis., 148: SI-S26 (1993).
Bartz, H. et al., Poly-guanosine strings improve cellular uptake and stimulatory activity of phosphodiester CpG oligonucleotides in human leukocytes, Vaccine, 23: 148-155 (2004).
Battistini et al., Stereoselective Synthesis of Cyclic Dinucloetide Phosphorothioates, Tetrahedron, 49(5): 1115-1132 (1993).
Bayever, E. et al., Systematic administration of a phosphorothioate oligonucleotide with a sequence complementary to p53 for acute myelogenous leukemia and myelodysplastic syndrome: intial results of a phase I trial, Antisense Research Development, 3(4):383-390 (1993).
Beal, P.A. et al., Second Structural Motif for Recognition of DNA by Oligonucleotide-Directed Triple-Helix Formation, Science, 251: 1360-1363 (1991).
Beaucage, S.L. and Iyer, R.P., Advances in the Synthesis of Oligonucleotides by the Phosphoramidite Approach, Tetrahedron, 48(12):2223-2311 (1992).
Benner, S.A. and Sismour, A.M., Synthetic biology, Nature Reviews Genetics, 6(7):533-543 (2005).
Berge, S.M. et al., Pharmaceutical salts, J. Pharm. Sci., 66(1):1-19 (1997).
Besch, R. et al, Specific Inhibition of ICAM-1 Expression Mediated by Gene Targeting with Triplex-forming Oligonucleotides, J. Biol. Chem., 277(26): 32473-32479 (2002).
Bisbal, C. and Silverman, R.H., Diverse functions of RNase L and implication in pathology, Biochimie, 89(6-7):789-798 (2007).
Block, E. et al., Allium Chemistry: Synthesis and Sigmatropic Rearrangements of Alk(en)yl 1-Propenyl Disulfide S-Oxides from Cut Onion and Garlic, Journal of the Ameican Chemical Society, 118(12): 2799-2810 (1996).
Block, S.S. and Weidner, J.P, Vibrational Behavior and Structure of Disulfide Dioxides (Thiolsulfonates), Applied spectroscopy, 20(2): 71-73 (1966).
Bobkov, G.V. et al., Phosphoramidite building blocks for efficient incorporation of 2'-O-aminoethoxy(and propoxy)methyl nucleosides into oligonucleotides, Tetrahedron, 64: 6238-6251 (2008).
Bock, L.C. et al., Selections of single-stranded DNA molecules that bind and inhibit human thrombin, Nature, 355: 564-566 (1992).
Boczkowska, M. et al., Stereodefined Phosphorothioate Analogues of DNA: Relative Thermodynamic Stability of the Model PS-DNA/DNA and PS-DNA/RNA complexes, Biochemistry, 41: 12483-12487 (2002).
Bode, C. et al. CpG DNA as a vaccine adjuvant, Expert Rev. Vaccines, 10(4): 499-511 (2011).
Bodor, N. et al., A convenient synthesis of (acyloxy)alkyl .alpha.-ethers of phenols, The Journal of Organic Chemistry, 48(26):5280-5284 (1983).
Bohringer, M. et al., Why Pentose and not Hexose Nucleic Acids? Part II: Oligonucleotides of 2'3'-dideoxy-β-d-glucopyranosyl ('homo-DNA') production, Helvetica Chimica Acta, 75:1416-1477 (1992).
Bologna, J. et al., Uptake and Quantification of Intracellular Concentration of Lipophilic Pro-Oligonucleotides in HeLa Cells, Antisense and Nucleic Acid Drug Development, 12(1):33-41 (2002).
Bonora, G.M. et al., Large scale, liquid phase synthesis of oligonucleotides by the phosphoramidite approach, Nucleic Acids Research, 21(5): 1213-1217 (1993).
Boudreau, R.L. et al., Nonallele-specific silencing of mutant and wild-type huntingtin demonstrates therapeutic efficacy in Huntington's disease mice, 17(6): 1053-1063 (2009).
Braasch et al., RNA Interference in Mammalian Cells by Chemically-Modified RNA, Biochemistry 42(26): 7967-7975 (2003).
Brill, W. et al., Thioalkylation of Nucleoside-H-Phosphonates and Its Application to Solid Phase Synthesis of Oligonucleotides, Tetrahedron Letters, 36(5):703-706 (1995).
Brooks, P.C. et al., Insulin-like Growth Factor Receptor Cooperates with Integrin $\alpha v \beta 5$ to Promote Tumor Cell Dissemination in Vivo, The Journal of Clinical Investigation, 99(6)1390-1398 (1997).
Brown, J.W.S. and Simpson, C.G., Splice Site Selection in Plant Pre-mRNA Splicing, Ann. Rev. Plant Physiol. Plant Mol. Biol., 49: 77-95 (1998).
Bumcrot, D et al., RNAi therapeutics: a potential new class of pharmaceutical drugs, Nat. Chem. Biol., 2: 711-9 (2006).
Bundgaard, H., (C) Means to Enhance Penetration. (1) Prodrugs as a means to improve the delivery of peptide drugs, Advanced Drug Delivery Reviews, 8:1-38 (1992).
Bundgaard, H., Design and Application of Prodrugs, A Textbook of Drug Design and Development, Edited by Krogsgaard-Larsen, P. and Bundgaard, H., Chapter 5: 113-191 (1991).
Bundgaard, H., Design of Prodrugs, Elsevier, 7-9 and 21-24 (Chapter 1) (1985).
Bunnell. B.A. et al., Targeted Delivery of Antisense Oligonucleotides by Molecular Conjugates, Somatic Cell and Molecular Genetics, 18(6):559-569 (1992).
Burgers et al., Absolute configuration of the diastereomers of adenosine 5' -O-(1-thiaotriphosphate): Consequences for the stereochemistry of polymerization by DNA-dependent RNA polymerase from *Escherichia coli*, Proceedings of the National Academy of Sciences of the United States of America 75(10): 4798-4800 (1978).
Campbell, J. et al., Hybrid polymer/MOF membranes for Organic Solvent Nanofiltration (OSN): Chemical modification and the quest for perfection, Journal of Membrane Science, 503: 166-176 (2016).
Cankurtaran, E.S. et al., Clinical Experience with Risperidone and Memantine in the Treatment of Huntington's Disease, Journal of the National Medical Association, 98(8): 1353-1355 (2006).
Carbone, G.M. et al., Selective inhibition of transcription of the Ets2 gene in prostate cancer cells by a triplex-forming oligonucleotide, Nucl. Acid. Res., 31: 833-843 (2003).
Carrillo, H., and Lipman, D.J., The multiple sequence alignment problem in biology, SIAM J. Appl. Math., 48:1073-1082 (1988).
CAS Registry No. 1225524-67-3; STN Entry Date May 28, 2010; α-[(2-methylphenyl)methyl]-2-Pyrrolidinemethanol.

(56) References Cited

OTHER PUBLICATIONS

CAS Registry No. 1225524-68-4; STN Entry Date May 28, 2010; α-[(4-methylphenyl)methyl]-2-Pyrrolidinemethanol.
CAS Registry No. 1225545-00-5; STN Entry Date May 28, 2010; α-[(2,4,6-trimethylphenyl)methyl]-2-Pyrrolidinemethanol.
CAS Registry No. 1225554-20-0; STN Entry Date May 28, 2010; α-[(4-ethylphenyl)methyl]-2-Pyrrolidinemethanol.
CAS Registry No. 1225594-74-0; STN Entry Date May 28, 2010; α-[(2-chloro-6-fluorophenyl)methyl]-2-Pyrrolidinemethanol.
CAS Registry No. 1225682-42-7; STN Entry Date May 30, 2010; α-[(4-chlorophenyl)methyl]-2-Pyrrolidinemethanol.
CAS Registry No. 1226037-41-7; STN Entry Date May 30, 2010; α-[(3-chlorophenyl)methyl]-2-Pyrrolidinemethanol.
CAS Registry No. 1226118-97-3; STN Entry Date May 30, 2010; α-[(3-bromophenyl)methyl]-2-Pyrrolidinemethanol.
CAS Registry No. 1226119-02-3; STN Entry Date May 30, 2010; α-[(4-bromophenyl)methyl]-2-Pyrrolidinemethanol.
CAS Registry No. 1226146-65-1; STN Entry Date May 30, 2010; α-[(2,4-dimethylphenyl)methyl]-2-Pyrrolidinemethanol.
CAS Registry No. 1226160-20-8; STN Entry Date May 30, 2010; α-[(2,5-dimethylphenyl)methyl]-2-Pyrrolidinemethanol.
CAS Registry No. 1226178-36-4; STN Entry Date May 30, 2010; α-[(2-fluorophenyl)methyl]-2-Pyrrolidinemethanol.
CAS Registry No. 1226188-06-2; STN Entry Date May 30, 2010; α-[[4-(1-methylethyl)phenyl]methyl]-2-Pyrrolidinemethanol.
CAS Registry No. 1226204-20-1; STN Entry Date May 30, 2010; α-[(3-methylphenyl)methyl]-2-Pyrrolidinemethanol.
CAS Registry No. 1226231-44-2; STN Entry Date May 30, 2010; α-[(2-chlorophenyl)methyl]-2-Pyrrolidinemethanol.
CAS Registry No. 1226352-28-8; STN Entry Date May 30, 2010; α-[(2,4-dichlorophenyl)methyl]-2-Pyrrolidinemethanol.
CAS Registry No. 1226352-38-0; STN Entry Date May 30, 2010; α-[(3,4-dichlorophenyl)methyl]-2-Pyrrolidinemethanol.
CAS Registry No. 1226413-27-9; STN Entry Date May 30, 2010; α-(phenylmethyl)-2-Pyrrolidinemethanol.
CAS Registry No. 1226419-15-3; STN Entry Date May 30, 2010; α-[(4-fluorophenyl)methyl]-2-Pyrrolidinemethanol.
CAS Registry No. 1263282-82-1 ; STN Entry Date Feb. 21, 2011; (S)-[(diphenyl)methyl]-2-Pyrrolidinemethanol.
CAS RN 78-96-6, Entered STN: Nov. 16, 1984.
Chang, W. et al., Systematic chemical modifications of single stranded siRNAs significantly improved CTNNB1 mRNA silencing, Bioorg. Med. Chem. Lett., 1-5 (2016), http://dx.doi.org/10.1016/j.bmcl.2016.07.064.
Chatgilialoglu, C. and Snieckus, V., Chemical Synthesis: Gnosis to Prognosis, Kluwer Academic, 293-340 (1996).
Check, E., RNA interference: hitting the on switch, Nature, 448(7156): 855-858 (2007).
Chiu, Y. and Rana, T.M., siRNA function in RNAi: A chemical modification analysis, RNA, 9(9):1034-1048 (2003).
Cieslak, J. et al., Thermolytic 4-methylthio-1-butyl group for phosphate/thiophosphate protection in solid-phase synthesis of DNA oligonucleotides, Journal of Organic Chemistry, 69(7):2509-2515 (2004).
Clark, J.H, Flouride IOn as a Base in Organic Synthesis, Chemical Reviews, 1980 American Chemical Society 80(5): 429-452 (1980).
Communication Relating to the Results of the Partial International Search of PCT/IB2015/000395, Annex to Form PCT/ISA/206, 3 pages (dated Aug. 24, 2015).
Conway, N., The introduction of reporter groups at multiple and/or specific sites in DNA containing phosphorothioate diesters, Nucleic Acids Research, 43-44 (1989).
Cooney, M., et al., Site-Specific Oligonucleotide Binding Represses Transcription of the Human c-myc Gene in Vitro, Science, 241: 456-459 (1988).
Cosstick, R. and Eckstein, F., Synthesis of d(GC) and d(CG) Octamers Containing Alternating Phosphorothioate Linkages: Effect of the Phosphorothioate Group on the B-Z Transition, Biochemistry, 24: 3630-3638 (1985).
Coughlin, J.E. et al., Orally bioavailable anti-HBV dinucleotide acyloxyalkyl prodrugs, Bioorganic and Medicinal Chemistry Letters, 20(5):1783-1786 (2010).
Cox, J.R. and Ramsay, O.B., Mechanisms of Nucleophilic Substitution in Phosphate Esters, Chemical Reviews, 64(4): 317-352, (1964).
Crary, S.M. et al., Specific phosphorothioate substitutions probe the active site of Bacilus subtilis ribonuclease P, RNA, 8:933-947 (2002).
Crooke, S.T. and Geary, R.S. Clinical pharmacological properties of mipomersen (Kynamro), a second generation antisense inhibitor of apolipoprotein B, Br. J. Clin. Pharmacol., 76: 269-276 (2012).
Crooke, S.T., Molecular mechanisms of action of antisense drugs, Biochemica et Biophysica Acta, 1489: 31-44 (1999).
Cullen, K.A. et al., Ambulatory surgery in the United States, 2006, National Health Statistics Reports, 11:1-28 (Jan. 28, 2009—Revised Sep. 4, 2009).
Current Protocols in Nucleic Acid Chemistry, Edited by Beaucage, S.L. et al., Chapter 2: Protection of Nucleosides for Oligonucleotide Synthesis, 2.0.1.-2.16.31 (2012).
Davis, B.G. et al., Altering the specificity of subtilisin bacillus lentus through the introduction of positive charge at single amino acid sites, Bioorganic & Medicinal Chemistry, 7(11): 2303-2311 (1999).
De Koning, M.G. et al., Simple and Efficient Solution-Phase Synthesis of Oligonucleotides Using Extractive Work-Up, Organic Process Research & Developmen, 10: 1238-1245 (2006).
DeLeavey, G.F. and Damha, M.J., Designing chemically modified oligonucleotides for targeted gene silencing. Chem. Biol., 19: 937-54 (2012).
Dellinger, D.J. et al., Streamlined Process for the Chemical Synthesis of RNA Using 2'-O-Thionocarbamate-Protected Nucleoside Phosphoramidites in the Solid Phase, J. Am. Chem. Soc., 133: 11540-11556 (2011).
Devereux, J. et al., A comprehensive set of sequence analysis programs for the VAX, Nucleic Acids Research, 12(1):387-395 (1984).
Dietz, G.P.H. et al., Delivery of bioactive molecules into the cell: The Trojan horse approach, Molecular and Cellular Neuroscience, 27(2): 85-131 (2004).
Djukanovic, R. et al., Mucosal Inflammation in Asthma, Am. Rev. Respir. Dis., 142: 434-457 (1990).
Documents submitted to and/or received from the United States Securities and Exchange Commission; downloaded from Edgar (Feb. 2, 2015 to Dec. 10, 2015).
Documents submitted to and/or received from the United States Securities and Exchange Commission; downloaded from EDGAR (Dec. 17, 2015 to Oct. 4, 2016).
Dorman et al., Synthesis of Oligodeoxynucleotides and Oligodeoxynucleotide Analogs using Phosphoramidite Intermediates, Tetrahedron, 40(1):95-102 (1984).
Dua, P. et al., Patents on SELEX and therapeutic aptamers, Recent Patents on DNA & Gene Sequences, 2(3):172-186 (2008).
Eaton, W.A. et al., Submillisecond kinetics of protein folding, Curr. Opin. Chem. Biol., 1:10-14 (1997).
Eckstein, F. et al., Stereochemistry of polymerization by DNA-dependent RNA-polymerase from *Escherichia coli*: an investigation with a diastereomeric ATP-analogue, Proc. Natl. Acad. Sci. USA, 73: 2987-90 (1976).
Eckstein, F. Phosphorothioates, Essential Components of Therapeutic Oligonucleotides, Nucleic Acid Therapeutics, 1-14 (2014).
Eckstein, F., Oligonucleotides and Analogues a Practical Approach, IRL Press, 1-24 (1991).
Egli, M. et al., Crystal structure of homo-DNA and nature's choice of pentose over hexose in the genetic system, Journal of the American Chemical Society, 128(33):10847-56 (2006).
Egli, M. et al., Probing the Influence of Stereoelectronic Effects on the Biophysical Properties of Oligonucleotides: Comprehensive Analysis of the RNA Affinity, Nuclease Resistance, and Crystal Structure of Ten 2'-0-Ribonucleic Acid Modifications, Biochemistry, 44: 9045-9057 (2005).

(56) References Cited

OTHER PUBLICATIONS

El Harchaoui, K. et al., Current and future pharmacologic options for the management of patients unable to achieve low-density lipoprotein-cholesterol goals with statins, Am. J. Cardiovasc. Drugs, 8(4): 233-242 (2008).
Elbashir, S.M. et al., Duplexes of 21-nucleotide RNAs mediate RNA interference in cultured mammalian cells, Nature, 411: 494-498 (2001).
Elbashir, S.M. et al., Functional anatomy of siRNAs for mediating efficient RNAi in *Drosophila melanogaster* embryo lysate, The EMBO Journal, 20(23): 6877-6888 (2001).
Ellington, A.D. and Szostak, J.W., In vitro selection of RNA molecules that bind specific ligands, Nature, 346: 818-822 (1990).
Engelhardt, J.A. et al., Scientific and Regulatory Policy Committee Points-to-consider Paper: Drug-induced Vascular Injury Associated with Nonsmall Molecule Therapeutics in Preclinical Development: Part 2. Antisense Oligonucleotides, Toxicologic Pathology, XX: 1-10 (2015).
Epton, R., Innovation and Perspectives in Solid Phase Synthesis, Peptides, Proteins and Nucleic Acids, 21:157-162 (1994).
Eschenmoser, A. et al., Why pentose- and not hexose-nucleic acids? Introduction to the problem, conformational analysis of oligonucleotide single strands containing 2', 3'-dideoxyglucopyranosyl building blocks ('homo-DNA'), and reflections on the conformation of A-and B-DNA, Helvetica Chimica Acta, 75:218-259 (1992).
Eschenmoser, A., Chemical etiology of nucleic acid structure, Science, 284(5423):2118-24 (1999).
Eschenmoser, A., Towards a Chemical Etiology of the Natural Nucleic Acids' Structure, Chemical Synthesis, Edited by Chatgilialoglu, C. and Snieckus, V., Kluwer Academic Publishers, 293-340 (1996).
Famulok, M. Oligonucleotide aptamers that recognize small molecules, Curr. Opin. Struct. Biol., 9: 324-329 (1999).
Fendrich et al., Determination of the Absolute P-configuration of a Phthalidyl$_L$Phosphonate Thymidine-Thymidine Dimer, Nucleosides Nucleotides Nucleic Acids., 22(5-8): 1127-1129.
Ferreira, F. et al., Lewis acid deprotection of silyl-protected oligonucleotides and base-sensitive oligonucleotide analogues, Tetrahedron Letters, 45(33):6287-6290 (2004).
File Registry on STN, RN 18217-60-2, Entered STN: Nov. 16, 1984.
File Registry on STN, RN 871246-91-2, Entered STN: Jan. 5, 2006.
Fire, A. et al., Potent and specific RNA interference by double-stranded RNA in Caenorhadbditis elegans, Nature, 391: 806-811 (1998).
Forster, A.C. and Symons, R.H. Self-cleavage of plus and minus RNAs of a virusoid and a structural model for the active sites, Cell, 49(2): 211-220 (1987).
Forster, A.C. and Symons, R.H. Self-Cleavage of Virusoid RNA is performed by the Proposed 55-Nucleotide Active Site, Cell, 50: 9-16 (1987).
Frank-Kamenetsky, M. et al., Therapeutic RNAi targeting PCSK9 acutely lowers plasma cholesterol in rodents and LDL cholesterol in nonhuman primates. Proc. Natl. Acad. Sci. USA., 105(33): 11915-11920 (2008).
Frazier, K. et al., Potential Mechanisms of vascular toxicity in Monkeys with antisense oligonucleotides, TIDES oligo conference, 1-25 (May 15, 2014).
Frazier, K.S. Antisense Oligonucleotide Therapies: The Promise and the Challenges from a Toxicologic Pathologist's Perspective, Toxicology Pathology, 43: 78-89 (2015).
Frederiksen, J.K. et al., Separation of RNA Phosphorothioate Oligonucleotides by HPLC, Methods of Enzymology, 468:289-309 (2009).
Freier, S.M. et al., Improved free-energy parameters for predictions of RNA duplex stability, Proc. Nat. Acad. Sci. USA, 83: 9373-9377 (1986).
Froehler, B.C. et al., Synthesis of DNA via deoxynucleoside H-phosphonate intermediates, Nucleic Acids Research, 14(13): 5399-5407 (1986).

Fujii et al., Acylphosphonates. 5.1A new method for stereospecific generation of phosphorothioate via aroylphosphonate intermediate, Tetrahedron Letters, 27(8): 935-938 (1986).
Fujii et al., Acylphosphonates. 7.1 A New Method for Stereospecific and Stereoselective Generation of Dideoxyribonucleoside Phosphorothioates via the Acylphosphonate Intermediates, Tetrahedron, 43: 3395-3407 (1987).
Gaffney, P.R.J. et al., Liquid-Phase Synthesis of 2'-Methyl-RNA on a Homostar Support through Organic-Solvent Nanofiltration, Chem. Eur. J., 21:1-10 (2015).
Ganguly, A.K. et al., Structure of Halomicin B, J.C.S. Chem. Comm., 395-396 (1974).
Garegg, P.J. et al., Nucleoside H-Phosphonates. III. Chemical Synthesis of Oligodeoxyribonucleotides by the Hydrogenphosphonate Approach, Tetrahedron Letters, 27(34): 4051-4054 (1986).
Gauglitz, G.G. et al., Hypertrophic Scarring and Keloids: Pathomechanisms and Current Emerging Treatment Strategies, Mol. Med., 17(1-2): 113-125 (2011).
Gijsen, H.J.M et al., Development of two diastereoselective rougtes towards trans-4-aminomethyl-piperidin-3-ol building blocks, Tetrahedron 64(10): 2456-2464 (2008).
Goraczmiak, R. et al., Gene silencing by synthetic U1 Adaptors, Nature Biotechnology 27(3): 257-263 (2008).
Gosselin, G. et al., New insights regarding the potential of the pronucleotide approach in antiviral chemotherapy, 43(1)195-208 (1996).
Gough, G.R. et al., Recovery and recycling of synthetic units in the construction of oligodeoxyribonucleotides on solid supports, Tetrahedron Letters, 22(42): 4177-4180 (1981).
Gould, W.A. et al., Pyrrolidines IX. 3-Aryl-3-pyrrolidinols, Journal of Medicinal Chemistry, 7(1): 60-67 (1964).
Graham, M.J. et al., Antisense inhibition of proprotein convertase subtilisin/kexin type 9 reduces serum LDL in hyperlipidemic mice, J. Lipid Res., 48(4): 763-767 (2007).
Grajkowski, A. et al., Design and Development of Thermolytic DNA Oligonucleotide Prodrugs, Annals of the New York Academy of Sciences, 1058:26-38 (2005).
Grajkowski, A. et al., Solid-Phase Synthesis of Thermolytic DNA Oligonucleotides Functionalized with a Single 4-Hydroxy-1-butyl or 4-Phosphato-/Thiophosphato-1-butyl Thiophosphate Protecting Group, Journal of Organic Chemistry, 72(3): 805-815 (2007).
Grajkowski, A. et al., Thermolytic CpG-containing DNA oligonucleotides as potential immunotherapeutic prodrugs, Nucleic Acids Research, 33(11):3550-3560 (2005).
Green, L.S. et al., Inhibitory DNA Ligands to Platelet-Derived Growth Factor B-Chain, Biochemistry, 35: 14413-14424 (1996).
Green, L.S. et al., Nuclease-resistant nucleic acid ligands to vascular permeability factor/vascular endothelial growth factor, Chem. Biol., 2(10): 683-695 (1995).
Griffiths-Jones, S. et al., miRBase: microRIVA sequences, targets and gene nomenclature, Nucleic Acids Research, 34 (Database Issue): D140-D144 (2006).
Griffiths-Jones, S. The microRNA Registry, Nucleic Acids Research, 32 (Database Issue): D109-D111 (2004).
Groebke, K. et al., Why pentose and not hexose nucleic acids? Part V. Purine-purine pairing in homo-DNA: guanine, isoguanine, 2,6-diaminopurine and xanthine. Helvetica Chimica Acta. 81: 375-474 (1998).
Gude, L. et al., Mapping Targetable Sites on Human Telomerase RNA Pseudoknot/Template Domain Using 2'-OMe RNA-interacting Polynucleotide (RIPtide) Microarrays, J. Biol. Chem., 287(22): 18843-18853 (2012).
Guerciolini, R., Allele-selective Silencing of Mutant Huntingtin by Stereopure Oligonucleotides, WAVE Life Sciences, Huntington's Disease Society of America, HDSA Presentation 2016 (Jun. 3, 2016).
Guerlavais-Dagland, T et al., Fluoride-labile protecting groups for the synthesis of base-sensitive methyl-SATE oligonucleotide prodrugs, European Journal of Organic Chemistry, 2003(12):2327-2335 (2003).
Guga et al., Oxathiaphospholane Approach to the Synthesis of P-Chiral, Isotopomeric Deoxy(ribonucleoside phosphorothioate)s and Phosphates Labeled with an Oxygen Isotope. Angew Chem., 113(3): 630-633 (2001).

(56) References Cited

OTHER PUBLICATIONS

Guga et al., Unusual Thermal Stability of RNA/[RP-PS]-DNA/RNA Triplexes Containing a Homopurine DNA Strand, Biophys J., 92(7): 2507-2515 (2007).
Guga, P. and Stec, W.J., Synthesis of Phosphorothioate Oligonucleotides with Stereodefined Phsphorothioate Linkages, Current Protocols in Nucleic Acid Chemistry, Unit 4.17: 4.17.1-4.17.28 (2003).
Guga, P., P-chiral oligonucleotides in biological recognition processes, Current Topics in Medicinal Chemistry, 7:695-713 (2007).
Guo, M. et al., Solid-phase stereoselective synthesis of 2'-0-methyl-oligo-ribonucleoside phosphorothioates using nucleoside bicyclic oxazaphospholidines, Biorganic & Medicinal Chemistry Letters, 8(18):2539-2544 (1998).
Guzaev, A.P., Reactivity of 3H-1,2,4-dithiazole-3-thiones and 3H-1,2-dithiole-3-thiones as sulfurizing agents for oligonucleotide synthesis, Tetrahedron Letters, 52: 434-437 (2011).
Hacia, J.G. et al., Phosphorothioate oligonucleotide-directed triple helix formation, Biochemistry, 33:5367-5369 (1994).
Hammond, S.M. and Wood, M.J. Genetic therapies for RNA mis-splicing diseases, Trends Genet., 27: 196-205 (2011).
Hanagata, N., Structure-dependent immunostimulatory effect of CpG oligodeoxynucleoties and their delivery system, Int. J. Nanomedicine, 7: 2181-95 (2012).
Hansen et al., Azaribofuranoside Analogues as Designed Inhibitors of Purine Nucleoside Phosphorylase, Synthesis and Biological Evaluation, Acta Chemis Scandinavica 52: 1214-1222 (1998).
Harper, S.Q. et al., RNA interference improves motor and neuropathological abnormalities in a Huntington's disease mouse model, Proc. Natl. Acad. Sci. USA, 102(16): 5820-5825 (2005).
Hartmann, B. et al., Sequence effects on energetic and structural properties of phosphorothioate DNA: a molecular modelling study, Nucleic Acids Research, 27(16): 3342-3347 (1999).
Hartmann, G. et al., Delineation of a CpG Phosphorothioate Oligodeoxynucleotide for Activating Primate Immune Responses In Vitro and In Vivo, The Journal of Immunology, 164(3): 1617-1624 (2000).
Hau, P. et al., Results of G004, a phase lib actively controlled clinical trial with the TGF-b2 targeted compound AP 12009 for recurrent anaplastic astrocytoma, Journal of Clinical Oncology, 2006 ASCO Annual Meeting Proceedings (Post-Meeting Edition), 24(Jun. 20, 2018 Supplement): 1566 (2006).
Hayashi, S. et al., Studies on Antitumor Substances, Chemical & Pharmaceutical Bulletin, 12(11): 1271-1276 (1964).
Heger, W. et al., Embryotoxic effects of thalidomide derivatives on the non-human primate Callithrix jacchus; 3. Teratogenic potency of the EM 12 enantiomers, Arch. Toxicol., 62: 205-208 (1988).
Henry, A.A. and Romesberg, F.E., Beyond A, C, G and T: augmenting nature's alphabet, Current Opinion in Chemical Biology, 7(6): 727-733 (2003).
Henry, S.P. et al., Activation of the Alternative Pathway of Complement by a Phosphorothioate Oligonucleotide: Potential Mechanism of Action, The Journal of Pharmacology and Experimental Therapeutics, 281(2): 810-816 (1997).
Herbert, B-S. et al., Nonradioactive detection of telomerase activity using the telomeric repeat amplification protocol, Nat. Protoc., 1(3): 1583-1590 (2006).
Herdewijn, Oligonucleotide Synthesis, Methods in Molecular Biology, 288: 1-435 (2005).
Heuberger, B.D. and Switzer, C., A Pre-RNA Candidate Revisited: Both Enantiomers of Flexible Nucleoside Triphosphates are DNA Polymerase Substrates, Journal of the American Chemical Society, 130(2):412-413 (2008).
Higuchi, T. et al., Pro-drugs as Novel Delivery Systems, ACS Symposium Series, 14 (1975).
Hirao, I., Unnatural base pair systems for DNA/RNA-based biotechnology, Current Opinion in Chemical Biology,10:622-627 (2006).
Hohjoh, H., Disease-Causing Allele-Specific Silencing by RNA Interference, Pharmaceuticals, 6: 522-535 (2013).
Hunziker, J. et al., Why Pentose-and Not Hexose-Nucleic Acids? Part III. Oligo(2',3'-dideoxy-β-D-glucopyranosyl)nucleotides. ('Homo-DNA'): Base-Pairing Properties, Helvetica Chimica Acta, 76(1):259-352 (1993).
Inagawa, T. et al., Inhibition of human immunodeficiency virus type 1 replication by P-stereodefined oligo(nucleoside phosphorothioate)s in a long-term infection model, FEBS Letters, 528(1-3): 48-52 (2002).
International Preliminary Report on Patentability for PCT/JP2013/069107, 10 pages (dated Jan. 15, 2015).
International Preliminary Report on Patentability and Written Opinion of the Searching Authority for PCT/JP2011/055018 (dated Oct. 11, 2012) with English Translation thereof.
International Preliminary Report on Patentability for Application No. PCT/JP2010/065900, 6 pages (dated Mar. 29, 2012).
International Preliminary Report on Patentability for Application No. PCT/JP2010/065900, 7 pages (dated Apr. 19, 2012). (English Translation).
International Preliminary Report on Patentability for Application No. PCT/JP2011/071559, 7 pages (dated Apr. 25, 2014).
International Preliminary Report on Patentability for PCT/JP2013/004303, 1 page (dated Jan. 13, 2015).
International Search Report for PCT/IB2009/007923, 4 pages (dated Sep. 6, 2010).
International Search Report for PCT/IB2015/000395, 7 pages (dated Oct. 30, 2015).
International Search Report for PCT/JP11/71559, 3 pages (dated Dec. 20, 2011).
International Search Report for PCT/JP15/50716 and English Translation, 8 pages (dated Apr. 21, 2015).
International Search Report for PCT/JP2010/065900, 1 page (dated Sep. 15, 2010).
International Search Report for PCT/JP2011/077313, 2 pages (dated Jan. 10, 2012).
International Search Report for PCT/JP2011/55018 (dated Mar. 29, 2011).
International Search Report for PCT/JP2013/004303, 3 pages (dated Aug. 13, 2013).
International Search Report for PCT/JP2015/050714, and English Translation, 8 pages (dated Apr. 21, 2015).
International Search Report for PCT/JP2015/050718 and English Translation, 8 pages (dated Apr. 21, 2015).
International Search Report for PCT/US2010/041068, 1 page (dated Sep. 1, 2010).
International Search Report for PCT/US2011/064287, 2 pages (dated Apr. 12, 2012).
International Search Report for PCT/US2012/046805, 2 pages (dated Sep. 19, 2012).
International Search Report for PCT/US2013/050407, 5 pages (dated Jan. 9, 2014).
International Search Report for PCT/US2016/043542, 6 pages (dated Dec. 28, 2016).
International Search Report for PCT/US2016/043598, 4 pages (dated Nov. 28, 2016).
International Search Report of PCT/JP2013/069107, 2 pages (dated Oct. 1, 2013).
Isis Pharmaceuticals, Intellectual Property: Capturing Value From Innovation, Isis' Annual Meeting of Stockholders and Open House, Intellectual Property Poster, 1 page (2011). Received from Internet <http://www.isispharm.com/Site_Gfx/pdf/11-AnMtg_IntellectualProperty_TAB.pdf>.
Isis Pharmaceuticals, Intellectual Property: Capturing Value From Innovation, Isis' Annual Meeting of Stockholders and Open House, Intellectual Property Poster, 1 page (2012). Received from Internet <http://www.isispharm.com/Site_Gfx/pdf/2012_Annual_Meeting_IP_Poster.pdf>.
Iwamoto et al., Stereocontrolled Synthesis of H-phosphonate DNA, Nucleic Acids Symposium Series, (50):159-60 (2006).
Iwamoto, N. et al., Optimization of Therapeutic Phosphorothioate Oligonucleotides by P-Chirality Control, WAVE Life Sciences, PSJ Congress: The Pharmaceutical Society of Japan, (Mar. 25, 2015-Mar. 28, 2016).

(56) References Cited

OTHER PUBLICATIONS

Iwamoto, N. et al., Stereocontrolled solid-phase synthesis of oligonucleoside H-phosphonates by an oxazaphospholidine approach, Angewandte Chemie International Edition, 48(3):496-499 (2009).
Iyer, R.P. et al., A novel nucleoside phosphoramidite synthon derived from 1R, 2S-ephedrine, Tetrahedron Asymmetry 6(5)1051-1054 (1995).
Iyer, R.P. et al., Acyloxyaryl prodrugs of oligonucleoside phosphorothioates, Bioorganic and Medicinal Chemistry Letters, 6(16):1917-1922 (1996).
Iyer, R.P. et al., Bioreversible oligonucleotide conjugates by site-specific derivatization, Bioorganic and Medicinal Chemistry Letters, 7:871-876 (1997).
Iyer, R.P. et al., Stereospecific Bio-Reversibility of Dinucleoside S-Alkyl Phosphorothiolates to Dinucleoside Phosphorothioates, Bioorganic & Medicinal Chemistry Letter, 4(20):2471-2476 (1994).
Iyer, R.P., et al., 3H-1,2-Benzodithiole-3-one 1,1-Dioxide as an Improved Sulfurizing Reagent in the Solid-Phase Synthesis of Oligodeoxyribonucleoside Phosphorothioates, Journal of the American Chemical Society, 112(3):1253-1254 (1990).
Iyer, R.P., et al., Prodrugs of Oligonucletides: The Acyloxyalkyl Esters of Oligodeoxyribonucleoside Phosphorothioates, Bioorganic Chemistry, 23:1-21 (1995).
Iyer, R.P., et al., Solid-phase stereoselective synthesis of oligonucleoside phosphorothioates: The nucleoside bicyclic oxazaphospholidines as novel synthons, Tetrahedron Letters, 39:2491-2494 (1998).
Jahns, H., et al., Stereochemical bias introduced during RNA synthesis modulates the activity of phosphorothioate siRNAs, Nat. Commun., 6: 6317 (2015).
Jiang, J. et al., Allele-Specific Silencing of Mutant Myh6 Transcripts in Mice Suppresses Hypertrophic Cardiomyopathy, Science, 342: 111-114 (2013).
Jin et al., A Stereoselective Synthesis of Dinucleotide Boranophosphate, Using Chiral Indole-Oxazaphosphorine Intermediates, Tetrahedron Letters, 39: 6433-6436 (1998).
Jin et al., Stereoselective Synthesis of Dithymidine Phosphorothioates Using Xylose Derivatives as Chiral Auxiliaries, J. Org. Chem., 63(11): 3647-3654 (1998).
Johansson et al., Studies towards synthesis of dinucleoside arylphosphonates with metal complexing properties, Nucleosides Nucleotides & Nucleic Acids, 22(5-8): 1459-61 (2003).
Johansson et al., Synthesis of dinucleoside pyridylphosphonates involving palladium(o)-catalysed phosphorus-carbon bond formation as a key step, Chem. Commun., 2564-2565 (2001).
Johansson et al., The case for configurational stability of H-phosphonate diesters in the presence of diazabicyclo[5.4.0]undec-7-ene (DBU), Bioorg Med Chem., 9(9): 2315-22 (2001).
Jopling, C.L. et al., Modulation of Hepatitis C Vicus RNA Abundance by a Liver-Specific MicroRNA, Science, 309: 1577-1581 (2005).
Joyce, G.F. et al., The case for an ancestral genetic system involving simple analogues of the nucleotide, Proceedings of the National Academy of Sciences, 84:4398-4402 (1987).
Joyce, G.F. The antiquity of RNA-based evolution, Nature, 418(6894): 214-221 (2002).
Kakeya, N. et al., Studies on Prodrugs of Cephalosporins. I. Synthesis and Biological Properties of Glycyloxybenzoyloxymethyl and Glycylaminobenzoyloxymethyl Esters of 7-[2-(2-Aminothiazol-4-yl)-(Z)-2-methoiminoacetamido]-3-methyl-3-cephem-4-carboxylic Acid, Chem. Pharm. Bull., 32(2): 692-698 (1984).
Kamada, A.K. et al., Issues in the Use of Inhaled Glucocorticoids, Am. J. Respir. Crit. Care. Med., 153: 1739-1748 (1996).
Karwowski, B. et al., Stereocontrolled Synthesis of LNA Dinucleoside Phosphorothioate by the Oxathiaphospholane Approach, Bioorganic & Medicinal Chemistry Letters, 11: 1001-1003 (2001).
Kaur, H. et al., Activation of natural killer-like YT-INDY cells by oligodeoxynucleotides and binding by homologous pattern recognition proteins, Scandinavian Journal of Immunology, 62: 361-370 (2005).

Kawasaki, A et. al., Uniformly Modified 2'-Deoxy-2'-fluoro Phosphorothioate Oligonucleotides as Nuclease-Resistant Antisense Compounds with High Affinity and Specificity for RNA Targets, J. Med. Chem., 36: 831-841 (1993).
Kay, C. et al., Huntingtin Haplotypes Provide Prioritized Target Panels for Allele-Specific Silencing in Huntington Disease Patients of European Ancestry, Molecular Therapy, Accepted.
Kay, C. et al., Huntingtin Haplotypes Provide Prioritized Target Panels for Allele-specific Silencing in Huntington Disease Patients of European Ancestry, The American Society of Gene & Cell Therapy, 1-13 (2015).
Kers et al., A new type of nucleotide analogue with 4-pyridylphosphonate internucleotide linkage, Tetrahedron Letters, 40(22): 4263-4266 (1999).
Kihara, M et al., New norepinephrine potentiators: synthesis and structure-actvity relastionships of a series of 4-phenyl-1,2,3,4-tetrahydroisoquinolin-4-ols, Chemical & Pharmaceutical Bulletin 42(1): 67-73 (1994).
Kim, D. et al., Immunostimulation and anti-DNA antibody production by backbone modified CpG-DNA, Biochemical and Biophysical Research Communicationes, 379: 362-367 (2009).
Kim, M., Beta conformation of polyglutamine track revealed by a crystal structure of Huntingtin N-terminal region with insertion of three histidine residues, Prion, 7(3): 221-228 (2013).
Kim, N.W. et al., Specific Association of Human Telomerase Activity with Immortal Cells and Cancer, Science, 226: 2011-2015 (1994).
Kim, S-H. and Cech, T.R., Three-dimensional model of the active site of the selfsplicing rRNA precursor of Tetrahymena, Proc. Natl. Acad. Sci. U S A., 84(24): 8788-8792 (1987).
Kim, S. et al., Liquid-Phase RNA Synthesis by Using Alkyl-Chain-Soluble Support, Chem. Eur. J., 19: 8615-8620 (2013).
Kiviniemi, A. et al., Solid-Supported 2'-O-Glycoconjugation of Oligonucleotides by Azidation and Click Reactions, Bioconjugate Chemistry, 22(6): 1249-1255 (2011).
Klose, J. et al., Preparation of 2-(2-Cyanoethyl)-sulfanyl-1H-isoindole-1,3-(2H)-dione and related sulfur transfer reagents, Tetrahedron, 53(42):14411-14416 (1997).
Kool, E.T., Replacing the Nucleobases in DNA with Designer Molecules, Accounts of Chemical Research, 35:936-943 (2002).
Kordasiewicz, H.B. et al., Sustained therapeutic reversal of Huntington's disease by transient repression of huntingtin synthesis, Neuron, 74(6): 1031-1044 (2012).
Kozikowski, A.P. et al., Chemistry of the main group metals: A stereoselective synthesis of allyl vinyl thioethers for the thio-claisen reaction, Journal of Organometallic Chemistry, 164(3): C33-C37 (1979).
Koziolkewicz et al., Stability of Stereoregular Oligo-(nucleoside Phosphorothioate)s in Human Plasma: Diastereoselectiviy of Plasma 3'-Exonuclease, Antisense Nucl. Acid Drug Dev., 7: 43-48 (1997).
Koziolkewicz et al., Stereodifferentiation-the effect of P chirality of oligo(nucleoside phosphorothioates) on the activity of bacterial RNase H, Nucl. Acids Res., 23(24): 5000-5005 (1995).
Koziolkiewicz, M. et al., Effect of P-chirality of oligo(deoxyribonucleoside phosphorothioate)s) on the activity of terminal deoxyribonucleotidyl transferase, FEBS Letters, 434(1-2): 77-82 (1998).
Kraszewski et al., Studies on Reactions of Nucleoside H-phosphonates with Bifunctional Reagents. Part 1. Reaction with amino alcohols, J. Chem. Soc., Perkin Trans., 1: 1699-1704 (1993).
Kremer, B. et al., A Worldwide Study of the Huntington's Disease Mutation, The New England Journal of Medicine, 330(20): 1401-1406 (1994).
Krieg, A.M. et al., CpG motifs in bacterial DNA trigger direct B-cell activation, Nature, 374: 546-549 (1995).
Krieg, A.M. et al., P-Chirality-Dependent Immune Activiation by Phosphorothioate CpG Oligodeoxynucleotides, Oligonucleotides, 13:491-499 (2003).
Krieg, A.M., Development of TLR9 agonists for cancer therapy, The Journal of Clinical Article Preview Online (Jul. 23, 2015).
Krueger, A.T. et al., Synthesis and properties of size-expanded DNAs: toward designed, functional genetic systems, Accounts of Chemical Research, 40:141-150 (2007).

(56) References Cited

OTHER PUBLICATIONS

Krutzfeldt, J. et al., Silencing of microRNAs in vivo with 'antagomirs', Nature, 438: 685-689 (2005).

Kungurtsev, V. et al., Solution-Phase Synthesis of Short Oligo-2'-deoxyribonucleotides by Using Clustered Nucleosides as a Soluble Support, Eur. J. Org. Chem., 6687-6693 (2013).

Kuramoto, Y. et al., Mannosylated cationic liposomes/CpG DNA complex for the treatment of hepatic metastasis after intravenous administration in mice, Journal of Pharmaceutical Science, 98(3): 1193-1197 (2009).

Kwon, H-J. et al., NF-kappaB-dependent regulation of tumor necrosis factor-alpha gene expression by CpG-oligodeoxynucleotides, Biochem. Biophys. Res. Commun., 311(1): 129-138 (2003).

LaPlanche, L.A. et al., Phosphorothioate-modified oligodeoxyribonucleotides. III. NMR and UV spectroscopic studies of the Rp-Rp, Sp-Sp, and Rp-Sp duplexes, [d(GGsAATI'CC)2, derived from diastereomeric 0-ethyl phosphorothioates, Nucleic Acids Research, 14(22): 9081-9093 (1986).

Latimer, L.J.P. et al, Synthetic repeating sequence DNAs containing phosphorothioates: nuclease sensitivity and triplex formation, Nucleic Acids Research, 17(4): 1549-1561 (1989).

Laurent et al., Chiral and steric effects in the efficient binding of alpha-anomeric deoxyoligonucleoside N-alkylphosphoramidates to ssDNA and RNA, Nucleic Acids Res., 27(21): 4151-9 (1999).

Lavergne, T. et al., A Base-Labile Group for 2'-OH Protection of Ribonucleosides: A Major Challenge for RNA Synthesis, Chem. Eur. J, 14, 9135-9138 (2008).

Lesnikowski et al., Studies on Stereospecific Formation of P-Chiral Internucleotide Linkage. Synthesis of (RP, RP)- and (SP, SP)-Thymidylyl (3', 5') Thymidylyl (3', 5') Thymidine DI (O,O-Phosphorothioate) Using 2-Nitrobenzyl Group as a New S-Protection, Tetrahedron Letters 30(29) 3821-3824 (1989).

Lesnikowski, Z. J. et al., Octa(thymidine methanephosphonates) of partially defined sterochemistry: synthesis and effect of chirality at phosphorus on binding to pentadecadeoxyriboadenylic acid, Nucleic Acids Research, 18(8): 2109-2115 (1990).

Levin, A.A. et al., Basic Principles of the Pharmacokinetics of Antisense Oligonucleotide Drugs, Antisense Drug Technology: Principles, Strategies, and Applications, Second Edition, Chapter 7: 183-215 (2008).

Li L.C., Small RNA Mediated Gene Activation, RNA and the Regulation of Gene Expression: A Hidden Layer of Complexity, Edited by Kevin V. Morris, Chapter 13, Caister Academic Press (2008).

Li, L-C. et al., Small dsRNAs induce transcriptional activation in human cells, PNAS, 103(46): 17337-17342 (2006).

Li-Tsang, C.W. et al., Prevalence of hypertrophic scar formation and its characteristics among the Chinese population, Burns, 31: 610-616 (2005).

Liang, X-h. et al., Identification and characterization of intracellular proteins that bind oligonucleotides with phosphorothioate linkages, Nucleic Acids Research, 43(5): 2927-2945, Supplemental Data pp. 1-20 (2015).

Lima, W. et al., Single-Stranded ssRNAi Activate RNAi in Animals, Cell, 150: 883-894 (2012).

Lima, W.F. et al., The influence of antisense oligonucleotide-induced RNA structure on *Escherichia coli* RNase H1 activity, J. Biol. Chem., 272(29):18191-9 (1997).

Lima, W.F., et al., Human RNase H1 discriminates between subtle variations in the structure of the heteroduplex substrate, Mol. Pharmacol., 71: 83-91 (2007).

Limbach, P.A. et al., Summary: the modified nucleosides of RNA, Nucleic Acids Research, 22(12):2183-2196 (1994).

Lin et al., Synthesis and resolution of dinucleotide (TpAZT) phosphoramidates, Synthetic Commun., 33(14): 2553-2562 (2003).

Linton, M.F., et al., Transgenic Mice Expressing High Plasma Concentrations of Human Apolipoproteins B100 and Lipoprotein (a), J. Clin. Invest., 92: 3029-37 (1993).

Liu, W. et al., Increased Steady-State Mutant Huntingtin mRNA in Huntington's Disease Brain, Journal of Huntington's Disease 2: 491-500 (2013).

Lu, X. et al., Antisense-Mediated Inhibition of Human Immunodeficiency Virus (HIV) Replication by Use of an HIV Type 1-Based Vector Results in Severely Attenuated Mutants Incapable of Developing Resistance, Journal of Virology, 78(13): 7079-7088 (2004).

Lu, Y. and Just, G., Stereoselective synthesis of dithymidine phosphorothioates using d-xylose derived chiral auxiliaries, Tetrahedron, 57(9):1677-1687 (2001).

Lu, Y. et al., Stereoselective Synthesis of R(P)- and S(P)-Dithymidine Phosphorothioates via Chiral Indolooxazaphosphorine Intermediates Derived from Tryptophan This work was financially supported by Natural Science and Engineering Research Council of Canada (NSERC). We thank Nadim Saadeh and Dr. Orval Mamer, McGill University biomedical mass spectroscopy unit, for recording mass spectra, Angewandte Chemie International Edition, 39(24):4521-4524 (2000).

Lu, Y., Recent advances in the stereocontrolled synthesis of antisense phosphorothioates, Mini Reviews in Medicinal Chemistry, 6(3): 319-330 (2006).

Machine Translation of JP 2010-265304 (2010). <http://dossier1.ipdl.inpit.go.jp/AIPN/odse_top_dn.ipdl?NOOOO=7400>.

Machytka et al., Extension of the Applicability of &I-Values for the Configurational Assignment of Diastereomeric Phosphate-Modified Dideoxynucleotides, Nucleosides and Nucleotides, 17(12): 2311-2322 (1998).

Machytka et al., Synthesis and NMR characterization of diastereomeric CPSMeG derivatives, Nucleosides Nucleotides Nucleic Acids., 19(5-6): 903-15 (2000).

Maher III, L.J., et al., Inhibition of DNA Binding Proteins by Oligonucleotide-Directed Triple Helix Formation, Science, 245: 725-730 (1989).

Mann, M.J. et al., Therapeutic applications of transcription factor decoy oligonucleotides, J. Clin. Invest., 106:1071-1075 (2000).

Mannironi, C. et al., In Vivo Selection of Dopamine RNA Ligands, Biochemistry, 36: 9726-9734 (1997).

Martin, P., A New Access to 2'-O-alkylated Ribonucleosides and Properties of 2'-O-Alkylated Oligoribonucleotides, Helv. Chim. Acta., Abstract Only, 78: 486-504 (1995).

Martin, P., Stereoselective Synthesis of 2'-O-(2-Methoxyethyl)ribonucleosides: Neighboring-Group Participation of the Methoxyethoxy Group in the Ribosylation Step, Hely. Chim. Acta, 79: 1930-1938 (1996).

Masahiro, T. et al., Nematicidal and antimicrobial constituents from Allium grayi Regel and *Allium fistulosum* L. var. caespitosum, Agricultural and Biological Chemistry, 52(9): 2383-2385 (1988).

Matsuno, Y. et al., Synthetic Method for Oligonucleotide Block by Using Alkyl-Chain-Soluble Support, Org. Lett., 18: 800-803 (2016).

Matysiak, S et al., Acetals as New 2'-O-Protecting Functions for the Synthesis of the Oligoribonucleotides: Synthesis of Uridine Building Blocks and Evaluatino of Their Relative Acid Stability, Helvetica Chimica Acta 81: 1545-1566 (1998).

Maung, J. et al., Alternatives to 1-H-tetrazole in the preparation of phosphonate diesters and phosphonamidates from phosphonyl dichlorides, Tetrahedron Lett., 45: 6497-6499 (2004).

Mauritz, R.P. et al., Elucidation of the Hydrolytical Properties of α-Hydroxybenzylphosphonates as a New Potential Pro-Oligonucleotide Concept, Nucleosides and Nucleotides, 18(6-7):1417-1418 (1999).

Mauritz, R.P. et al., Synthesis of 3',5'-Dithymidylyl-α-hydroxyphosphonate Dimer Building Blocks for Oligonucleotide Synthesis—A New Pro-oliguncleotide, Nucleosides and Nucleotides, 16(7-9):1209-1212 (1997).

McBride, J.L. et al., Prelinical Safety of RNAi-Mediated HTT Suppression in the Rhesus Macaque as a Potential Therapy for Huntington's Disease, Molecular Therapy, 19: 1-11 (2011).

Meade, M.F., et al., Efficient delivery of RNAi prodrugs containing reversible charge-neutralizing phosphotriester backbone modifications, Nat. Biotech., 32: 1256-61 (2014).

(56) References Cited

OTHER PUBLICATIONS

Medical News Today, AVI BioPharma Announces FDA Clears IND Applications for Clinical Trials of RNA Therapeutic Agents for Treatment of Ebola and Marburg Viruses, Accessed Apr. 2, 2015, 2 pages (Dec. 30, 2008).
Meena, Control of Human RNase H Mediated Cleavage by Stereopure Phosphorothioate Oligonucleotides, WAVE Life Sciences, TIDES Meeting (May 3-6, 2015).
Meena, Development of Allele Specific Antisense Oligonucleotides, WAVE Life Sciences, ACS Central Regional Meeting (CERM), Covington, KY (May 19, 2016).
Meena, Development of Allele Specific Antisense Oligonucleotides, WAVE Life Sciences, TIDES Meeting (May 11, 2016).
Meena, et al., Therapeutic Implications of Controlling P-Chirality in Phosphorothioate Oligonucleotides, TIDES Poster (May 12-15, 2014).
Meena, Optimization of Antisense Drugs by P-Stereochemistry Control, WAVE Life Sciences, OTS Annual Meeting 2014, Oligonucleotide Therapeutics Society (Oct. 12-14, 2014).
Merki, E. et al., Antisense oligonucleotide directed to human apolipoprotein B-100 reduces lipoprotein(a) levels and oxidized phospholipids on human apolipoprotein B-1 00 particles in lipoprotein(a) transgenic mice, Circulation, 118(7): 743-53 (2008).
Mesmaeker, A.D. Backbone modifications in oligonucleotides and peptide nucleic acid systems, Current Opinion in Structural Biology, 5: 343-355 (1995).
Methods in Enzymology, Edited by Widder, K. and Green, R., Drug and Enzyme Targeting, Academic Press, 112: 309-396 (1985).
Mignet, N. et al., Synthesis and evaluation of glucuronic acid derivatives as alkylating agents for the reversible masking of internucleoside groups of antisense oligonucleotides, Carbohydrate Research, 303:17-24 (1997).
Mignet, N. et al., the Prooligonucleotide Approach. V: Influence of the phosphorus atom environment on the hydrolysis of enzymolabile dinucleoside phosphotriesters, Bioorganic and Medicinal Chemistry Letters, 7(7):851-854 (1997).
Milkowski, J.D. et al., Thiol Protection with the Acetamidomethyl Group: S-Acetamidomethyl-I-cysteine Hydrochloride, Organic Syntheses, 6: 5 (1988).
Misaki, Set al., Dehydration of 2-Trifluoromethyl-3,3,3-Trifluoropropanil with Base, Journal of Flourine Chemistry 24: 531-533 (1984).
Molenkamp, B.G. et al., Local Administration of PF-3512676 CpG-B Instigates Tumor-Specific CD8+ T-Cell Reactivity in Melanoma Patients , Clin. Cancer Res., 14(14): 4532-4542 (2008).
Molina, A.G. et al., Acetylated and Methylated β-Cyclodextrins asViable Soluble Supports for the Synthesis of Short 2'-Oligodeoxyribonucleotides in Solution, Molecules, 17: 12102-12120 (2012).
Molina, A.G. et al., Assembly of Short Oligoribonucleotides from Commercially Available Building Blocks on a Tetrapodal Soluble Support, Current Organic Synthesis, 12: 1-6 (2015).
Molina, A.G. et al., Solution phase synthesis of short oligoribonucleotides on a precipitative tetrapodal support, Beilstein Journal of Organic Chemistry, 10: 2279-2285 (2014).
Molina, A.G., Synthesis of Short Oligonucleotides on a Soluble Support by the Phosphoramidite Method, University of Turku, 1-66 (2015).
Monteys, A.M. et al., Artificial miRNAs Targeting Mutant Huntingtin Show Preferential Silencing In Vitro and In Vivo, Molecular THerapy—Nucleic Acids, 4: e234 1-11 (2015).
Monteys, A.M. et al., Single nucleotide seed modification restores in vivo tolerability of a toxic artificial miRNA sequence in the mouse brain, Nucleic Acids Res., 42(21): 13315-13327 (2014).
Morales-Rojas, H. and Kool, E.T., A porphyrin C-nucleoside incorporated into DNA, Organic Letters, 4(25):4377-4380 (2002).
Morcos, P.A., Achieving targeted and quantifiable alteration of mRNA splicing with Morpholino oligos, Biochem. Biophys. Res. Commun., 358(2): 521-527 (2007).
Morvan, F. et al., Cellular uptake and intracellular quantification of fluorescent labeled T20 Me-SATE prooligonucleotides, Nucleosides Nucleotides Nucleic Acids, 20(4-7)1165-1168 (2001).
Morvan, F. et al., Kinetics study of the biotransformation of an oligonucleotide prodrug in cells extract by matrix-assisted laser desorption/ionization time-of-flight mass spectrometry, Nucleosides, Nucleotides and Nucleic Acids, 20(2-4):1159-1163 (2001).
Morvan, F. et al., The Oligonucleotide Prodrug Approach: The Pro-Oligonucleotides, Pharmaceutical Aspects of Oligonucleotides, 79-97 (2000).
Moser, H. E. et al., Sequence-Specific Cleavage of Double Helical DNA by Triple Helix Formation, Science, 238: 645-650 (1987).
Nawrot et al., DNA Oligonucleotides Containing Stereodefined Phosphorothioate Linkages in Selected Positions, Current Protocols in Nucleic Acid Chemistry, UNIT 4.34: 4.34.1-4.34.15 (2009).
Nielsen, J. and Caruthers, M.H., Directed Arbuzov-type reactions of 2-cyano-1,1-dimethylethyl deoxynucleoside phosphites, J. Am. Chem. Soc., 110: 6275-6 (1988).
Nielsen, N.M. and Bundgaard, H. Glycolamide Esters as Biolabile Prodrugs of Carboxylic Acid Agents: Synthesis, Stability, Bioconversion, and Physicochemical Properties, Journal of Pharmaceutical Sciences, 77(4): 285-298 (1988).
Nieuwlandt, D. et al., In Vitro Selection of RNA Ligands to Substance P, Biochemistry, 34: 5651-5659 (1995).
Nilsson et al., Chemical and Stereochemical Aspects of Oxidative Coupling of H-Phosphonate and H-Phosphonothioate Diesters. Reactions with N,N-,N,O and O,O-Binucleophiles, Letters in Organic Chemistry, 2(2): 188-197 (2005).
Nilsson et al., Controlling Stereochemistry During Oxidative Coupling. Preparation of Rp or Sp Phosphoramidates from One P-chiral Precursor, Chem. Commun., (22): 2566-7 (2004).
Nilsson, J. et al., Chemoselectivity in oxidative coupling of bifunctional nucleophiles with dinucleoside H-phosphonate and dinucleoside H-phosphonothioate diesters, Nucleosides, Nucleotides & Nucleic Acids, 22(5-8):1467-1469 (2003).
Nowotny, M. et al., Structure of human RNase H1 complexed with an RNA/DNA hybrid: insight into HIV reverse transcription, Mol Cell, 28(2):264-76 (2007).
Nukaga, Y. et al., Stereocontrolled Solid-Phase Synthesis of Phosphate/Phosphorothioate (PO/PS) Chimeric Oligodeoxyribonucleotides on an Automated Synthesizer Using an Oxazaphospholidine-Phosphoramidite Method, J. Org. Chem., A-J, 10 pages (Publication Date (Web): Mar. 3, 2016).
Nukaga, Y. et al., Stereocontrolled Solid-Phase Synthesis of Phosphorothioate Oligoribonucleotides Using 2'-O-(2-Cyanoethoxymethyl)-nucleoside 3'-O-Oxazaphospholiidine Monomers, Journal of Organic Chemistry, 77(18):7913-7922 (2012).
O'Connell, D. et al., Calcium-dependent oligonucleotide antagonists specific for L-selectin, Proc. Natl. Acad. Sci. USA, 93: 5883-5887 (1996).
Ohgi, T. et al., A New RNA Synthetic Method with a 2'-O-(2-Cyanoethoxymethyl) Protecting Group, Organic Letters, 7(16): 3477-3480 (2005).
Ohkubo et al., Synthesis of oligodeoxyribonucleotides containing hydroxymethylphosphonate bonds in the phosphoramidite method and their hybridization properties, Tetrahedron Letters, 46(51): 8953-8957 (2005).
Oka, N. and Wada, T., Stereocontrolled synthesis of oligonucleotide analogs containing chiral internucleotidic phosphorus atoms, Chemical Society Reviews, 40(12):5829-5843 (2011).
Oka, N. et al., An oxazaphospholidine approach for the stereocontrolled synthesis of oligonucleoside phosphorothioates, Journal of the America Chemical Society, 125(27):8307-8317 (2003).
Oka, N. et al., Diastereocontrolled Synthesis of Dinucleoside Phosphorothioates Using a Novel Class of Activators, Dialkyl(cyanomethyl)ammonium Tetrafluoroborates, Journal of the American Chemical Society, 124(18):4962-4963 (2002).
Oka, N. et al., Solid-Phase Synthesis of Stereoregular Oligodeoxyribonucleoside Phosphorothioates Using Bicyclic Oxazaphospholidine Derivatives as Monomer Units, Journal of the American Chemical Society, 130(47):16031-16037 (2008).

(56) References Cited

OTHER PUBLICATIONS

Oka, N. et al., Stereocontrolled synthesis of dinucleoside boranophosphates by an oxazaphospholidine method, Nucleic Acids Symposium Series, (49): 131-132 (2005).

Oka, N. et al., Stereocontrolled synthesis of oligonucleoside phosphorothioates and PO/PS-chimeric oligonucleotides by using oxazaphospholidine derivatives, Nucleic Acids Symposium Series, 52: 335-336 (2008).

Oka, N. et al., Stereocontrolled Synthesis of Oligoribonucleoside Phosphorothioates by an Oxazaphospholidine Approach, Organic Letters, 11(4):967-970 (2009).

Ostergaard, M. et al., Rational design of antisense oligonucleotides targeting single nucleotide polymorphisms for potent and allele selective suppression of mutant Huntingtin in the CNS, Nucleic Acids Research, 41(21), 9634-9650 (2013).

Otting, G. et al., Why Pentose- and Not Hexose-Nucleid Acids? Part IV. 'Homo-DNA': 1H-, 13C-, 31P-, and 15N-NMR-Spectroscopic Investigation of ddGlc(A-A-A-A-A-T-T-T-T-T) in Aqueous Solution, Helvetica Chimica Acta, 76(8):2701-2756 (1993).

Padmanabhan, S. et al., Anti-HBV nucleotide prodrug analogs: Synthesis, bioreversibility, and cytotoxicity studies, Bioorganic and Medicinal Chemistry Letters, 16(15):1491-1494 (2006).

Pan, Q-W. et al., New therapeutic opportunities for Hepatitis C based on small RNA, World J. Gastroenterol., 13(33): 4431-4436 (2007).

Parrish et al., Functional Anatomy of a dsRNA Trigger: Differential Requirement for the Two Trigger Strands in RNA Interference, Molecular Cell, 6:1077-1087 (2000).

Patil et al., Syntheses and properties of oligothymidylate analogs containing stereoregulated phosphorothioate and phosphodiester linkages in an alternating manner, Bioorganic & Medicinal Chemistry Letters, 4(22): 2663-2666 (1994).

Perrino, E. et al., New sulfurated derivatives of valproic acid with enhanced histone deacetylase inhibitory activity, Bioorganic & Medicinal Chemistry Letters, 18(6): 1893-1897 (2008).

Peyrottes, S. et al., SATE pronucleotide approaches: an overview, Mini-Reviews Medicinal Chemistry, 4(4):395-408 (2004).

Pfister, E.L. et al., Five siRNAs targeting three SNPs may provide therapy for three-quarters of Huntington's disease patients, 19(9): 774-778 (2009).

Pharmacology Review(s), Application No. 203568Orig1s000, Center for Drug Evaluation and Research, Food and Drug Administration, Department of Health & Human Services, 2013.

Pitsch, S. et al., Reliable Chemical Synthesis of Oligoribonucleotides (RNA) with 2'-O-[(Triisopropylsilyl)oxy]methyl(2'-O-tom)-Protected Phosphoramidites, Helvetica Chimica Acta, 84: 3773-3795 (2001).

Poijarvi, P. et al., 2,2-Bis(ethoxycarbonyl)- and 2-(Alkylaminocarbonyl)-2-cyano-Substituted 3-(Pivaloyloxy)propyl Groups as Biodegradable Phosphate Protections of Oligonucleotides, Bioconjugate Chemistry, 16(6):1564-1571 (2005).

Poijarvi, P. et al., The chemical stability of S-(2-acylthioethyl) and S-acyloxymethyl protected thymidylyl-3',5'-thymidine phosphoromonothiolates and their deacylation products in aqueous solution, Nucleosides Nucleotides and Nucleic Acids, 20(1-2):77-91 (2001).

Poijarvi, P. et al., Towards Nucleotide Prodrugs Derived from 2,2-Bis(hydroxymethyl)malonate and Its Congeners: Hydrolytic Cleavage of 2-Cyano-2-(hydroxymethyl)-3-methoxy-3-oxopropyl and 3-(Alkylamino)-2-cyano-2-(hydroxymethyl)-3-oxopropyl Protections from the Internucleosidic Phosphodiester and Phosphorothioate Linkages, Helvetica Chimica Acta, 85(7):1869-1876 (2002).

Poijarvi, P. et al., Towards Oligonucleotide Pro-Drugs: 2,2-Bis(ethoxycarbonyl) and 2-(Alkylaminocarbonyl)-2-cyano Substituted 3-(Pivaloyloxy)Propyl Groups as Biodegradable Protecting Groups for Internucleosidic Phosphoromonothioate Linkages, Letters in Organic Chemistry, 1(2):183-188 (2004).

Poijarvi, P., Prodrug Approaches of Nucleotides and Oligonucleotides, Current Medicinal Chemistry, 13(28):3441-3465 (2006).

Pon, R. T., Solid-Phase Supports for Oligonucleotide Synthesis, Current Protocols in Nucleic Acid Chemistry, 3.1.1-3.1.28 (2000).

Pontiggia, R. et al., 2-C-Methyluridine modified hammerhead riboxyme against the estrogen receptor, Bioorganic & Medicinal Chemistry Letters, 20: 2806-2808 (2010).

Pontiggia, R. et al., DNAzymes and ribozymes carrying 2'-C-methyl nucleotides, Nucleic Acids Sumposium Series, 52: 521-522 (2008).

Potter et al, Stereospecificity of nucleases towards phosphorothioate-substituted RNA: stereochemistry of transcription by T7 RNA polymerase, Nucleinc Acids Research, 15(10): 4145-4162 (1987).

Potter, B.V.L. et al., Synthesis and Configurational Analysis of Dinucleoside Phosphate Isotopically Chiral at Phosphorus. Stereochmical Course of Penicillium citrum Nuclease P1 Reaction, Biochemistry, 22: 1369-1377 (1983).

Prakash, T.P. et al., 2'-O-[2-(Methylthio )ethyl]-Modified Oligonucleotide: an Analogue of 2'O-[2-(Methoxy)-ethyl]-Modified Oligonucleotide with Improved Protein Binding Properties and High Binding Affinity to Target RNA, Biochemistry, 41: 11642-11648 (2002).

Prhavc, M. et al., 2'-O-[2-[2-(N,N-Dimethylamino)ethoxyjethyl] Modified Oligonucleotides: Symbiosis of Charge Interaction Factors and Stereoelectronic Effects, Organic Letters, 5(12): 2017-2020 (2003).

Puri, N. et al, Targeted Gene Knockout by 2'-O-Aminoethyl Modified Triplex Forming Oligonucleotides, J. Biol. Chem., 276: 28991-28998 (2001).

Puri, N. et al., The Synthesis and Reactivity of New 2-(N,N-Diisoprophylamino)-3-Methylsulfonyl-1,3,2-Benzoxazaphospholes. The Utility of the 5-Chloro analogue in the One-Pot Synthesis of Oligothiophosphates: [ApsppA, ApspppA, ppp5'A2'ps5'A, m7GpsppA, Apspppp, Apspp], Tetrahedron 51(10): 2991-3014 (1995).

Pérez, B. et al., Antisense Mediated Splicing Modulation for Inherited Metabolic Diseases: Challenges for Delivery, Nucleic Acid Therapies, 24(1): 48-56 (2014).

Ravikumar, V.T. et al., Unylinker: An Efficient and Scaleable Synthesis of Oligonucleotides Utilizing a Universal Linker Molecule: A Novel Approach to Enhance the Purity of Drugs, Org. Process Res. Dev., 12(3): 399-410 (2008).

Reese, C.B. and Yan, H., Solution phase synthesis of ISIS 2922 (Vitravene) by the modified H-phophane approach, J. Chem. Soc., Perkin Trans. I, 2619-2633 (2002).

Regan, J.F. et al., A Rapid Molecular Approach for Chromosomal Phasing, PLOS ONE, 1-15 (2015).

Reither, S. and Jeltsch, A., Specificity of DNA triple helix formation analyzed by a FRET assay, BMC Biochemistry, 3: 9 pages (2002).

Revankar, G. R. and Rao, T.S., DNA with Altered Bases, DNA and Aspects of Molecular Biology, Comprehensive Natural Products Chemistry, 7.09: 313-339 (1999).

Robinson, D.S. et al., Predominant TH2-Like Bronchoalveolar T-Lymphocyte Population in Atopic Asthma, The New England Journal of Medicine, 326: 298-304 (1992).

Rossetti, G., Structural aspects of the Huntingtin protein investigated by biocomputing methods, Thesis, RWTH Aachen University, Forschungszentrum Juelich, 173 pages (2011).

Rozners, E. et al., Evaluation of 2'-hydroxyl protection in RNA-synthesis using the H-phosphonate approad, Nucleic Acids Research, 22(1): 94-99 (1994).

Sakatsume, O. et al., Solid Phase Synthesis of Oligoribonucleotides by the Phosphoramidite Approach Using 2'-O-1-(2-Chloroethoxy)Ethyl Protection, Tetrahedron, 47(41): 8717-8728 (1991).

Saneyoshi, H. et al., A General Method for the Synthesis of 2'-0-Cyanoethylated Oligoribonucleotides Having Promising Hybridization Affinity for DNA and RNA and Enhanced Nuclease Resistance, The Journal of Organic Chemistry, 70(25): 10453-10460 (2005).

Schmitz, C. et al., Synthesis of P-Stereogenic Phosphoramidite and Phosphorodiamidite Ligands and Their Application in Asymmetric Catalysis, Eur. J. Org. Chem., 6205-6230 (2015).

Schoning, K.-U. et al., Chemical Etiology of Nucleic Acid Structure: The α-Threofuranosyl-(3'->2') Oligonucleotide System, Science, 290(5495):1347-1351 (2000).

(56) References Cited

OTHER PUBLICATIONS

Schultz, C., Prodrugs of Biologically Active Phospate Esters, Bioorganic and Medicinal Chemistry, 11(6):885-898 (2003).
Schulz, W.G. and Cai, S.L., Synthetic Genetics, Chemical and Engineering News, 5 (2012).
Scrimgeour, E.M. Huntington Disease (Chorea) in the Middle East, SQU. Med. J., 9(1): 16-23 (2009).
Seela et al, Diastereomerically pure Rp and Sp dinucleoside H-phosphonates. The stereochemical course of their conversion into P-methylphosphonates, phosphorothioates and [18O] chiral phosphates, Journal of Organic Chemistry, 56(12): 3861-3869 (1991).
Seidman, M.M. and Glazer, P.T. The potential for gene repair via triple helix formation, The Journal of Clinical Investigation, 112(4): 487-494 (2003).
Senn, J.J. et al., Non-CpG-Containing Antisense 2-Methoxyethyl Oligonucleotides Activate a Proinflammatory Response Independent of Toll-Like Receptor 9 or Myeloid DifferentiationFactor 88, The Journal of Pharmacology and Experimental Therapeutics, 314: 972-979 (2005).
Sergueeva et al., Synthesis of Dithymidine Boranophosphates via Stereospecific Boronation of H-phosphonate Diesters and Assignment of their Configuration, Tetrahedron Letters, 40: 2041-2044 (1999).
Seth, P., and Olson, R., Nucleic Acid Therapeutics—Making Sense of Antisesnse, 2016 Drug Design and Delivery Symposium, ACS Webinar, 1-36 (Jul. 26, 2016).
Seth, P.P. et al., An Exocyclic Methylene Group Acts as a Bioisostere of the 2'Oxygen Atom in LNA, J. Am. Chem. Soc, 132(42): 14942-14950 (2010).
Sharma, V.K. et al. Antisense oligonucleotides: modifications and clinical trials, Med. Chem. Commun., 5: 1454-71 (2014).
She, X. et al., Synergy between Anti-Endoglin (CD105) Monoclonal Antibodies and TGF-β in Suppression of Growth of Human Endothelial Cells, Int. J. Cancer, 108: 251-257 (2004).
Sheehan, J.P. and Phan, T.M. Phosphorothioate Oligonucleotides Inhibit the Intrinsic Tenase Complex by an Allosteric Mechanism, Biochemistry, 40: 4980-4989 (2001).
Sierzchala et al., Oxathiaphospholane Method of Stereocontrolled Synthesis of Diribonucleoside 3', 5' - Phosphorotioates, Journal of Organic Chemistry 61(19): 6713-6716 (1996).
Silverman, R.H., A scientific journey through the 2-5A/RNase L system, Cytokine Growth Factor Reviews, 18(5-6):381-388 (2007).
Singhrao, S.K. et al., Increased Complement Biosynthesis by Microglia and Complement Activation on Neurons in Huntington's Disease, Experimental Neurology, 159: 362-376 (1999).
Skotte, N.H. et al., Allele-specific suppression of mutant huntingtin using antisense oligonucleotides: providing a therapeutic option for all Huntington disease patients, PLoS One, 9(9): e107434 1-18 (2014).
Small, L.D. et al.,Comparison of Some Properties of Thiolsulfonates and Thiolsulfinates, Journal of the American Chemical Society, 71(10): 3565-3566 (1949).
Smith, A. et al., The murine haemopexin receptor, Biochem. J., 276: 417-425 (1991).
Sobkowski, et al. Stereochemistry of internucleotide bond formation by the H?phosphonate method. 1. Synthesis and 31P NMR analysis of 16 diribonulceoside (3'-5')-H-phosphonates and the corresponding phosphorothioates, Nucleosides Nucleotides Nucleic Acids, 24(10-12): 1469-84 (2005).
Sonveaux, E., Protecting Groups in Oligonucleotide Synthesis, Protocols for Oligonucleotide Conjugates, Methods in Molecular Biology, Edited by Agrawal, S., Humana Press, 26:1-71 (1994).
Spinelli, N. et al., Use of Allylic Protecting Groups for the Synthesis of Base-Sensitive Prooligonucleotides, European Journal of Organic Chemistry, 49-56 (2002).
Sproat, B.S., RNA Synthesis Using 2'-O-(Tert-Butyldimethylsilyl) Protection, Methods in Molecular Biology, 288: 17-31 (2005).
Stawinski et al., Nucleoside H-phosphonates. 14. Synthesis of nucleoside phosphoroselenoates and phosphorothioselenoates via stereospecific selenization of the corresponding H-phosphonate and H-phosphonothioate diesters with the aid of new selenium-transfer reagent, 3H-1,2-benzothiaseleno1-3-one, J. Org. Chem., 59(1): 130-136 (1994).
Stawinski et al., Stereospecific oxidation and oxidative coupling of H-phosphonate and H-phosphonothioate diesters, Tetrahedron Letters, 33(22):3185-3188 (1992).
Stawinski, J. and Stromberg, R. Di- and Oligonucleotide Synthesis Using H-Phosphonate Chemistry, Methods in Molecular Biology, 288: 81-100 (2005).
Stawinski, J. and Thelin, M., 3-H-2,1-benzoxathiol-3-one 1-oxide—A New Reagent for Stereospecific Oxidation of Nucleoside H-Phosphonothioate Diesters, Tetrahedron Letters, 33(22): 3189-3192 (1992).
Stawinski, J. and Thelin, M., 3H-1,2-benzothiaseleno1-3-one. A new selenizing reagent for nucleoside H-phosphonate and H-phosphonothioate diesters, Tetrahedron Letters, 33(47): 7255-7258 (1992).
Stec et al., Deoxyribonucleoside 3'-O-(2-Thio- and 2-Oxo-"spiro"-4,4-pentamethylene-1,3,2-oxathiaphospholane)s:? Monomers for Stereocontrolled Synthesis of Oligo(deoxyribonucleoside phosphorothioate)s and Chimeric PS/PO Oligonucleotides, J. Am. Chem. Soc., 120(29): 7156-7167 (1998).
Stec et al., Stereocontrolled Synthesis of Oligo (nucleoside phosphorothioate)s , Angew. Chem. Int. Ed. Engl., 33:709-722 (1994).
Stec et al., Stereospecific Synthesis of P-Chiral Analogs of Oligonucleotides, Methods in Molecular Biology, 20: 285-313 (1993).
Stec, Oligo(nucleoside Phosphorothioate)s: The Quest of P-Chirality, in Phosphorus, Sulfur, and Silicon, 177(6): 1775-1778 (2002).
Stec, W.J. and Zon, G., Stereochemical Studies of the Formation of Chiral Internucleotide Linkages by Phosphormadite COupling in the Synthesis of Oligodeocyribonucleotides, Tetrahedron Letters, 25(46): 5279-5282 (1984).
Stec, W.J. et al., Automated Solid-Phase Synthesis, Separation, and Stereochemistry of Phosphorothioate Analogues of Oligodeocyribonucleotides, J. Am. Chem. Soc., 106: 6077-6079 (1984).
Stec, W.J. et al., Diastereomers of Nucleoside 3'-O-(2-Thio-1,3,2-oxathia(selena)phospholanes): Building Blocks for Stereocontrolled Synthesis of Oligo(nucleoside phosphorothioate)s, Journal of the American Chemical Society, 117(49):12019-12029 (1995).
Stec, W.J. et al., Novel route to oligo(deoxyribonucleoside phosphorothioates). Stereocontrolled synthesis of P-chiral oligo(deoxyribonucleoside phosphorothioates), Nucleic Acids Research, 19(21):5883-5888 (1991).
Stec, W.J. et al., Stereodependent inhibition of plasminogen activator inhibitor type 1 by phosphorothioate oligonucleotides: proof of sequence specificity in cell culture and in vivo rat experiments, Antisense Nucleic Acid Drug Dev., 7(6):567-73 (1997).
Stein, C.A. and Cheng, Y.C., Antisense oligonucleotides as therapeutic agents—is the bullet really magical?, Science, 261(5124):1004-12 (1993).
Sureshbabu, V.V. et al., Synthesis of tetrazole analogues of amino acids using Fmoc chemistry: isolation of amino free tetrazoles and their incorporation into peptides, Tetrahedron Letters, 48(39): 7038-7041 (2007).
Suska, A. et al., Antisense oligonucleotides: Stereocontrolled synthesis of phosphorothioate oligonucleotides, Pure and Applied Chemistry, 65(4):707-714 (1993).
Swayze, E.E. and Bhat, B., The medicinal chemistry of oligonucleotides, Crooke, S.T. (ed) Antisense Drug Technology: Principles, Strategies, and Applications, CRC Press, Boca Raton, FL: 143-82 (2007).
Swayze, E.E. et al., Antisense oligonucleotides containing locked nucleic acid improve potency but cause significant hepatotoxicity in animals, Nucleic Acids Research, 35(20: 687-700 (2007).
Takahashi, D. et al., Novel diphenylmethyl-Derived Amide Protecting Group for Efficient Liquid-Phase Peptide Synthesis: AJIPHASE, Org. Lett., 14(17): 4514-4517 (2012).
Takeno, H. et al., Selection of an RNA Molecule that Specifically Inhibits the Protease Activity of Subtilisin, J. Biochem., 125: 1115-1119 (1999).

(56) References Cited

OTHER PUBLICATIONS

Tam, Journal of Hematotherapy & Stem Cell Research, 12: 467-471 (2003).
Tamura et al., Preparation of Stereoregulated Antisense Oligodeoxyribonucleoside Phoshorothioate and Interaction with its Complementary DNA and RNA, Nucleosides & Nucleotides,17(1-3): 269-282 (1998).
Tang, J. et al., Enzymatic Synthesis of Stereoregular (All Rp) Oligonucleotide Phosphorothioate and Its Properties, Nucleosides Nucleotides, 14(3-5):985-990 (1995).
Tawarada, R. et al., Mechanistic studies on oxidative condensation of a thymidine 3'-H-phosphonate derivative with 3'-O-acetylthymidine, Archive for Organic Chemistry, (3):264-273 (2009).
Thayer, J.R. et al., Separation of oligonucleotide phosphorothioate distereoisomers by pellicular anion-exchange chromatography, Journal of Chromatography A, 1218: 802-808 (2011).
Tomoskozi et al., Stereospecific conversion of H-phosphonates into phosphoramidates. The use of vicinal carbon-phosphorus couplings for configurational determination of phosphorus, Tetrahedron, 51(24): 6797-6804 (1995).
Tosquellas, G. et al., First synthesis of alternating SATE-phosphotriester/phosphodiester prooligonucleotides on solid support, Bioorganic and Medicinal Chemistry Letters, 8(20): 2913-2918 (1998).
Tosquellas, G. et al., Prooligonucleotides exhibit less serum-protein binding than phosphodiester and phosphorothioate oligonucleotides, Nucleosides, Nucleotides and Nucleic Acids, 19(5-6):995-1003 (2000).
Tosquellas, G. et al., The pro-oligonucleotide approach: solid phase synthesis and preliminary evaluation of model pro-dodecathymidylates, Nucleic Acids Research, 26(9):2069-2074 (1998).
Tosquellas, G. et al., The Prooligonucleotide Approach III: Synthesis and bioreversibility of a chimeric phosphorodithioate prooligonucleotide, Bioorganic and Medicinal Chemistry Letters, 6(4):457-462 (1996).
Tosquellas, G. et al., The Prooligonucleotide Approach IV : Synthesis of chimeric prooligonucleotides with 6 enzymolabile masking groups and unexpected desulfurization side reaction, Bioorganic and Medicinal Chemistry Letters, 7(3):263-268 (1997).
Tsai, C.H. et al., Enzymatic synthesis of DNA on glycerol nucleic acid templates without stable duplex formation between product and template, Proceedings of the National Academy of Science, 104(37):14598-14603 (2007).
Tuerk, C. and Gold, L., Systematic Evolution of Ligans by Exponential Enrichment: RNA Ligands to Bacteriophage T4 DNA Polymerase, Science, 249: 505-510 (1990).
Turner, D.H. et al, Improved Parameters for Prediction of RNA Structure, Cold Spring Harbor Symposia on Quantitative Biology, LII: 123-133 (1987).
Turner, D.H. et al., Free Energy Increments for Hydrogen Bonds in Nucleic Acid Base Pairs, J. Am. Chem. Soc., 109: 3783-3785 (1987).
U.S. Food and Drug Administration, Development of New Stereoisomeric Drugs, 8 pages (May 1, 1992). URL: http://www.fda.gov/Drugs/GuidanceComplianceRegulatoryInformation/Guidances/ucm122883.htm [Retrieved Jun. 15, 2016].
Umemoto, T et al., Oligoribonucleotide Synthesis by the use of 1-(2-cyanoethoxy)ethyl (CEE) as a 2'-hydroxy protecting group, Tetrahedron Letters 45: 9529-9531 (2004).
Uphoff, K.W. et al., In vitro selection of aptamers: the death of pure reason, Curr. Opin. Struct. Biol., 6: 281-288 (1996).
Usman, N. et al., Automated Chemical Synthesis of Long Oligoribonucleotides Using 2'-O-Siylylated Ribonucleoside 3'-O-Phosphoramidites on a Controlled-Pore Glass Support, J. Am. Chem. Soc. 109(25): 7845-7854 (1987).
Uznanski, B. et al., Stereochemistry of base-catalyzed ring opening of 1,3,2-oxathiaphospholanes. Absolute configuration of 2-{N-[(Rc)-1-(.alpha.-naphthyl)ethyl]amino}-2-thiono-1,3,2-oxathiaphospholanes and O,S-dimethyl N-[(Rc)-1-(.alpha.-naphthyl)ethyl]phosphoramidothioates, Journal of the American Chemical Society, 114(26):10197-10202 (1992).

Van Der Veken, P. et al., Irreversible inhibition of dipeptidyl peptidase 8 by dipeptide-derived diaryl phosphonates, Journal of Medicinal Chemistry, 50(23): 5568-5570 (2007).
Vasquez, K.M. et al., Chromosomal mutations induced by triplex-forming oligonucleotides in mammalian cells, Nucl. Acids Res. 27(4): 1176-1181 (1999).
Verma, S. and Eckstein, F., Modified Oligonucleotides: Synthesis and Strategy for Users, Annu. Rev. Biochem., 67: 99-134 (1998).
Vermeulen, A. et al., Double-Stranded Regions Are Essential Design Components of Potent Inhibitors of RISC Function, RNA, 13: 723-730 (2007).
Vives, E. et al., Lipophilic pro-oligonucleotides are rapidly and efficiently internalized in HeLa cells, Nucleic Acids Research, 27(20):4071-4076 (1999).
Vlassov, V.V. et al., Transport of oligonucleotides across natural and model membranes, Biochimica et Biophysica Acta, 1197: 95-108 (1994).
Vu, H. and Hirschbein, B.L., Internucleotide Phosphite Sulfurization With Tetraethylthiuram Disulfide. Phosphorothioate Oligonucleotide Synthesis Via Phosphoramidite Chemistry, Tetrahedron Letters, 32(26):3005-3008 (1991).
Vuyisich, M. and Beal, P.A., Regulation of the RNA-dependent protein kinase by triple helix formation, Nuc, Acids Res., 28(12): 2369-74 (2000).
Wada et al., Stereocontrolled Synthesis of Phosphorothioate RNA by the Oxazaphospholidine Approach, Nucleic Acids Symp. Ser., 48: 57-58 (2004).
Wada, T. et al., Chemical synthesis and properties of stereoregulated phosphorothioate RNAs, Nucleic Acids Symposium Series, 51:119-120 (2007).
Wada, T. et al., Stereocontrolled synthesis of phosphorothioate DNA by an oxazaphospholidine approach, Nucleic Acids Research Supplement, 3:109-110 (2003).
Wada, Takeshi, Chapter I Development of nucleic acid medicines, 3.3 Chemical synthesis of phosphorous atom-modified nucleic acids, CMC Publication., Fronteir of Development of Nucleic Acid Medicine: 67-75 (2009).
Wagner, C.R. et al., Pronucleotides: toward the in vivo delivery of antiviral and anticancer nucleotides, Medicinal Research Reviews, 20(6):417-451 (2000).
Walker, J.R. et al., Structure of the Ku heterodimer bound to DNA and its implications for double-strand break repair, Nature, 412: 607-614 (2001).
Wan et al., Synthesis of Second Generation Antisense Oligonucleotides Containing Chiral Phosphorothioate Linkages and Evaluation of their Biophysical Properties and Biological Activity, 10th Annual Meeting of the Oligonucleotide Therapeutics Society, abstract received by Applicant Oct. 7, 2014, poster setup prior to presentation (first known to Applicant late Oct. 12, 2014, PST), poster presentation Oct. 13, 2014.
Wan, W.B. and Seth, P.P., The Medicinal Chemistry of Therapeutic Oligonucleotides, J. Med. Chem., 59: 9645-9667 (2016).
Wan, W.B. et al., Synthesis, biophysical properties and biological activity of second generation antisense oligonucleoties containing chiral phosphorothioate linkages, Nucleic Acid Research, 27 pages, online advance access (2014).
Wang H, et al., Therapeutic gene silencing delivered by a chemically modified siRNA against mutant SOD 1 slows ALS progression, The Journal of Biological Chemistry, 283(23):15845-15852 (2008).
Wang, J.-C. et al., A stereoselective synthesis of dinucleotide phosphorothioate triesters through a chiral indol-oxazaphosphorine intermediate, Tetrahedron Letters, 38(5):705-708 (1997).
Warby, S.C. et al., CAG expansion in the Huntington disease gene is associated with a specific and targetable predisposing haplogroup, Am. J. Hum. Genet., 84(3): 351-366 (2009).
WaVe Life Sciences Poster, Therapeutic Implications of Controlling P-Chirality in Phosphorothioate Oligonucleotides, TIDES, San Diego (May 3-6, 2014).
WAVE Life Sciences Press Release, WAVE Life Sciences Added to the Russell 2000® Index, 2 pages (Jun. 27, 2016).

(56) References Cited

OTHER PUBLICATIONS

WAVE Life Sciences Press Release, WAVE Life Sciences Announces Plan to Deliver Six Clinical Programs by 2018, 6 pagex (Jan. 29, 2016).
WAVE Life Sciences Press Release, WAVE Life Sciences Announces Pricing of Initial Public Offering, 3 pages (Nov. 11, 2015).
WAVE Life Sciences Press Release, WAVE Life Sciences Appoints Dr. Michael Panzara as Head of Neurology Franchise, 4 pages (Jul. 12, 2016).
WAVE Life Sciences Press Release, WAVE Life Sciences Appoints Keith Regnante as Chief Financial Officer, 4 pages (Aug. 17, 2016).
WAVE Life Sciences Press Release, WAVE Life Sciences Appoints Roberto Guerciolini, M. Senior Vice President and Head of Early Development, 2 pages (Apr. 7, 2015).
WAVE Life Sciences Press Release, Wave Life Sciences Closed $18 Million Series A Financing to Advance Stereopure Nucleic Acid Therapeutics, 3 pages (Feb. 2, 2015).
WAVE Life Sciences Press Release, Wave Life Sciences Enters Collaboration with Pfizer to Develop Genetically Targeted Therapies for the Treatment of Metabolic Diseases, 5 pages (May 5, 2016).
WAVE Life Sciences Press Release, WAVE Life Sciences Expands Stereopure Synthetic Chemistry Platform Capabilities, Augments Patent Portfolio with Addition of Single-Stranded RNAi (ssRNAi), 3 pages (Jun. 8, 2015).
WAVE Life Sciences Press Release, WAVE Life Sciences Raises $66 Million in Series B Financing, 3 pages (Aug. 18, 2015).
WAVE Life Sciences Press Release, WAVE Life Sciences Receives Orphan Drug Designation from FDA for its Lead Candidate Designed to Treat Huntington's Disease, 5 pages (Jun. 21, 2016).
WAVE Life Sciences Press Release, WAVE Life Sciences Reports First Quarter 2016 Financial Results and Provides Business Update, 9 pages (May 16, 2016).
WAVE Life Sciences Press Release, WAVE Life Sciences Reports Fourth Quarter and Full Year 2015 Financial Results and Provides Business Update, 10 pages (Mar. 30, 2016).
WAVE Life Sciences Press Release, WAVE Life Sciences Reports Second Quarter 2016 Financial Results and Provides Business Update, 10 pages (Aug. 15, 2016).
WAVE Life Sciences Press Release, WAVE Life Sciences to Advance Next-Generation Nucleic Acid Therapies to Address Unmet Need in Duchenne Muscular Dystrophy, 6 pages (May 9, 2016).
WAVE Life Sciences Press Release, WAVE Life Sciences to Present at the Deutsche Bank 41st Annual Health Care Conference, 2 pages (Apr. 29, 2016).
WAVE Life Sciences Press Release, WAVE Life Sciences to Present at the Jefferies 2016 Healthcare Conference, 2 pages (Jun. 1, 2016).
WAVE Life Sciences Press Release, WAVE Life Sciences to Present at the JMP Securities Life Sciences Conference, 2 pages (Jun. 15, 2016).
WAVE Life Sciences Press Release, WAVE Life Sciences to Present at the LEERINK Partner 5th Annual Global Healthcare Conference, 2 pages (Feb. 3, 2016).
WAVE Life Sciences Press Release, WAVE Life Sciences to Present at the Leerink Partners Rare Disease & Immuno-Oncology Roundtable, 2 pages (Sep. 14, 2016).
WAVE Life Sciences Press Release, WAVE Life Sciences to Present at the SunTrust Robinson Humphrey 2016 Orphan Drug Day Conference, 2 pages (Feb. 16, 2016).
Weidner, J.P. et al., Alkyl and Aryl Thiolsulfonates, Journal of Medicinal Chemistry, 7(5): 671-673 (1964).
Weiser, T.G., et al., An estimation of the global volume of surgery: a modeling strategy based on available data, Lancet, 372(9633): 139-144 (2008).
Welz et al., 5-(Benzylmercapto)-1H-tetrazole as activator for 2'-O-TBDMS phosphoramidite building blocks in RNA synthesis, Tetrahedron Letters, 43: 795-797 (2002).
Wengel, J., Synthesis of 3'-C- and 4'-C-Branched Oligodeoxynucleotides and the Development of Locked Nucleic Acid (LNA), Acc. Chem. Res., 32: 301-310 (1999).
Widdison, W. C. et al., Semisynthetic Maytansine analogues for the targeted treatment of cancer, Journal of Medicinal Chemistry, 49(14): 4392-4408 (2006).
Wild, E. et al., Quantification of mutant huntingtin protein in cerebrospinal fluid from Huntington's disease patients, The Journal of Clinical Investigation, 125(5): 1979-1986 (2015).
Wilk, A. and Stec, W.J., Analysis of oligo(deoxynucleoside phosphorothioate)s and their diastereomeric composition, Nucleic Acids Research, 23(3):530-534 (1995).
Wilk, A. et al., Deoxyribonucleoside Cyclic N-Acylphosphoramidites as a New Class of Monomers for the Stereocontrolled Synthesis of Oligothymidylyl- and Oligodeoxycytidylyl-Phosphorothioates, Journal of the American Chemical Society, 122(10): 2149-2156 (2000).
Wong, Chui Ming, Synthesis of anisomycin. Part I. The stereospecific synthesis of N-benzoyl-2-(p-methoxybenzyl)-3-hydroxy-4-carboxamido pyrrolidine and the absolute configuration of anisomycin, Canadian journal of Chemistry 46: 1101-1104 (1968).
Wright, P. et al., Large scale synthesis of oligonucleotides via phosphoramidite nucleosides and a high-loaded polystyrene support, Tetrahedron Letters, 34(21):3373-3736 (1993).
Written Opinion for PCT/IB2009/007923, 8 pages (dated Sep. 6, 2010).
Written Opinion for PCT/IB2015/000395, 10 pages (dated Oct. 30, 2015).
Written Opinion for PCT/JP11/55018, 3 pages (dated Mar. 29, 2011).
Written Opinion for PCT/JP11/71559, 6 pages (dated Dec. 20, 2011).
Written Opinion for PCT/JP15/50716 and English Translation, 11 pages (dated Apr. 21, 2015).
Written Opinion for PCT/JP2010/065900, 5 pages (dated Sep. 15, 2010).
Written Opinion for PCT/JP2013/004303, 6 pages (dated Aug. 13, 2013).
Written Opinion for PCT/JP2015/050714, and English Translation, 11 pages (dated Apr. 21, 2015).
Written Opinion for PCT/JP2015/050718 and English Translation, 6 pages (dated Apr. 21, 2015).
Written Opinion for PCT/US2010/041068, 11 pages, (dated Sep. 1, 2010).
Written Opinion for PCT/US2011/064287, 14 pages (dated Apr. 12, 2012).
Written Opinion for PCT/US2012/046805, 9 pages (dated Sep. 19, 2012).
Written Opinion for PCT/US2013/050407, 12 pages (dated Jan. 9, 2014).
Written Opinion for PCT/US2016/043542, 14 pages (dated Dec. 28, 2016).
Written Opinion for PCT/US2016/043598, 10 pages (dated Nov. 28, 2016).
Wu, X. et al., Synthesis of 5'-C- and 2'-O-(Bromoalkyl)-Substituted Ribonucleoside Phosphoramidites for the Post-synthetic Functionalization of Oligonucleotides on Solid Support, Helvetica Chimica Acta, 83: 1127-1144 (2000).
Xiang, Y. et al., Effects of RNase L mutations associated with prostate cancer on apoptosis induced by 2',5'-oligoadenylates, Cancer Research, 63(20):6795-6801 (2003).
Xiong, H.Y. et al., The human splicing code reveals new insights into the genetic determinants of disease, Science, 347(6218): 144 1254806-1-1254806-8 (2015).
Xu, D. and Esko, J.D., Demystifying Heparan Sulfate—Protein Interactions, Annu. Rev. Biochem., 83: 129-157 (2014).
Xu, L. et al., Cyclic ADP-ribose analogues containing the methylenebisphosphonate linkage: effect of pyrophosphate modifications on Ca2+ release activity, J. Med. Chem., 48(12): 4177-4181 (2005).
Yamada, O. et al., Diastereoselective Synthesis of 3,4-Dimethoxy-7-morphinanone: A Potential Route to Morphine, Organic Letters, 2(18): 2785-2788 (2000).
Yamakage, S-i. et al., 1-(2-Chloroethoxy)Ethyl Group for the Protection of 2'-Hydroxyl Group in the Synthesis of Oligoribonucleotides, Tetrahedron Letters, 30(46): 6361-6364 (1989).

(56) References Cited

OTHER PUBLICATIONS

Yamamoto, S. et al., Unique Palindromic Sequences in Synthetic Oligonucleotides are Required to Induce INF and Augment INF-Mediated Natural Killer Activity, J. Immunol., 148(12): 4072-4076 (1992).

Yamato, K. et al., Enhanced specificity of HPV16 E6E7 siRNA by RNA-DNA chimera modification, Cancer Gene Therapy, 18: 587-597 (2011).

Yanai, H. et al., Suppression of immune responses by nonimmunogenic oligodeoxynucleotides with high affinity for high-mobility group box proteins (HMGBs), PNAS Early Edition, 1-6 (2011).

Yu, D. et al., Accessible 5'-end of CpGcontaining phosphorothioate oligodeoxynucleotides is essential for immunostimulatory activity, Bioorganic & Medicinal Chemistry Letters, 10: 2585-2588 (2000).

Yu, D. et al., Single-Stranded RNAs Use RNAi to Potently and Allele-Selectively Inhibit Mutant Huntingtin Expression, Cell, 150: 895-908 (2012).

Yu, D. et al., Stereo-Enriched Phosphorothioate Oligodeoxynucleotides: Synthesis, Biophysical and Biological Properties, Bioorganic & Medicinal Chemitry, 8: 275-284 (2000).

Yu, R.Z. et al., Cross-species comparison of in vivo PK/PD relationships for second-generation antisense oligonucleotides targeting apolipoprotein B-100, Biochem. Pharmacol., 77: 910-919 (2009).

Yu, S. et al., A One-Pot Formal [4+2] Cycloaddition Approach to Substituted Piperidines, Indolizidines, and Quinolizidines. Total Synthesis of Indolizidine (−)-209I, Journal of Organic Chemicals, 70:7364-7370 (2005).

Zhang, J. et al., Optimization of Exon Skipping Therapies for Duchenne Muscular Dystrophy, WAVE Life Sciences, PPMD: Parent Project Muscular Dystrophy Meeting, Orlando, FL (Jul. 25, 2016).

Zhang, L. et al., A simple glycol nucleic acid, Journal of the American Chemical Society,127(12):4174-4175 (2005).

Zhang, R.S. et al., Synthesis of two mirror image 4-helix junctions derived from glycerol nucleic acid, Journal of the American Chemical Society, 130(18):5846-5847 (2008).

Zhao, J. et al., Genome-wide Identification of Polycomb-Associated RNAs by RIP-seq, Molecular Cell, 40: 939-953 (2010).

Zlatev et al., Phosphoramidate dinucleosides as hepatitis C virus polymerase inhibitors, J Med Chem., 51(18): 5745-57 (2008).

Zon, Automated synthesis of phosphorus-sulfur analogs of nucleic acids—25 years on: potential therapeutic agents and proven utility in biotechnology, New J. Chem., 34(5): 795-804 (2010).

Zon, G and Stec, W.J., Phosphorothioate oligonucleotides, Oligonucleotides and Analogues: A Practical Approach, 87-108 (1991).

Fearon, K. et al., Phosphorothioate oligodeoxynucleotides: large-scale synthesis and analysis, impurity characterization, and the effect of phosphorus stereochemistry, Oligonucleotides as Therapeutic Agents, Ciba Found. Symp. 209: 19-31 (1997).

Aaronson, J.G. et al., Rapid HATU-Mediated Solution Phase siRNA Conjugation, Bioconjugate. Chem., 22: 1723-1728 (2011).

Anthony, K. et al., Exon Skipping Quantification by Quantitative Reverse-Transcription Polymerase Chain Reaction in Duchenne Muscular Dystrophy Patients Treated with the Antisense Oligomer Eteplirsen, Human Gene Therapy Methods, 23: 336-345 (2012).

Blade, H. et al., Modular Synthesis of Constrained Ethyl (cEt) Purine and Pyrimidine Nucleosides, J. Org. Chem., 80: 5337-5343 (2015).

Burgers, P. M. J. et al., Stereochemistry of Hydrolysis by Snake Venom Phosphodiesterase, J. Biol. Chem., 254(16): 7476-7478 (1979).

Burgers, P.M.J. and Eckstein, F., A Study of the Mechanism of DNA Polymerase I from *Escherichia coli* with Diastereomeric Phosphorothioate Analogs of Deoxyadenosine Triphosphate, J. Biol. Chem., 254(15): 6889-6893 (1979).

Burgers, P.M.J. and Eckstein, F., Diastereomers of 5?-O-adenosyl 3?-O-uridyl phosphorothioate: chemical synthesis and enzymatic properties, Biochemistry, 18: 592-596 (1979).

Chak, L-L, and Okamura, K., Argonaute-dependent small RNAs derived from single-stranded, non-structured precursors, Frontiers in Genetics, 5(172): 1-15 (2014).

Chappell, C. et al., Involvement of human polynucleotide kinase in double-strand break repair by non-homologous end joining, The EMBO Journal, 21(11): 2827-2832 (2002).

Cheloufi, S. et al., A Dicer-independent miRNA biogenesis pathway that requires Ago catalysis, Nature, 465(7298): 584-589 (2010).

Chen, B. and Bartlett, M., A One-Step Solid Phase Extraction Method for Bioanalysis of a Phosphorothioate Oligonucleotide and Its 3' n-1 Metabolite from Rat Plasma by uHPLC-MS/MS, The AAPS Journal, 14(4): 772-780 (2012).

Dias, N. and Stein, C.A., Antisense Oligonucleotides: Basic Concepts and Mechanisms, Molecular Cancer Therapeutics, 1: 347-355 (2002).

Dikfidan, A. et al., RNA Specificity and Regulation of Catalysis in the Eukaryotic Polynucleotide Kinase Clp1, Molecular Cell, 54: 975-986 (2014).

Documents submitted to and/or received from the United States Securities and Exchange Commission; downloaded from EDGAR (Nov. 9, 2016 to May 10, 2017).

Egholm, M. et al., PNA hybridizes to complementary oligonucleotides obeying the Watson-Crick hydrogen-bonding rules, Nature, 365, 566-568 (1993).

Erler, W. et al., Patient Advisory Board Meeting, WAVE Life Sciences, London, 46 pages (Mar. 2, 2017).

Erler, W., Stereopure Exon 51-Skipping Oligonucleotide as a Potential Disease-Modifying Therapy for Duchenne Muscular Dystrophy, WAVE Life Sciences, 10 pages (2017).

Ewles, M. et al, Quantification of oligonucleotides by LC-MS/MS: the challenges of quantifying a phosphorothioate oligonucleotide and multiple metabolites, Bioanalysis, 6(4), 447-464 (2014).

Exiqon, Locked Nucleic Acid (LNA), Custom Oligonucleotides for RNA and DNA Research, 16 pages (Aug. 2009).

Freschauf, G., Identification of Small Molecule Inhibitors of the Human DNA Repair Enzyme Polynucleotide Kinase/Phosphatase, Master of Science in Experimental Oncology Thesis, University of Alberta, 155 pages (2011).

Gallier, F. et al., 5',6'-Nucleoside Phosphonate Analogues Architecture: Synthesis and Comparative Evaluation towards Metabolic Enzymes, Chem Med Chem, 6: 1094-1106 (2011).

Giacometti, R.D. et al., Design, synthesis, and duplex-stabilizing properties of conformationally constrained tricyclic analogues of LNA, Org. Biomol. Chem., 14: 2034-2040 (2016).

Gryaznov, S. and, Chen, J.-K., Oligodeoxyribonucleotide N3'4P5' Phosphoramidates: Synthesis and Hybridization Properties, J. Am. Chem. Soc., 116: 3143-3144 (1994).

Haringsma, H.J. et al., mRNA knockdown by single strand RNA is improved by chemical modifications, Nucleic Acids Research, 40(9): 4125-4136 (2012).

Hendrix, C. et al., 1',5'-Anhydrohexitol Oligonucleotides: Synthesis, Base Pairing and Recognition by Regular Oligodeoxyribonucleotides and Oligoribonucleotides, Chem. Eur. J., 3(1): 110-120 (1997).

Hirama, T. et al., PCR-Based Rapid Identification System Using Bridged Nucleic Acids for Detection of Clarithromycin-Resistant *Mycobacterium avium*-M. intracellulare Complex Isolates, Journal of Clinical Microbiology, 54(3): 699-704 (2016).

Hirose, M. et al., MDM4 expression as an indicator of TP53 reactivation by combined targeting of MDM2 and MDM4 in cancer cells without TP53 mutation, Oncoscience, 1(12): (2014).

Hu, J. et al., Allele-Selective Inhibition of Huntingtin Expression by Switching to an miRNA-like RNAi Mechanism, Chemistry & Biology 17: 1183-1188 (2010).

Hu, J. et al., Exploring the Effect of Sequence Length and Composition on Allele-Selective Inhibition of Human Huntingtin Expression by Single-Stranded Silencing RNAs, Nucleic Acid Therapeutics, 24(3): 199-209 (2014).

Hu, J. et al., Recognition of c9orf72 Mutant RNA by Single-Stranded Silencing RNAs, Nucleic Acid Therapeutics, 8 (2016). Supplementary Figure, 1 page.

Hyrup., B. and Nielsen, P.E., Peptide Nucleic Acids (PNA): Synthesis, Properties and Potential Applications, Bioorg. Med. Chem., 4(1): 5-23 (1996).

(56) References Cited

OTHER PUBLICATIONS

International Search Report for PCT/US2016/056123, 5 pages (dated Mar. 17, 2017).
Isis Pharmaceuticals, Inc. 2014 Annual Report, Improving Patients' Lives by Treating Disease Through Targeting RNA, 192 pages (2014).
*Isis Pharmaceuticals, Inc. v. Santaris Pharma A/S Corp.*, Order Denying Defendants' Motion For Summary Judgment Without Prejudice, Case No. 11cv02214 BTM (KSC), United States District Court, S.D. California, 5 pages (Sep. 19, 2012).
Jepsen, J.S. et al., Locked Nucleic Acid: A Potent Nucleic Acid Analog in Therapeutics and Biotechnology, Oligonucleotides,14: 130-146 (2004).
Jones, R.J. et al., Synthesis and binding properties of pyrimidine oligodeoxynucleoside analogs containing neutral phosphodiester replacements: The Formacetal and 3'-Thioformacetal Internucleoside Linkages, J. Org. Chem., 58: 2983-2991 (1993).
Kashida, H. et al., Acyclic artificial nucleic acids with phosphodiester bonds exhibit unique functions, Polymer Journal, 1-6 (2016).
Kay, C. et al., Personalized gene silencing therapeutics for Huntington disease, Clinical Genetics, 1-8 (2014).
Kim, D. et al., Immunostimulation and anti-DNA antibody production by backbone modified CpG-DNA, Biochemical and Biophysical Research Communications, 379(2): 362-367 (2009).
Kim, S-K. et al., Bridged Nucleic Acids (BNAs) as Molecular Tools, J Biochem Mol Biol Res., 1(3): 67-71 (2015).
Koch, T., A New Dimension in LNA Therapeutics, Roche Innovation Center, Copenhagen, Denmark, Presentation, 39 pages (May 3, 2017).
Koizumi, M. et al., Triplex formation with 2'-O,4'-C-ethylene-bridged nucleic acids (ENA) having C3'-endo conformation at physiological pH, Nuc. Acids Res., 31(12): 3267-3273 (2003).
Koseoglu, M. et al., Effects of hemolysis interference on routine biochemistry parameters. Biochemia Medica., 21(1): 79-85 (2011). Retrieved May 18, 2017, URL: <http://www.biochemia-medica.com/2011/21/79>.
Koshkin, A.A. et al., LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition, Tetrahedron 54: 3607-3630 (1998).
Kumar, R. et al., The First Analogues of LNA (Locked Nucleic Acids): Phosphorothioate-LNA and 2'-THIO-LNA, Bioo. Med. Chem. Let., 8: 2219-2222 (1998).
Lahiri, N., Shooting the messenger with single-stranded RNA gene silencing, edited by Wild, E., HDBuzz, 7 pages (Sep. 24, 2012). Retrieved Oct. 7, 2015. URL: http://en.hdbuzz.net/099.
Lauritsen, A. et al., Methylphosphonate LNA: A Locked Nucleic Acid with a Methylphosphonate Linkage, Chem. Comm., 13: 253-256 (2003).
Lauritsen, A. et al., Oligodeoxynucleotides containing amide-linked LNA-type dinucleotides: synthesis and high-affinity nucleic acid hybridization, Bioo. Med. Chem. Lett., 5: 530-531 (2002).
Liu, J. et al., Modulation of Splicing by Single-Stranded Silencing RNAs, Nucleic Acid Therapeutics, 25(3): 113-120 (2015).
Lopez, C. et al., Inhibition of AAC(6')-Ib-Mediated Resistance to Amikacin in Acinetobacter baumannii by an Antisense Peptide-Conjugated 2',4'- Bridged Nucleic Acid-NC-DNA Hybrid Oligomer, Antimicrobial Agents and Chemotherapy, 59(9): 5798-5803 (2015).
Martinez, J. et al., Single-Stranded Antisense siRNAs Guide Target RNA Cleavage in RNAi, Cell, 110: 563-574 (2002).
Martinez-Montero, S. et al., Locked 2'-Deoxy-2',4'-Difluororibo Modified Nucleic Acids: Thermal Stability, Structural Studies, and siRNA Activity, ACS Chem. Biol., 10: 2016?2023 (2015).
Matranga, C. et al., Passenger-Strand Cleavage Facilitates Assembly of siRNA into Ago2-Containing RNAi Enzyme Complexes, Cell, 123: 607-620 (2005). Supplemental Data, 6 pages.
Matsui, M. et al., Argonaute 2-dependent Regulation of Gene Expression by Single-stranded miRNA Mimics, Molecular Therapy, 10 pages (2016).

Matsui, M. et al., Transcriptional Silencing by Single-Stranded RNAs Targeting a Noncoding RNA That Overlaps a Gene Promoter, ACS Chem. Biol., 8: 122-126 (2013).
Meena, et al., Discovery and Early Clinical Development of the First Allele-Specific Stereopure ASO Drug Candidate with Disease—Modifying Potential for the Treatment of Huntington's Disease, WAVE Life Sciences, Poster, 1 page. (2016).
Mesmaeker, A.D. et al. Amides as a New Type of Backbone Modification in Oligonucleotides, Angew. Chem., Int. Ed. Engl., 33: 226-229 (1994).
Morita , K. et al., 2'-O,4'-C-Ethylene-bridged nucleic acids (ENA) with nucleaseresistance and high affnity for RNA, Nucl. Acids Res., Supp. 1: 241-242 (2001).
Morita , K. et al., 20-O,40-C-Ethylene-Bridged Nucleic Acids (ENA): Highly Nuclease-Resistant and Thermodynamically Stable Oligonucleotides for Antisense Drug, Bioo. Med. Chem. Lett., 12: 73-76 (2002).
Morita, K. et al., Synthesis and properties of 2?-O,4?-C-Ethylene-Bridged nucleic acids (ENA) as effective antisense oligonucleotides, Bioorganic & Medicinal Chemistry, 11(10): 2211-2226 (2003).
Nencka, R. et al., Novel Conformationally Locked Nucleosides and Nucleotides, Collection Sumposoim Series, 14: 119-122 (2014).
Nielsen, P.E. and Haaima, G., Peptide nucleic acid (PNA). A DNA mimic with a pseudopeptide backbone, Chem. Soc. Rev., 73-78 (1997).
Nielsen, P.E. et al., Sequence-Selective Recognition of DNA by Strang Displacement with a Thymine-Substituted Polyamide, Science, 254(5037): 1497-1500 (1991).
Nielsen, P.E. et al., Synthesis of 29-O,39-C-linked bicyclic nucleosides and bicyclic Oligonucleotides, J. Chem. Soc. Perkins Trans., 1: 3423-3433 (1997).
Obika et al. Stability and structural features of the duplexes containing nucleoside analogues with a fixed N-type conformation, 2'-O,4'- C-methyleneribonucleosides, Tetrahedron Lett. 39: 5401-5404 (1998).
Obika, S. et al., Synthesis of 2'-O,4'-C-Methyleneuridine and -cytidine. Novel Bicyclic Nucleosides Having a Fixed C a ,-endo Sugar Puckering, Tetrahedron Lett., 38(50): 8735-8 (1997).
Onizuka, K. et al., Short Interfering RNA Guide Strand Modifiers from Computational Screening, J. Am. Chem. Soc., 135: 17069-17077 (2013).
Osawa, T. et al., Synthesis and Properties of the 5-Methyluridine Derivative of 3,4-Dihydro-2H-pyran-Bridged Nucleic Acid (DpNA), J. Org. Chem., 80: 10474-10481 (2015).
Ostergaard, M.E. et al., Efficient Synthesis and Biological Evaluation of 5?-GalNAc Conjugated Antisense Oligonucleotides, Bioconjugate. Chem., 26: 1452-1455 (2015).
Pallan, P.S. et al., Structure and nuclease resistance of 20,40-constrained 20-O-methoxyethyl (cMOE) and 20-O-ethyl (cEt) modified DNAs, Chem. Comm., 48: 8195-8197 (2012).
Panzara, M. et al., Duchenne Muscular Dystrophy Advisory Board Meeting, WAVE Life Sciences, 70 pages (Mar. 3, 2017).
Parmer, R. et al., 5'-(E)-Vinylphosphonate: A Stable Phosphate Mimic Can Improve the RNAi Activity of siRNA-GalNAc Conjugates, Chem. Bio. Chem., 17: 1-6 (2016).
Pedersen, L. et al, A Kinetic Model Explains Why Shorter and Less Affine Enzyme-recruiting Oligonucleotides Can Be More Potent, Mol Ther Nucleic Acids, 3: e149 1-8 (2014).
Pendergraff, H.M. et al., Single-Stranded Silencing RNAs: Hit Rate and Chemical Modification, Nucleic Acid Therapeutics, 1-7 (2016).
Petersen, M. and Wengel, J., LNA: a versatile tool for therapeutics and genomics, TRENDS in Biotechnology, 21(2): 74-81 (2003).
Prakash, T.P. et al., Identification of metabolically stable 5-phosphate analogs that support single-stranded siRNA activity, Nucleic Acids Research, 43(6): 2993-3011 (2015). Supplementary Data, 80 pages.
Prakash, T.P. et al., Lipid Nanoparticles Improve Activity of Single-Stranded siRNA and Gapmer Antisense Oligonucleotides in Animals, ACS Chem. Biol., 5 pages (2013).

(56) References Cited

OTHER PUBLICATIONS

Prakash, T.P. et al., Synergistic effect of phosphorothioate, 50-vinylphosphonate and GalNAc modifications for enhancing activity of synthetic siRNA, Bioorg. Med. Chem. Lett., 26: 2817-2820 (2016).

Prakash, T.P. et al., Targeted delivery of antisense oligonucleotides to hepatocytes using triantennary N-acetyl galactosamine improves potency 10-fold in mice, Nucleic Acids Res., 42(13): 8796-807 (2014).

Rajwanshi, V.K. et al., LNA stereoisomers: xylo-LNA (b-d-xylo configured locked nucleic acid) and a-l-LNA (a-l-ribo configured locked nucleic acid), Chem. Commun., 1395-1396 (1999).

Ravn, J. et al., Stereodefined LNA Phosphorthioate Oligonucleotides, Roche Pharma Research and Early Development, RTR Research, Roche Innovation Center Copenhagen, RNA & Oligonucleotide Therapeutics Meeting, Poster, 1 page. (Mar. 29-Apr. 1, 2017).

Saetrom, P., Predicting the efficacy of short oligonucleotides in antisense and RNAi experiments with boosted genetic programming, Bioinformatics, 20(17): 3055-3063 (2004).

Sanhueza, C.A. et al., Efficient Liver Targeting by Polyvalent Display of a Compact Ligand for the Asialoglycoprotein Receptor, J. Am. Chem. Soc., 9 pages (2016).

Schirle, N. T. and Macrae, I.J., The Crystal Structure of Human Argonaute2, Science, 336(6084): 1037-1040 (2012).

Schirle, N.T. et al., Structural analysis of human Argonaute-2 bound to a modified siRNA guide, J. Am. Chem. Soc., 1-6 (2016).

Schirle, N.T. et al., Structural Basis for microRNA Targeting, Science, 346(6209): 608-613 (2014).

Schirle, N.T. et al., Water-mediated recognition of t1-adenosine anchors Argonaute2 to microRNA targets, eLife, 4: e07646 1-16 (2015).

Schultz, R.G. and Gryaznov, S.M., Oligo-2'-fluoro-2'-deoxynucleotide N3'→P5' phosphoramidates: synthesis and properties, Nucleic Acids Res., 24(15): 2966-2973 (1996).

Seth, P.P. et al., Configuration of the 5'-Methyl Group Modulates the Biophysical and Biological Properties of Locked Nucleic Acid (LNA) Oligonucleotides, J. Med. Chem., 53: 8309-8318 (2010).

Seth, P.P. et al., Design, Synthesis and Evaluation of Constrained Methoxyethyl, (cMOE) and Constrained Ethyl (cEt) Nucleoside Analogs, Nucleic Acids Symposium Series, 52(1), 553-554 (2008).

Seth, P.P. et al., Short Antisense Oligonucleotides with Novel 2'-4' Conformationaly Restricted Nucleoside Analogues Show Improved Potency without Increased Toxicity in Animals, J. Med. Chem., 52: 10-13 (2009).

Seth, P.P. et al., Structural requirements for hybridization at the 5'-position are different in a-L-LNA as compared to b-D-LNA, Bioo. Med. Chem. Lett., 22: 296-299 (2012).

Seth, P.P. et al., Structure Activity Relationships of $\alpha$-l-LNA Modified, Phosphorothioate Gapmer Antisense Oligonucleotides in Animals, Mol. Ther-Nuc. Acids., 1: e47 1-8 (2012).

Seth, P.P. et al., Synthesis and Biophysical Evaluation of 2',4'-Constrained 2'O-Methoxyethyl and 2',4'-Constrained 2'O-Ethyl Nucleic Acid Analogues, J. Org. Chem., 75: 1569-1581 (2010).

Singh, P.P. et al., Universality of LNA-mediated high-affinity nucleic acid recognition, Chem. Comm., 1247-1248 (1998).

Singh, S.K. et al., Synthesis of 2'-Amino-LNA: A Novel Conformationally Restricted High-Affinity Oligonucleotide Analogue with a Handle, J. Org. Chem., 63: 10035-10039 (1998).

Singh, S.K. et al., Synthesis of Novel Bicyclo[2.2.1] Ribonucleosides: 2'-Amino- and 2'-Thio-LNA Monomeric Nucleosides, J. Org. Chem., 63: 6078-6079 (1998).

Sorensen, M.D., Functionalized LNA (locked nucleic acid): high-affinity hybridization of oligonucleotides containing N-acylated and N-alkylated 2'-amino-LNA monomers, Chem. Comm., 2130-2131 (2003).

Suter, S.R. et al., Structure-Guided Control of siRNA Off Target Effects, J. Am. Chem. Soc., 1-9 (2016).

Takahashi, T. et al., Interactions between the non-seed region of siRNA and RNA-binding RLC/RISC proteins, Ago and TRBP, in mammalian cells, Nucleic Acids Research, 42(8): 5256-5269 (2014).

Ts'O, P.O. et al., An Approach to Chemotherapy Based on Base Sequence Information and Nucleic Acid Chemistry, Ann. N. Y. Acad. Sci., 507: 220-241 (1988).

U.S. Food & Drug Administration, Development of New Stereoisomeric Drugs, Guidance, Compliance & Regulatory Information, Guidances (Drugs), Publication Date: May 1, 1992, 8 pages. Retrieved May 17, 2017 URL: http://www.fda.gov/Drugs/GuidanceComplianceRegulatoryInformation/Guidances/ucm122883.htm.

Van Aerschot, A. et al., 1,5-Anhydrohexitol Nucleic Acids, a New Promising Antisense Construc, Angew. Chem. Int. Ed. Engl., 34: 1338-1339 (1995).

Vasseur, J-J. et al., Oligonucleosides: Synthesis of a Novel Methylhydroxylamine-Linked Nucleoside Dimer and Its Incorporation into Antisense Sequences, J. Am. Chem. Soc., 114: 4006-4007 (1992).

Veedu, R.N. et al., Novel Applications of Locked Nucleic Acids, Nucleic Acids Symposium Series, 51: 29-30 (2007).

Wang, Y. et al., Structure of an argonaute silencing complex with a seed-containing guide DNA and target RNA duplex, Nature, 456(7224): 921-926 (2008).

Watts, J.K. and Corey, D.R., Gene silencing by siRNAs and antisense oligonucleotides in the laboratory and the clinic, J. Pathol. 226(2): 365-79 (2012).

Weinfeld, M., et al., Influence of nucleic acid base aromaticity on substrate reactivity with enzymes acting on single-stranded DNA, Nucleic Acids Res., 21(3): 621-626 (1993).

Whittaker, B. et al., Stereoselective synthesis of highly functionalised P-stereogenic nucleosides via palladium-catalysed P-C cross-coupling reactions, Tetrahedron Letters, 49: 6984-6987 (2008).

Written Opinion for PCT/US2016/056123, 15 pages (dated Mar. 17, 2017).

Xu, Y. et al., Functional comparison of single- and double-stranded siRNAs in mammalian cells, Biochemical and Biophysical Research Communications, 316: 680-687 (2004).

Zhang, Y. et al., Structural Isosteres of Phosphate Groups in the Protein Data Bank, J. Chem. Inf. Model, 1-18 (2017).

Zhang, Y., Investigating phosphate structural replacements through computational and experimental approaches, Academic Dissertan, University of Helsinki, 119 pages (2014).

Zhong, Z. et al., WAVE Life Sciences: Developing Stereopure Nucleic Acid Therapies for the Treatment of Genetic Neurological Diseases, World CNS Summit 2017, Boston, MA, WAVE Life Sciences, Poster, 1 page (Feb. 20-22, 2017).

Zlatev, I. et al., 5'LCL Malonyl RNA: Small Interfering RNAs Modified with 5'- Monophosphate Bioisostere Demonstrate Gene Silencing Activity, ACS Chem. Biol., 8 pages (2015).

Jepsen, J.S. et al., LNA-Antisense Rivals Sirna for Gene Silencing, Current Opinion in Drug Discovery and Development, 7(2): 188-194 (2004).

Aartsma-Rus, A. et al., Antisense-Induced Multiexon Skipping for Duchenne Muscular Dystrophy Makes More Sense, Am. J. Hum. Genet., 74:83-92 (2004).

Aartsma-Rus, A. et al., Therapeutic antisense-induced exon skipping in cultured muscle cells from six different DMD patients, Human Molecular Genetics, 12(8):907-914 (2003).

Birts, C.N. et a., Transcription of Click-Linked DNA un Human Cells, Angew. Chem. Int. Ed., 53:2362-2365 (2014).

Chan, J.H.P. et al., Antisense Oligonucleotides: From Design to Therapeutic Application, Clinical and Experimental Pharmacology and Physiology, 33: 544-540 (2006).

Chmielewski, M.K. and Markiewicz, W.T., Novel Method of Synthesis of 5"-Phosphate 2'-O-ribosyl-ribonucleosides and Their 3'-Phosphoramidites, Molecules, 18:14780-14796 (2013).

Cieslak, J. et al., 31P NMR Study of the Desulfurization of Oligonucleoside Phosphorothioates Effected by "Aged" Trichloroacetic Acid Solutions, J. Org. Chem., 70: 3303-3306 (2005).

Crooke, S.T., Antisense Strategies, Current Molecular Medicine, 4: 465-487 (2004).

(56) References Cited

OTHER PUBLICATIONS

Crooke, S.T., Progress in Antisense Technology, Annu. Rev. Med., 55: 61-95 (2004).
DeJesus-Hernandez, M. et al., Expanded GGGGCC hexanucleotide repeat in non-coding region of C9ORF72 causes chromosome 9p-linked frontotemporal dementia and amyotrophic lateral sclerosis, Neuron, 72(2): 245-256 (2011).
Donnelly, C.J. et al., RNA Toxicity from the ALS/FTD C90RF72 Expansion Is Mitigated by antisense Intervention, Neuron, 80:415-428 (2013).
Efimov, V.A. et al., Rapid synthesis of long-chain deoxyribooligonucleotides by the N-methylimidazolide phosphotriester method, Nucleic Acids Research, 11(23): 8369-8387 (1983).
El-Sagheer, A.H. and Brown, T., Efficient RNA synthesis by in vitro transcription of a triazole-modified DNA template, Chem. Commun., 47(44):12057-12058 (2011).
El-Sagheer, A.H. and Brown, T., New strategy for the synthesis of chemically modified RNA constructs exemplified by hairpin and hammerhead ribozymes, PNAS, 107(35):15329-15334 (2010).
El-Sagheer, A.H. et al., Biocompatible artificial DNA linker that is read through by DNA polymerases and is functional in *Escherichia coli*, PNAS, 108(28):11338-11343 (2011).
Hagedorn, P.H. et al., Locked nucleic acid: modality, diversity, and drug discovery, Drug Discovery, 1-14 (Oct. 2017).
Heemskerk, H.A. et al., In vivo comparison of 2'-O-methyl phosphorothioate and morpholino antisense oligonucleotides for Duchenne muscular dystrophy exon skipping, The Journal of Gene Medicine, 11:257-266 (2009).
International Search Report for PCT/US2017/022135, 3 pages (dated Jun. 6, 2017).
International Search Report for PCT/US2017/030753, 6 pages (dated Sep. 26, 2017).
International Search Report for PCT/US2017/030777, 5 pages (dated Oct. 2, 2017).
International Search Report for PCT/US2017/035837, 4 pages (dated Aug. 24, 2017).
International Search Report for PCT/US2017/043431, ISA/US, 5 pages (dated Dec. 21, 2017).
International Search Report for PCT/US2017/045218, 3 pages (date Sep. 27, 2017).
Iwamoto, N. et al., Control of phosphorothioate stereochemistry substantially increases the efficacy of antisense oligonucleotides, Nature Biotechnology, Life Sciences Reporting Summary, 6 pages (2017).
Iwamoto, N. et al., Control of phosphorothioate stereochemistry substantially increases the efficacy of antisense oligonucleotides, Nature Biotechnology, pp. 1-9 (2017).
Iwamoto, N. et al., Control of phosphorothioate stereochemistry substantially increases the efficacy of antisense oligonucleotides, Nature Biotechnology, Supplementary Methods, Supplementary Tables 1-4, and Supplementary Note, 23 pages (2017).
Iwamoto, N. et al., Control of phosphorothioate stereochemistry substantially increases the efficacy of antisense oligonucleotides, Nature Biotechnology, Supplementary Text and Figures 1-9, 13 pages (2017).
Iwamoto, N. et al., Control of phosphorothioate stereochemistry substantially increases the efficacy of antisense oligonucleotides, Nature Biotechnology, with Supplemental Data, 19 pages (2017).
Kretschmer-Kazemi Far, R. and Sczakiel, G., The activity of siRNA in mammalian cells is related to structural target accessibility: a comparison with antisense oligonucleotides, Nucleic Acids Research, 31(15):4417-4424 (2003).
Krieg, A.M., Therapeutic potential of Toll-like receptor 9 activation, Nature Reviews, 471-484 (2006).
Krotz, A.H. et al., Phosphorothioate Oligonucleotides with Low Phosphate Diester Content: Greater than 99.9% Sulfurization Efficiency with "Aged" Solutions of Phenylacetyl Disulfide (PADS), Organic Process Research & Development, 8: 852-858 (2004).
Leviten, M., Wave'S Purity Progress, Biocentury, 1-6 (Sep. 28, 2017).
Li, M. et al., Synthesis and cellular activity of stereochemically-pure 2'-O-(2-methoxyethyl)-phosphorothioate oligonucleotides, Chem. Commun., 53: 541-544 (2017).
Midturi, J. et al., Spectrum of Pulmonary Toxicity Associated with the Use of Interferon Therapy for Hepatitis C: Case Report and Review of the Literature, Clinical Infectious Diseases, 39(11): 1724-1729 (2004).
Pontarollo, R.A. et al., Monocytes are required for optimum in vitro stimulation of bovine peripheral blood mononuclear cells by non-methylated CpG motifs, Veterinary Immunology and Immunopathology, 84(1-2): 43-59 (2002).
Shivalingam, A. et al., Molecular Requirements of High-Fidelity Replication-Competent DNA Backbones for Orthogonal Chemical Ligation, J. Am. Chem. Soc., 139(4):1575-1583 (2017).
Sobkowski, M. et al., Recent Advances in H-Phosphonate Chemistry. Part 1. H-Phosphonate Esters: Synthesis and Basic Reactions, Top Curr Chem, 361:137-177 (2014).
Stout, A.K. et al., Inhibition of wound healing in mice by local interferon a/b injection, Int J Exp Pathol, 74 (1): 79-85 (1993).
Surono, A. et al., Chimeric RNA/Ethylene Bridged Nucleic Acids Promote Dystrophin Expression in Myocytes of Duchenne Muscular Dystrophy by Inducing Skipping of the Nonsense Mutation-Encoding Econ, Human Gene Therapy, 15:749-757 (2004).
Takeshima, Y. et al., Oligonucleotides against a splicing enhancer sequence led to dystrophin production in muscle cells from a Duchenne muscular dystrophy patient, Brain & Development, 23:788-790 (2001).
Van Deutekom, J.C.T. et al., Antisense-induced exon skipping restores dystrophin expression in DMD patient derived muscle cells, Human Molecular Genetics, 10(15):1547-1554 (2001).
Weiner, G. J. et al., Immunostimulatory oligodeoxynucleotides containing the CpG motif are effective as immune adjuvants in tumor antigen immunization, 94(20): 10833-10837 (1997).
Woolf, T.M. et al., Specificity of antisense oligonucleotides in vivo, Prov. Natl. Aca. Sci. USA, 89: 7305-7309 (1992).
Written Opinion for PCT/US2017/022135, 11 pages (dated Jun. 6, 2017).
Written Opinion for PCT/US2017/030753, 13 pages (dated Sep. 26, 2017).
Written Opinion for PCT/US2017/030777, 10 pages (dated Oct. 2, 2017).
Written Opinion for PCT/US2017/035837, 15 pages (dated Aug. 24, 2017).
Written Opinion for PCT/US2017/043431, ISA/US, 38 pages (dated Dec. 21, 2017).
Written Opinion for PCT/US2017/045218, 11 pages (dated Sep. 27, 2017).
Yasuda, K. et al., CpG motif-independent activation of TLR9 upon endosomal translocation of "natural" phosphodiester DNA, European Journal of Immunology, 431-436 (2006).
Ye, S. et al., An efficient procedure for genotyping single nucleotide polymorphisms, Nucleic Acids Research, 29(17): e88 1-8 (2001).

* cited by examiner

SEQUENCE LISTING

```
<160> NUMBER OF SEQ ID NOS: 119

<210> SEQ ID NO 1
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
``` phosphorothioate linkages
<220> FEATURE:
<221> NAME/KEY: misc_feature
<222> LOCATION: (16)..(19)
<223> OTHER INFORMATION: wherein all the internucleotide linkages are
       phosphorothioate linkages

<400> SEQUENCE: 1
tcgtcgtttt gtcgttttgt cggg                                           24

<210> SEQ ID NO 2
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
       phosphorothioate linkages
<220> FEATURE:
<221> NAME/KEY: misc_feature
<222> LOCATION: (8)..(11)
<223> OTHER INFORMATION: wherein all the internucleotide linkages are
       phosphorothioate linkages
<220> FEATURE:
<221> NAME/KEY: misc_feature
<222> LOCATION: (16)..(19)
<223> OTHER INFORMATION: wherein all the internucleotide linkages are
       phosphorothioate linkages

<400> SEQUENCE: 2
gggtcgtttt gtcgttttgt cggg                                           24

<210> SEQ ID NO 3
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
       phosphorothioate linkages
<220> FEATURE:
<221> NAME/KEY: misc_feature
<222> LOCATION: (8)..(11)
<223> OTHER INFORMATION: wherein all the internucleotide linkages are
       phosphorothioate linkages
<220> FEATURE:
<221> NAME/KEY: misc_feature
<222> LOCATION: (16)..(18)
<223> OTHER INFORMATION: wherein all the internucleotide linkages are
       phosphorothioate linkages

<400> SEQUENCE: 3
tcaacgtttc aacgtttt                                                  18

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
       phosphorothioate linkages
<220> FEATURE:
<221> NAME/KEY: misc_feature

```
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages

<400> SEQUENCE: 4
tcaacgtttc aacgttttgg                                                 20

<210> SEQ ID NO 5
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(18)
<223> OTHER INFORMATION: wherein all the internucleotide linkages are
      phosphorothioate linkages

<400> SEQUENCE: 5
tcaacgtttc aacgttgg                                                   18

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(20)
<223> OTHER INFORMATION: wherein all the internucleotide linkages are
      phosphorothioate linkages

<400> SEQUENCE: 6
tcaacgtttc aacgttgggg                                                 20

<210> SEQ ID NO 7
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
```

```
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages

<400> SEQUENCE: 7
tcaacgtttt aacgttttaa cggg                                          24

<210> SEQ ID NO 8
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (15)..(17)
<223> OTHER INFORMATION: wherein all the internucleotide linkages are
      phosphorothioate linkages

<400> SEQUENCE: 8
tcaacgttta acgtttt                                                  17

<210> SEQ ID NO 9
<211> LENGTH: 16
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (7)..(8)
<223> OTHER INFORMATION: wherein all the internucleotide linkages are
      phosphorothioate linkages
<220> FEATURE:
<221> NAME/KEY: misc_feature
<222> LOCATION: (14)..(16)
<223> OTHER INFORMATION: wherein all the internucleotide linkages are
      phosphorothioate linkages

<400> SEQUENCE: 9
tcaacgttaa cgtttt                                                   16

<210> SEQ ID NO 10
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
```

```
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages

<400> SEQUENCE: 10
tcaacgttta aacgtttaaa cggg                                          24

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages

<400> SEQUENCE: 11
tcaacgttaa cgttaacggg                                               20

<210> SEQ ID NO 12
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages

<400> SEQUENCE: 12
tcgacgtttt gacgttttga cggg                                          24

<210> SEQ ID NO 13
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
```

<221> NAME/KEY: misc_feature
<222> LOCATION: (16)..(19)
<223> OTHER INFORMATION: wherein all the internucleotide linkages are
      phosphorothioate linkages with Sp Chirality

<400> SEQUENCE: 13
tcgacgtttt gacgttttga cggg                                          24

<210> SEQ ID NO 14
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Rp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Rp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Rp Chirality

<400> SEQUENCE: 14
tcgacgtttt gacgttttga cggg                                          24

<210> SEQ ID NO 15
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (7)..(10)
<223> OTHER INFORMATION: wherein all the internucleotide linkages are
      phosphorothioate linkages
<220> FEATURE:
<221> NAME/KEY: misc_feature
<222> LOCATION: (15)..(18)
<223> OTHER INFORMATION: wherein all the internucleotide linkages are
      phosphorothioate linkages

<400> SEQUENCE: 15
gggacgtttt gacgttttga cggggg                                        26

<210> SEQ ID NO 16
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (7)..(10)
<223> OTHER INFORMATION: wherein all the internucleotide linkages are

```
      phosphorothioate linkages
<220> FEATURE:
<221> NAME/KEY: misc_feature
<222> LOCATION: (15)..(18)
<223> OTHER INFORMATION: wherein all the internucleotide linkages are
      phosphorothioate linkages
<220> FEATURE:
<221> NAME/KEY: misc_feature
<222> LOCATION: (23)..(26)
<223> OTHER INFORMATION: wherein all the internucleotide linkages are
      phosphorothioate linkages

<400> SEQUENCE: 16
tcgacgtttt gacgttttga cgttttgacg gg                                    32

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (7)..(9)
<223> OTHER INFORMATION: wherein all the internucleotide linkages are
      phosphorothioate linkages
<220> FEATURE:
<221> NAME/KEY: misc_feature
<222> LOCATION: (13)..(15)
<223> OTHER INFORMATION: wherein all the internucleotide linkages are
      phosphorothioate linkages

<400> SEQUENCE: 17
tcgacgttga cgttgacggg                                                  20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Sp Chirality

<400> SEQUENCE: 18
tcgacgttga cgttgacggg                                                  20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
```

```
<222> LOCATION: (1)..(3)
<223> OTHER INFORMATION: wherein all the internucleotide linkages are
      phosphorothioate linkages with Rp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Rp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Rp Chirality

<400> SEQUENCE: 19
tcgacgttga cgttgacggg                                                   20

<210> SEQ ID NO 20
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (7)..(9)
<223> OTHER INFORMATION: wherein all the internucleotide linkages are
      phosphorothioate linkages
<220> FEATURE:
<221> NAME/KEY: misc_feature
<222> LOCATION: (13)..(15)
<223> OTHER INFORMATION: wherein all the internucleotide linkages are
      phosphorothioate linkages
<220> FEATURE:
<221> NAME/KEY: misc_feature
<222> LOCATION: (19)..(21)
<223> OTHER INFORMATION: wherein all the internucleotide linkages are
      phosphorothioate linkages

<400> SEQUENCE: 20
tcgacgttga cgttgacgtt gacggg                                            26

<210> SEQ ID NO 21
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (24)..(27)
<223> OTHER INFORMATION: wherein all the internucleotide linkages are
      phosphorothioate linkages

<400> SEQUENCE: 21
```
tcgacgttta aacgtttaaa cgtttaaacg gg            32

<210> SEQ ID NO 22
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (24)..(27)
<223> OTHER INFORMATION: wherein all the internucleotide linkages are
      phosphorothioate linkages

<400> SEQUENCE: 22
tcgacgttta aacgtttaga cgtttaaacg gg            32

<210> SEQ ID NO 23
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages

<400> SEQUENCE: 23
tcgacgttaa cgttaacgtt aacggg            26

<210> SEQ ID NO 24
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(11)
<223> OTHER INFORMATION: wherein all the internucleotide linkages are
      phosphorothioate linkages

<400> SEQUENCE: 24
gggacgttta aacgtctaga cggg            24

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)

```
<223> OTHER INFORMATION: wherein all the internucleotide linkages are
      phosphorothioate linkages
<220> FEATURE:
<221> NAME/KEY: misc_feature
<222> LOCATION: (7)..(8)
<223> OTHER INFORMATION: wherein all the internucleotide linkages are
      phosphorothioate linkages
<220> FEATURE:
<221> NAME/KEY: misc_feature
<222> LOCATION: (11)..(12)
<223> OTHER INFORMATION: wherein all the internucleotide linkages are
      phosphorothioate linkages
<220> FEATURE:
<221> NAME/KEY: misc_feature
<222> LOCATION: (15)..(16)
<223> OTHER INFORMATION: wherein all the internucleotide linkages are
      phosphorothioate linkages

<400> SEQUENCE: 25
tcgacgtacg tacgtacggg                                              20

<210> SEQ ID NO 26
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (22)..(24)
<223> OTHER INFORMATION: wherein all the internucleotide linkages are
      phosphorothioate linkages

<400> SEQUENCE: 26
tcgacgtttt gacgttttga cggg                                         24

<210> SEQ ID NO 27
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
```

```
<223> OTHER INFORMATION: wherein all the internucleotide linkages are
      phosphorothioate linkages with Sp Chirality

<400> SEQUENCE: 27
tcgacgtttt gacgttttga cggg                                              24

<210> SEQ ID NO 28
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Rp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Rp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Rp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Rp Chirality

<400> SEQUENCE: 28
tcgacgtttt gacgttttga cggg                                              24

<210> SEQ ID NO 29
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (23)..(25)
<223> OTHER INFORMATION: wherein all the internucleotide linkages are
      phosphorothioate linkages

<400> SEQUENCE: 29
tcgacgtttt gacgttttga cgggg                                             25

<210> SEQ ID NO 30
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
```

```
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (23)..(25)
<223> OTHER INFORMATION: wherein all the internucleotide linkages are
      phosphorothioate linkages

<400> SEQUENCE: 30
tcgacgtttt gacgttttga cgtgg                                           25

<210> SEQ ID NO 31
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (24)..(26)
<223> OTHER INFORMATION: wherein all the internucleotide linkages are
      phosphorothioate linkages

<400> SEQUENCE: 31
tcgacgtttt gacgttttga cgtggg                                          26

<210> SEQ ID NO 32
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(24)
<223> OTHER INFORMATION: wherein all the internucleotide linkages are
      phosphorothioate linkages
```

<400> SEQUENCE: 32
tcgacgtttt gacgttttga cggg         24

<210> SEQ ID NO 33
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (23)..(27)
<223> OTHER INFORMATION: wherein all the internucleotide linkages are
      phosphorothioate linkages

<400> SEQUENCE: 33
tcgacgtttt gacgttttga cggggggg     27

<210> SEQ ID NO 34
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (23)..(27)
<223> OTHER INFORMATION: wherein all the internucleotide linkages are
      phosphorothioate linkages with Sp Chirality

<400> SEQUENCE: 34
tcgacgtttt gacgttttga cggggggg     27

<210> SEQ ID NO 35
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are

```
          phosphorothioate linkages with Rp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Rp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Rp Chirality
<220> FEATURE:
<221> NAME/KEY: misc_feature
<222> LOCATION: (23)..(27)
<223> OTHER INFORMATION: wherein all the internucleotide linkages are
      phosphorothioate linkages with Rp Chirality

<400> SEQUENCE: 35
tcgacgtttt gacgttttga cgggggg                                            27

<210> SEQ ID NO 36
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages
<220> FEATURE:
<221> NAME/KEY: misc_feature
<222> LOCATION: (22)..(26)
<223> OTHER INFORMATION: wherein all the internucleotide linkages are
      phosphorothioate linkages

<400> SEQUENCE: 36
tcgacgtttt gacgttttga cggggg                                             26

<210> SEQ ID NO 37
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (7)..(9)
<223> OTHER INFORMATION: wherein all the internucleotide linkages are
      phosphorothioate linkages
<220> FEATURE:
<221> NAME/KEY: misc_feature
<222> LOCATION: (13)..(15)
<223> OTHER INFORMATION: wherein all the internucleotide linkages are
      phosphorothioate linkages
<220> FEATURE:
<221> NAME/KEY: misc_feature
<222> LOCATION: (20)..(22)
<223> OTHER INFORMATION: wherein all the internucleotide linkages are
``` phosphorothioate linkages

<400> SEQUENCE: 37
tcgacgttga cgttgacgtg gg                                          22

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(6)
<223> OTHER INFORMATION: wherein all the internucleotide linkages are
      phosphorothioate linkages
<220> FEATURE:
<221> NAME/KEY: misc_feature
<222> LOCATION: (11)..(20)
<223> OTHER INFORMATION: wherein all the internucleotide linkages are
      phosphorothioate linkages

<400> SEQUENCE: 38
ggtgcatcga tgcagggggg                                             20

<210> SEQ ID NO 39
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (8)..(11)
<223> OTHER INFORMATION: wherein all the internucleotide linkages are
      phosphorothioate linkages
<220> FEATURE:
<221> NAME/KEY: misc_feature
<222> LOCATION: (16)..(19)
<223> OTHER INFORMATION: wherein all the internucleotide linkages are
      phosphorothioate linkages

<400> SEQUENCE: 39
tcatcgattt atcgatttat cggg                                        24

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(6)
<223> OTHER INFORMATION: wherein all the internucleotide linkages are
      phosphorothioate linkages
<220> FEATURE:
<221> NAME/KEY: misc_feature
<222> LOCATION: (11)..(20)
<223> OTHER INFORMATION: wherein all the internucleotide linkages are
      phosphorothioate linkages

<400> SEQUENCE: 40
ggtgcgacga tgcagggggg                                             20

<210> SEQ ID NO 41

```
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(5)
<223> OTHER INFORMATION: wherein all the internucleotide linkages are
      phosphorothioate linkages
<220> FEATURE:
<221> NAME/KEY: misc_feature
<222> LOCATION: (17)..(20)
<223> OTHER INFORMATION: wherein all the internucleotide linkages are
      phosphorothioate linkages

<400> SEQUENCE: 41
gggggacgat cgtcgggggg                                                  20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (15)..(20)
<223> OTHER INFORMATION: wherein all the internucleotide linkages are
      phosphorothioate linkages

<400> SEQUENCE: 42
gggacgatat cgtcgggggg                                                  20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (15)..(20)
<223> OTHER INFORMATION: wherein all the internucleotide linkages are
      phosphorothioate linkages

<400> SEQUENCE: 43
gggacgacgt cgtcgggggg                                                  20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
```

<223> OTHER INFORMATION: wherein all the internucleotide linkages are
      phosphorothioate linkages with Sp Chirality

<400> SEQUENCE: 44
gggacgacgt cgtcgggggg                                                     20

<210> SEQ ID NO 45
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Rp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Rp Chirality

<400> SEQUENCE: 45
gggacgacgt cgtcgggggg                                                     20

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (15)..(20)
<223> OTHER INFORMATION: wherein all the internucleotide linkages are
      phosphorothioate linkages

<400> SEQUENCE: 46
gggggacgat cgtcgggggg                                                     20

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages
<220> FEATURE:
<221> NAME/KEY: misc_feature
<222> LOCATION: (13)..(20)
<223> OTHER INFORMATION: wherein all the internucleotide linkages are
      phosphorothioate linkages

<400> SEQUENCE: 47
gggacgcgcg tcggggggggg                                                    20

<210> SEQ ID NO 48
<211> LENGTH: 14
<212> TYPE: DNA
<213> ORGANISM: Artificial Sequence
<220> FEATURE:

```
<223> OTHER INFORMATION: Synthetic Oligonucleotide
<220> FEATURE:
<221> NAME/KEY: misc_feature
<222> LOCATION: (1)..(5)
<223> OTHER INFORMATION: wherein all the internucleotide linkages are
      phosphorothioate linkages
<220> FEATURE:
<221> NAME/KEY: misc_feature
<222> LOCATION: (11)..(14)
<223> OTHER INFORMATION: wherein all the internucleotide linkages are
      phosphorothioate linkages

<400> SEQUENCE: 48
ggggtcgttc gggg                                                         14

<210> SEQ ID NO 49
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 49
tcatcgattt atcgatttaa cggg                                              24

<210> SEQ ID NO 50
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 50
tcgacgtttt gacgttttga cggg                                              24

<210> SEQ ID NO 51
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
```

```
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (18)..(24)
<223> OTHER INFORMATION: wherein all the internucleotide linkages are
      phosphorothioate linkages with Sp Chirality

<400> SEQUENCE: 51
tcgacgtttt gacgttttga cggg                                           24

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (19)..(20)
<223> OTHER INFORMATION: wherein all the internucleotide linkages are
      phosphorothioate linkages with Sp Chirality

<400> SEQUENCE: 52
tcgacgttga cgttgacggg                                                20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (18)..(20)
<223> OTHER INFORMATION: wherein all the internucleotide linkages are
      phosphorothioate linkages with Sp Chirality

<400> SEQUENCE: 53
tcgacgttga cgttgacggg                                                20

<210> SEQ ID NO 54
```

```
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (19)..(21)
<223> OTHER INFORMATION: wherein all the internucleotide linkages are
      phosphorothioate linkages with Sp Chirality

<400> SEQUENCE: 54
tcgacgttga cgttgacggg g                                           21

<210> SEQ ID NO 55
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (18)..(19)
<223> OTHER INFORMATION: wherein all the internucleotide linkages are
      phosphorothioate linkages with Sp Chirality

<400> SEQUENCE: 55
tcgacgttga cgttgactg                                              19

<210> SEQ ID NO 56
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
```

```
<220> FEATURE:
<221> NAME/KEY: misc_feature
<222> LOCATION: (13)..(20)
<223> OTHER INFORMATION: wherein all the internucleotide linkages are
      phosphorothioate linkages with Sp Chirality

<400> SEQUENCE: 56
tcgacgttga cgttgacggg                                                    20

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(20)
<223> OTHER INFORMATION: wherein all the internucleotide linkages are
      phosphorothioate linkages with Sp Chirality

<400> SEQUENCE: 57
tcgacgttga cgttgacggg                                                    20

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(20)
<223> OTHER INFORMATION: wherein all the internucleotide linkages are
      phosphorothioate linkages with Sp Chirality

<400> SEQUENCE: 58
tcatcgatat cgatgacggg                                                    20

<210> SEQ ID NO 59
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (18)..(21)
```

<223> OTHER INFORMATION: wherein all the internucleotide linkages are
      phosphorothioate linkages with Sp Chirality

<400> SEQUENCE: 59
tcgacgttga cgttgacggg g                                               21

<210> SEQ ID NO 60
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(23)
<223> OTHER INFORMATION: wherein all the internucleotide linkages are
      phosphorothioate linkages with Sp Chirality

<400> SEQUENCE: 60
tcgacgtttt gacgttttgg ggg                                             23

<210> SEQ ID NO 61
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 61
tcgacgtttt gacgttttga gggg                                            24

<210> SEQ ID NO 62
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:

```
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 62
tcgacgtttt gacgttttgt gggg                                            24

<210> SEQ ID NO 63
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(10)
<223> OTHER INFORMATION: wherein all the internucleotide linkages are
      phosphorothioate linkages with Sp Chirality
<220> FEATURE:
<221> NAME/KEY: misc_feature
<222> LOCATION: (14)..(20)
<223> OTHER INFORMATION: wherein all the internucleotide linkages are
      phosphorothioate linkages with Sp Chirality

<400> SEQUENCE: 63
tcgacgttga cgttgacggg                                                 20

<210> SEQ ID NO 64
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 64
ccgacgtttt gacgttttga cggg                                            24

<210> SEQ ID NO 65
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
``` phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
       phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
       phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
       phosphorothioate linkages with Sp Chirality

<400> SEQUENCE: 65
tcgacgttta gacgtttaga cggg                                               24

<210> SEQ ID NO 66
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
       phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
       phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
       phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
       phosphorothioate linkages with Sp Chirality

<400> SEQUENCE: 66
tcgacgtttt gacgttttga cgaa                                               24

<210> SEQ ID NO 67
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
       phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
       phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
       phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are phosphorothioate linkages with Sp Chirality

<400> SEQUENCE: 67
tcgacgtttt gacgttttga cgtt                                           24

<210> SEQ ID NO 68
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 68
tcaacgtttt aacgttttga cggg                                           24

<210> SEQ ID NO 69
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality

<400> SEQUENCE: 69
tcgacgtttt gacgttttgg g                                              21

<210> SEQ ID NO 70
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality

<400> SEQUENCE: 70
tcgacgtttt gacgttttga cgttgg                                    26

<210> SEQ ID NO 71
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (14)..(17)
<223> OTHER INFORMATION: wherein all the internucleotide linkages are
      phosphorothioate linkages with Sp Chirality

<400> SEQUENCE: 71
tcgacgttga cgttggg                                              17

<210> SEQ ID NO 72
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(12)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(20)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 72
tcgacgtttt gacgttttga cggg                                      24

<210> SEQ ID NO 73
<211> LENGTH: 24
<212> TYPE: DNA
<213> ORGANISM: Artificial Sequence
<220> FEATURE:
<223> OTHER INFORMATION: Synthetic Oligonucleotide

```
<220> FEATURE:
<221> NAME/KEY: misc_feature
<222> LOCATION: (1)..(5)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(12)
<223> OTHER INFORMATION: wherein all the internucleotide linkages are
      phosphorothioate linkages with Sp Chirality

<400> SEQUENCE: 73
tcgacgtttt gacgttttga cggg                                          24

<210> SEQ ID NO 74
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(12)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(20)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 74
tcgacgtttt gacgttttga cggg                                          24

<210> SEQ ID NO 75
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (14)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (18)..(20)
<223> OTHER INFORMATION: wherein all the internucleotide linkages are
      phosphorothioate linkages with Sp Chirality

<400> SEQUENCE: 75
tcgacgtaga cgtagacggg                                               20
```

```
<210> SEQ ID NO 76
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 76
tagacgattc gtcgtctaga cggg                                          24

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (18)..(20)
<223> OTHER INFORMATION: wherein all the internucleotide linkages are
      phosphorothioate linkages with Sp Chirality

<400> SEQUENCE: 77
tagacgacgt cgtagacggg                                               20

<210> SEQ ID NO 78
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (9)..(12)
```

```
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 78
tcgacgtttt gacgttttga cggg                                           24

<210> SEQ ID NO 79
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(13)
<223> OTHER INFORMATION: wherein all the internucleotide linkages are
      phosphorothioate linkages with Sp Chirality
<220> FEATURE:
<221> NAME/KEY: misc_feature
<222> LOCATION: (17)..(25)
<223> OTHER INFORMATION: wherein all the internucleotide linkages are
      phosphorothioate linkages with Sp Chirality

<400> SEQUENCE: 79
tcgacgtttt taacgacttg acggg                                          25

<210> SEQ ID NO 80
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (9)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 80
tcgacgtttt aacgacttga cggg                                           24

<210> SEQ ID NO 81
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
```

```
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (22)..(24)
<223> OTHER INFORMATION: wherein all the internucleotide linkages are
      phosphorothioate linkages with Sp Chirality

<400> SEQUENCE: 81
tcatcgattt atcgatttga cggg                                              24

<210> SEQ ID NO 82
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (23)..(27)
<223> OTHER INFORMATION: wherein all the internucleotide linkages are
      phosphorothioate linkages with Sp Chirality

<400> SEQUENCE: 82
tcatcgattt atcgatttat cgatggg                                           27

<210> SEQ ID NO 83
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (20)..(24)
<223> OTHER INFORMATION: wherein all the internucleotide linkages are
      phosphorothioate linkages with Sp Chirality
```

```
<400> SEQUENCE: 83
tcatcgattt atcgatttat cggg                                              24

<210> SEQ ID NO 84
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (24)..(27)
<223> OTHER INFORMATION: wherein all the internucleotide linkages are
      phosphorothioate linkages with Sp Chirality
<220> FEATURE:
<221> NAME/KEY: misc_feature
<222> LOCATION: (30)..(32)
<223> OTHER INFORMATION: wherein all the internucleotide linkages are
      phosphorothioate linkages with Sp Chirality

<400> SEQUENCE: 84
tcatcgattt atcgatttat cgatttatcg gg                                     32

<210> SEQ ID NO 85
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (24)..(32)
<223> OTHER INFORMATION: wherein all the internucleotide linkages are
      phosphorothioate linkages with Sp Chirality

<400> SEQUENCE: 85
tcatcgattt atcgatttat cgatttatcg gg                                     32

<210> SEQ ID NO 86
<211> LENGTH: 30
<212> TYPE: DNA
<213> ORGANISM: Artificial Sequence
<220> FEATURE:
```

```
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(19)
<223> OTHER INFORMATION: wherein all the internucleotide linkages are
      phosphorothioate linkages with Sp Chirality
<220> FEATURE:
<221> NAME/KEY: misc_feature
<222> LOCATION: (24)..(30)
<223> OTHER INFORMATION: wherein all the internucleotide linkages are
      phosphorothioate linkages with Sp Chirality

<400> SEQUENCE: 86
tcatcgattt atcgatttat cgatatcggg                                       30

<210> SEQ ID NO 87
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 87
ttatcgattt atcgatttga cggg                                             24

<210> SEQ ID NO 88
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (14)..(22)
<223> OTHER INFORMATION: wherein all the internucleotide linkages are
      phosphorothioate linkages with Sp Chirality

<400> SEQUENCE: 88
tcatcgatat cgatttgacg gg                                               22

<210> SEQ ID NO 89
<211> LENGTH: 24
<212> TYPE: DNA
```

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 89
tcatcgattt atcgatttat cggg                                          24

<210> SEQ ID NO 90
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 90
tcatcgattt atcgatttga cgat                                          24

<210> SEQ ID NO 91
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(15)
<223> OTHER INFORMATION: wherein all the internucleotide linkages are
      phosphorothioate linkages with Sp Chirality
<220> FEATURE:
<221> NAME/KEY: misc_feature
<222> LOCATION: (19)..(23)
<223> OTHER INFORMATION: wherein all the internucleotide linkages are
      phosphorothioate linkages with Sp Chirality

<400> SEQUENCE: 91
tcgacgttga cgttgacgtt ggg                                           23

<210> SEQ ID NO 92
```

```
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(10)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(20)
<223> OTHER INFORMATION: wherein all the internucleotide linkages are
      phosphorothioate linkages with Sp Chirality

<400> SEQUENCE: 92
tcgacgttga cgttgacggg                                                   20

<210> SEQ ID NO 93
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(12)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 93
tcatcgattt atcgatttga cggg                                              24

<210> SEQ ID NO 94
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(10)
<223> OTHER INFORMATION: wherein all the internucleotide linkages are
      phosphorothioate linkages with Sp Chirality
<220> FEATURE:
<221> NAME/KEY: misc_feature
<222> LOCATION: (14)..(16)
<223> OTHER INFORMATION: wherein all the internucleotide linkages are
      phosphorothioate linkages with Sp Chirality
<220> FEATURE:
<221> NAME/KEY: misc_feature
<222> LOCATION: (19)..(24)
<223> OTHER INFORMATION: wherein all the internucleotide linkages are
      phosphorothioate linkages with Sp Chirality
```

<400> SEQUENCE: 94
tcatcgatat cgatgacgtt tggg                                             24

<210> SEQ ID NO 95
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(22)
<223> OTHER INFORMATION: wherein all the internucleotide linkages are
      phosphorothioate linkages with Sp Chirality

<400> SEQUENCE: 95
tcgacgtttg acgtttgacg gg                                               22

<210> SEQ ID NO 96
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 96
tcatcgattt atcgatttat cggg                                             24

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 97
gggacgatat cgtcggggggg                                                 20

<210> SEQ ID NO 98
<211> LENGTH: 20

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(10)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 98
gggacgacgt cgtcgggggg                                              20

<210> SEQ ID NO 99
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(19)
<223> OTHER INFORMATION: wherein all the internucleotide linkages are
      phosphorothioate linkages with Sp Chirality

<400> SEQUENCE: 99
gggacgacgt cgtcggggg                                               19

<210> SEQ ID NO 100
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 100
tcgacgacgt cgtcgggggg                                              20

<210> SEQ ID NO 101
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
```

```
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 101
tcgacgacgt cgtctttggg                                                 20

<210> SEQ ID NO 102
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 102
tagacgacgt cgtctttggg                                                 20

<210> SEQ ID NO 103
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 103
ttgacgacgt cgtcaaaggg                                                 20

<210> SEQ ID NO 104
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 104
tcgacgtaga cgtctttggg                                                 20

<210> SEQ ID NO 105
```

```
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 105
tcgacgtaga cgtttagggg                                                   20

<210> SEQ ID NO 106
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 106
tcatcgatat cgattttggg                                                   20

<210> SEQ ID NO 107
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(20)
<223> OTHER INFORMATION: wherein all the internucleotide linkages are
      phosphorothioate linkages with Sp Chirality

<400> SEQUENCE: 107
ttatcgatat cgataaaggg                                                   20

<210> SEQ ID NO 108
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (17)..(21)
```

```
<223> OTHER INFORMATION: wherein all the internucleotide linkages are
      phosphorothioate linkages with Sp Chirality

<400> SEQUENCE: 108
tcgacgtaga cgatcgatgg g                                              21

<210> SEQ ID NO 109
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 109
tcgacgactt gacgacttga cggg                                           24

<210> SEQ ID NO 110
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 110
tcgacgactt gtcgtcttga cggg                                           24

<210> SEQ ID NO 111
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(23)
<223> OTHER INFORMATION: wherein all the internucleotide linkages are
      phosphorothioate linkages with Sp Chirality
```

```
<400> SEQUENCE: 111
ttatcgatat cgatatcgat ggg                                              23

<210> SEQ ID NO 112
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(22)
<223> OTHER INFORMATION: wherein all the internucleotide linkages are
      phosphorothioate linkages with Sp Chirality

<400> SEQUENCE: 112
ttatcgatat cgatttaaag gg                                               22

<210> SEQ ID NO 113
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(11)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 113
tcatcgattt atcgatttga cgtt                                             24

<210> SEQ ID NO 114
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (7)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(21)
<223> OTHER INFORMATION: wherein all the internucleotide linkages are
      phosphorothioate linkages with Sp Chirality

<400> SEQUENCE: 114
tcatcgatat cgatgacggg g                                                21
```

<210> SEQ ID NO 115
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(9)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(17)
<223> OTHER INFORMATION: wherein all the internucleotide linkages are
      phosphorothioate linkages with Sp Chirality

<400> SEQUENCE: 115
tcatcgatat cgatggg                                                 17

<210> SEQ ID NO 116
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (13)..(20)
<223> OTHER INFORMATION: wherein all the internucleotide linkages are
      phosphorothioate linkages with Sp Chirality

<400> SEQUENCE: 116
tcgtcgttgt cgttgacggg                                              20

<210> SEQ ID NO 117
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: wherein all the internucleotide linkages are
      phosphorothioate linkages with Sp Chirality
<220> FEATURE:
<221> NAME/KEY: misc_feature
<222> LOCATION: (8)..(12)
<223> OTHER INFORMATION: wherein all the internucleotide linkages are
      phosphorothioate linkages with Sp Chirality
<220> FEATURE:
<221> NAME/KEY: misc_feature
<222> LOCATION: (16)..(24)
<223> OTHER INFORMATION: wherein all the internucleotide linkages are
      phosphorothioate linkages with Sp Chirality

<400> SEQUENCE: 117
tcgtcgtttt gtcgttttga cggg                                         24

<210> SEQ ID NO 118

```
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(3)
<223> OTHER INFORMATION: wherein all the internucleotide linkages are
      phosphorothioate linkages with Sp Chirality
<220> FEATURE:
<221> NAME/KEY: misc_feature
<222> LOCATION: (15)..(23)
<223> OTHER INFORMATION: wherein all the internucleotide linkages are
      phosphorothioate linkages with Sp Chirality

<400> SEQUENCE: 118
tcgtcgttgt cgttgacgac ggg                                             23

<210> SEQ ID NO 119
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(24)
<223> OTHER INFORMATION: wherein all the internucleotide linkages are
      phosphorothioate linkages with Sp Chirality

<400> SEQUENCE: 119
tcgtcgtttt gtcgttttgt cgtt                                            24
```

CHIRAL NUCLEIC ACID ADJUVANT HAVING ANTITUMOR EFFECT AND ANTITUMOR AGENT

FIELD OF THE INVENTION

This invention is directed to a chiral nucleic acid adjuvant which has anti-tumor activity and an anti-tumor agent (a therapeutic agent or prophylactic agent for tumor). In more detail, this invention is directed to an adjuvant for anti-tumor agent comprising CpG oligonucleotides having PS and PO structures.

BACKGROUND OF THE INVENTION

JP 2002-513763 T (Patent Literature 1), JP 2002-154397 A (Patent Literature 2), JP 2002-521489 T (Patent Literature 3) disclose CpG oligonucleotide and the method of manufacturing them.

JP 2010-504750 T (Patent Literature 4) discloses that oligonucleotides, which have lipophilic substituted nucleotide analogues out of CpG motif, cause production of interferon-α (IFN-α).

Following Non Patent Literature 1 discloses that the S-form stereoisomer of CpG oligonucleotide trimer promotes MAPK signal.

Following Non Patent Literature 2 discloses PF-3512676 (Sequence No. 119), all parts of the sequence are phosphorothioated and S-form stereoisomer. Natural oligonucleic acid is readily reduced in vivo. Whereas, that are changed phosphodiester of oligo nucleic acid (P—O bond) to phosphoric acid thioester bond (P—S bond), P—S modifications are difficult to be reduced in vivo.

The following Non-Patent Literature 3 discloses that the CpG oligonucleotide (oligonucleotide having a CpG sequence) activates Th1 immune path through the Toll-like receptor (TLR9). CpG oligonucleotides can be classified into three types: class A-C. In CpG oligonucleotides classified as class A, the 3' and 5'-phosphate-binding site of the end of 1-4 bases are phosphorothioate linkages (PS-binding), shows a strong IFN-α production inducing ability. However, its effects on B cell proliferation is weak. On the other hand, CpG oligonucleotides are classified as class B and C, all the phosphate binding sites are of S, shows a strong B-cell proliferation effect. However, its IFN-α production inducing ability is not so strong. Natural oligonucleic acid consist of phosphodiester bonds (PO bond) is readily reduced in vivo.

The following non-patent literature 4 discloses the anti-tumor activity of A-class and B-class CpG oligonucleotide. Both Class CpG oligonucleotide showed anti-tumor activity when they were administered in combination with cancer antigens. However, there was no effect when administered oligonucleotides alone. In order to express the activity, they should be administered as liposome formulations to prevent degradation in vivo.

The following patent literature 5 discloses a pharmaceutical composition for the tumor treatment including an adjuvant. The following patent literature 6 discloses a anti-tumor agent which comprises an adjuvant consist of a CpG oligonucleotide and comprises an oligonucleotide as an effective ingredient.

CITATION LIST

Patent Literature

[Patent Literature 1] JP 2002-513763 A
[Patent Literature 2] JP 2002-154397 A
[Patent Literature 3] JP 2002-521489 A
[Patent Literature 4] JP 2010-504750 A
[Patent Literature 5] JP 3044009
[Patent Literature 6] JP 4977035

Non Patent Literature

[Non Patent Literature 1] Authur M. Krieg et al. OLIGO-NUCLROTIDES 13: pp. 491-499 (2003)
[Non Patent Literature 2] Clin Cancer Res. 2008 Jul. 15; 14(14):4532-42.
[Non Patent Literature 3] Krieg, Am., J Clin Invest (2007) 117:1184-1194.
[Non Patent Literature 4] Pedro Berraondo et al. Cancer Res 67: pp. 8847-8855(2007).

SUMMARY OF INVENTION

Technical Problem

For example, all of the sequence of the CpG oligonucleotide disclosed in Non Patent Literature 2 are phosphorothioated (PS bond). Therefore CpG oligonucleotides disclosed in Non Patent Literature 2 have problems that they induce inflammation and toxic reaction. When the phosphorothioate backbone modification is removed from the CpG oligonucleotides disclosed in Non Patent Literature 2, the stability of the nucleotide decreases. In addition, there is a problem that Natural CpG oligonucleotides also readily reduced in vivo.

In the anti-tumor agent disclosed in the Patent Literatures 5 and 6, the adjuvant having strong anti-tumor activity is used to enhance the curative effect for tumor. Further, it may be possible to improve tumor in patients unable to improve tumor by active ingredients such as a chemotherapeutic agent or the cancer antigen vaccine.

One object of the present invention is to provide an adjuvant comprising a stable CpG oligonucleotide having anti-tumor activity.

Other object of the present invention is to provide an anti-tumor agent comprising a stable CpG oligonucleotide. In particular, one object of the present invention is to provide an adjuvant for anti-tumor agent comprising a stable CpG oligonucleotide having anti-tumor activity.

Means for Achieving the Object

This invention is basically based on the following new finding. It is possible to enhance in-vivo stability of the oligo nucleic acid by controlling the molecular conformation of the oligo nucleic acid. Because of it, it becomes possible to provide a stable oligonucleotide in vivo, without introducing the PS bond to all of the sequences. Because not all of the sequences have PS binding modification, the oligonucleotide of the present invention has excellent biocompatibility. In addition, as shown in the working examples below, the oligonucleotide of the present invention also has anti-tumor activity.

The first aspect of the invention relates to an adjuvant for anti-tumor agent, wherein the adjuvant comprises oligonucleotides which comprise two to four CpG motif each represented by 5'-$X_1$CpG$X_2$-3' and has a length of 14 to 32 nucleotides, wherein the CpG is non-methylated CpG without modified phosphate backbones, wherein the $X_1$ is A or T, wherein the $X_2$ is A or T, wherein a nucleic acid at 3' end side of at least two CpG motifs is connected by phosphorothioate linkage, wherein each nucleic acid at 3' end and 5' end of the oligonucleotide is S type nucleic acid connected by phosphorothioate linkage, and wherein the oligonucleotide comprises at least one nucleic acid without phosphorothioate modification. It is preferred that nucleic acids without modified phosphate backbones is present on the part besides CpG motifs.

The adjuvant for anti-tumor agent is an adjuvant used in an anti-tumor agent.

In preferred examples of the adjuvant of the present invention, X1 is A, X2 is T. Then, the nucleic acid with phosphorothioate bond is a first S-form T having phosphorothioate bond. That is, in the adjuvant of the present invention, a nucleic acid at 3' end side of at least two CpG motifs is connected by phosphorothioate linkage. In the preferred example, $T^{SP}$ ($T^{SP}$ represents T with phosphorothioate bond) is present adjacent to the 5'-ACpGT-3.

More preferred example of the adjuvants of the present invention is an adjuvant that has a further second S-form T adjacent to the first S-form T (5'-ACpGTT$^{SP}$T$^{SP}$-3). Furthermore, an adjuvant that has a third S-form T adjacent to the second S-form T (5'-ACpGTT$^{SP}$T$^{SP}$T$^{SP}$-3) is also preferred.

In the adjuvant of the present invention, it is preferred that the nucleic acid base of 5' terminal is the S-form nucleic acid base with phosphorothioate bond. Furthermore, in the adjuvant of the present invention, it is preferred that the nucleic acid base of 3' terminal is the S-form nucleic acid base with phosphorothioate bond.

The preferred examples of the adjuvant of the present invention are adjuvants comprising an oligonucleotide having the nucleotide sequence represented by SEQ ID NO: 4, 6, 26, 33, 42, 43, 49-51, 56-58, 60-63, 74, 78-80, 82, 83, 85-96, 98, 99, 101-106, 108, 109 or 111-118.

The oligonucleotide of this invention is preferred to include any of the following sequences or be an oligonucleotide consisting of any of the following sequences.

TABLE 1-1

| Seq. No. | Sequence (5'→3') |
| --- | --- |
| 4 | T*C*AACGTT*T*C*AACGTT*T*T*G*G |
| 6 | T*C*AACGTT*T*C*AACGTT*G*G*G*G |
| 26 | T*C*GACGTT*T*T*GACGTT*T*T*GACGTT*T*T*G*A*C*G*G*G |
| 33 | T*C*GACGTT*T*T*GACGTT*T*T*GACGG*G*G*G*G |
| 42 | G*G*GACGATATCGTCG*G*G*G*G*G |
| 43 | G*G*GACGACGTCGTCG*G*G*G*G*G |
| 49 | T*C*ATCGAT*T*T*ATCGAT*T*T*A*A*C*G*G*G |
| 50 | T*C*GACGTTTTGACGTT*T*T*G*A*C*G*G*G |
| 51 | T*C*GACGTTTTGACGTTTGACGGG |
| 56 | T*C*GACGT*T*GACGT*T*G*A*C*G*G*G |
| 57 | T*C*ATCGATATCGA*T*G*A*C*G*G*G |
| 58 | T*C*GACGTTGACGT*T*G*A*C*G*G*G |
| 60 | T*C*GACGTT*T*T*GACGT*T*T*T*G*G*G*G*G |
| 61 | T*C*GACGTT*T*T*GAGGT*T*T*T*G*A*G*G*G*G |
| 62 | T*C*GACGTT*T*T*GACGT*T*T*T*G*T*G*G*G*G |
| 63 | T*C*G*ACGTTGACGTTGACGGG |

TABLE 1-1-continued

| Seq. No. | Sequence (5'→3') |
| --- | --- |
| 78 | T*C*G*ACGTTT*T*G*ACGTT*T*T*G*A*C*G*G*G |
| 79 | T*C*G*ACGTT*T*T*T*A*ACGAC*T*T*G*A*C*G*G*G |
| 80 | T*C*G*ACGTTT*T*AACGAC*T*T*G*A*C*G*G*G |
| 82 | T*C*ATCGAT*T*T*ATCGAT*T*T*ATCGA*T*G*G*G |
| 83 | T*C*ATCGAT*T*T*ATCGAT*T*T*AT*C*G*G*G |
| 85 | T*C*ATCGAT*T*T*ATCGAT*T*T*ATCGAT*T*T*A*T*C*G*G*G |

TABLE 1-2

| Seq. No. | Sequence (5'→3') |
| --- | --- |
| 86 | T*C*ATCGAT*T*T*ATCGAT*T*T*ATCGAT*A*T*C*G*G*G |
| 87 | T*T*ATCGAT*T*T*ATCGAT*T*T*G*A*C*G*G*G |
| 88 | T*C*ATCGATATCGAT*T*T*G*A*C*G*G*G |
| 89 | TCATCGAT*T*T*ATCGAT*T*T*A*T*C*G*G*G |
| 90 | T*C*ATCGAT*T*T*ATCGAT*T*T*G*A*C*G*A*T |
| 91 | T*C*GACGTTGACGTTGACGTTGGG |
| 92 | T*C*G*ACGTTGACGTTGACGGG |
| 93 | T*C*A*TCGAT*T*T*A*TCGAT*T*T*G*A*C*G*G*G |
| 94 | T*C*A*TCGAT*A*TCGAT*G*ACGT*T*T*G*G*G |
| 95 | T*C*GACGTTTGACGTTT*G*A*C*G*G*G |
| 96 | T*C*ATCGAT*T*T*ATCGAT*T*T*A*T*C*G*G*G |
| 98 | G*G*GACGAC*G*TCGTCG*G*G*G*G*G |
| 99 | G*G*GACGACGTCGTCG*G*G*G*G |
| 101 | T*C*GACGACGTCGTCT*T*T*G*G*G |
| 102 | T*A*GACGACGTCGTCT*T*T*G*G*G |
| 103 | T*T*GACGACGTCGTCA*A*A*G*G*G |
| 104 | T*C*GACGTAGACGTCT*T*T*G*G*G |
| 105 | T*C*GACGTAGACGTTT*A*G*G*G*G |
| 106 | T*C*ATCGATATCGATT*T*T*G*G*G |
| 108 | T*C*GACGTAGACGATCGATGGG |
| 109 | T*C*GACGAC*T*T*GACGAC*T*T*G*A*C*G*G*G |
| 111 | T*T*ATCGATATCGATA*T*C*G*A*T*G*G*G |
| 112 | T*T*ATCGATATCGATT*T*A*A*A*G*G*G |
| 113 | T*C*ATCGATTTATCGATTTGACGTT |
| 114 | T*C*ATCGA*T*ATCGA*T*G*A*C*G*G*G*G |
| 115 | T*C*ATCGATATCGATGGG |
| 116 | T*C*GTCGTTGTCGT*T*G*A*C*G*G*G |
| 117 | T*C*G*TCGTT*T*T*G*TCGTT*T*T*G*A*C*G*G*G |
| 118 | T*C*GTCGTTGTCGTTG*A*C*G*A*C*G*G*G |

In above formula * indicates the stereoisomer caused by phosphate backbone modification by sulfur atoms. In each sequence above, at least one of the * is S-form stereoisomer.

The preferred examples of adjuvant of the present invention are the oligonucleotides that have immunity-inducing activity and comprise oligonucleotides that represented by SEQ ID NO: 56, 57, 82, 103 or 109, or that one or two bases are substituted from, inserted to, deleted from or added to oligonucleotides having the nucleotide sequence represented by SEQ ID NO: 56, 57, 82, 103 or 109.

The second aspect of the invention relates to an anti-tumor agent which comprises the adjuvant described above. This anti-tumor agent may comprise any oligonucleotides described above as an active ingredient. This anti-tumor agent may comprise the adjuvant of the present invention with known active ingredient. In this case, This adjuvant sometimes shows the synergistic effect with the active ingredient because the oligonucleotide of the present invention has anti-tumor activity. Further, it may be possible to enhance the immunity-induction in patients unable to enhance the immunity-induction by the active ingredient. t Effect of the Invention According to the present invention, it is possible to provide an adjuvant comprising a stable CpG oligonucleotide having anti-tumor activity.

According to the present invention, it is possible to provide an adjuvant for anti-tumor agent comprising a stable CpG oligonucleotide having anti-tumor activity.

BEST MODE FOR CARRYING OUT THE INVENTION

Figure 1:
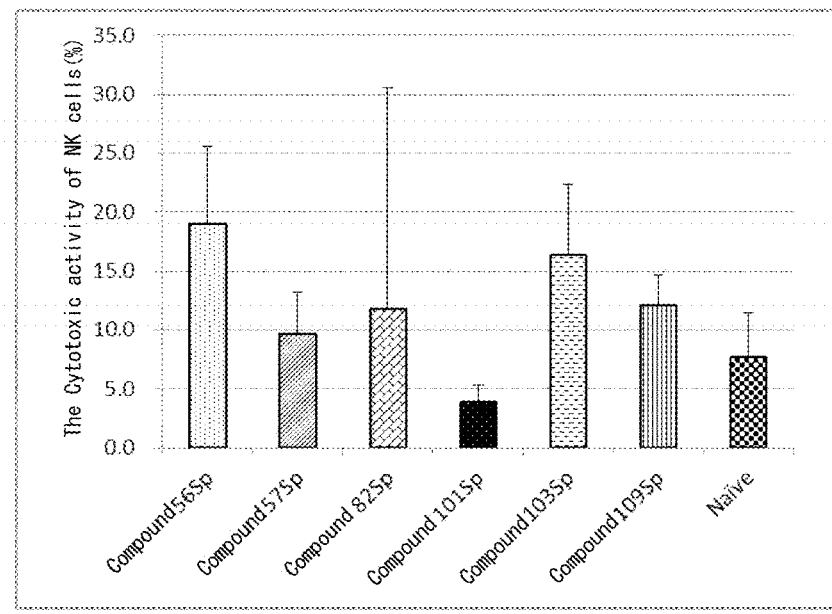
FIG. 1 is a diagram showing the activity of NK cells.

The following describes embodiments of the present invention. The present invention is not limited to the embodiments described below and includes those that a skilled person in the art will easily modify based on the following embodiments.

"Oligonucleotide" or "oligo" means sugar (e.g. ribose or deoxyribose) binding multiple nucleotides (i.e. Phosphate groups and substituted organic bases (either of substituted pyrimidines (e.g. cytosine (C), thymine (T) or uracil (U)) or substituted purine (e.g. adenine (A) or guanine (G))). As used in this specification, the term "oligonucleotide" means both of oligoribonucleotide (ORN) and oligodeoxyribonucleotide (ODN). The term "oligonucleotide" includes also oligonucleoside (i.e., the oligonucleotide without phosphate) and any other organic base polymer. Oligonucleotides can be obtained from existing nucleic acid sources (e.g. genome or cDNA), but synthetic one (e.g. produced by oligonucleotide synthesis) is preferred.

CpG represents unmethylated CpG without phosphate backbone modification. C is 2'-deoxycytidine. G is 2'-deoxyguanosine. p is a bond between nucleoside with phosphodiester.

The oligonucleotide may have phosphate backbone modification on the part besides the CpG motif consisting of 5'-$X_1$CpG $X_2$-3'. On the other hand, there is the problem previously said on phosphate backbone with phosphorothioate backbone modification between all of nucleotides, it may be preferable that oxygen atoms are replaced by sulfur atoms by more than 20% less than 95%, it may be more than 30% less than 95%, more than 20% less than 90%, more than 40% less than 95%, more than 40% less than 90%, more than 40% less than 80%, more than 50% less than 95%, more than 50% less than 90%, more than 20% less than 80%.

The oligonucleotide of the present invention is preferred to have the following, or comprising any sequence, it is preferable that an oligonucleotide has any of the following sequences.

TABLE 2-1

| Seq. No. | Sequence (5'→3') |
|---|---|
| 4 | T*C*AACGTT*T*C*AACGTT*T*T*G*G |
| 6 | T*C*AACGTT*T*C*AAGGTT*G*G*G*G |
| 26 | T*C*GACGTT*T*T*GACGTT*T*T*GACGTT*T*T*G*A*C*G*G*G |
| 33 | T*C*GACGTT*T*T*GACGTT*T*T*GACGG*G*G*G*G |
| 42 | G*G*GACGATATCGTCG*G*G*G*G*G |
| 43 | G*G*GACGACGTCGTCG*G*G*G*G*G |
| 49 | T*C*ATCGAT*T*T*ATCGAT*T*T*A*A*C*G*G*G |
| 50 | T*C*GACGTTTTGACGTT*T*T*G*A*C*G*G*G |
| 51 | T*C*GACGTTTTGACGTTTTGACGGG |
| 56 | T*C*GACGT*T*GACGT*T*G*A*C*G*G*G |
| 57 | T*C*ATCGATATCGA*T*G*A*C*G*G*G |
| 58 | T*C*GACGTTGACGT*T*G*A*C*G*G*G |
| 60 | T*C*GACGTT*T*T*GACGT*T*T*T*G*G*G*G*G |
| 61 | T*C*GACGTT*T*T*GACGT*T*T*T*G*A*G*G*G*G |
| 62 | T*C*GACGTT*T*T*GACGT*T*T*T*G*T*G*G*G*G |
| 63 | T*C*G*ACGTTGACGTTGACGGG |
| 78 | T*C*G*ACGTTT*T*G*ACGTT*T*T*G*A*C*G*G*G |
| 79 | T*C*G*ACGTT*T*T*T*A*ACGAC*T*T*G*A*C*G*G*G |
| 80 | T*C*G*ACGTTT*T*AACGAC*T*T*G*A*C*G*G*G |
| 82 | T*C*ATCGAT*T*T*ATCGAT*T*T*ATCGA*T*G*G*G |
| 83 | T*C*ATCGAT*T*T*ATCGAT*T*T*AT*C*G*G*G |
| 85 | T*C*ATCGAT*T*T*ATCGAT*T*T*ATCGAT*T*T*A*T*C*G*G*G |

TABLE 2-2

| 86 | T*C*ATCGAT*T*T*ATCGAT*T*T*ATCGAT*A*T*C*G*G*G |
| 87 | T*T*ATCGAT*T*T*ATCGAT*T*T*G*A*C*G*G*G |
| 88 | T*C*ATCGATATCGAT*T*T*G*A*C*G*G*G |

TABLE 2-2-continued

| | |
|---|---|
| 89 | TCATCGAT*T*T*ATCGAT*T*T*A*T*C*G*G*G |
| 90 | T*C*ATCGAT*T*T*ATCGAT*T*T*G*A*C*G*A*T |
| 91 | T*C*GACGTTGACGTTGACGTTGGG |
| 92 | T*C*G*ACGTTGACGTTGACGGG |
| 93 | T*C*A*TCGAT*T*T*A*TCGAT*T*T*G*A*C*G*G*G |
| 94 | T*C*A*TCGAT*A*TCGAT*G*ACGT*T*T*G*G*G |
| 95 | T*C*GACGTTTGACGTTT*G*A*C*G*G*G |
| 96 | T*C*ATCGAT*T*T*ATCGAT*T*T*A*T*C*G*G*G |
| 98 | G*G*GACGAC*G*TCGTCG*G*G*G*G*G |
| 99 | G*G*GACGACGTCGTCG*G*G*G*G |
| 101 | T*C*GACGACGTCGTCT*T*T*G*G*G |
| 102 | T*A*GACGACGTCGTCT*T*T*G*G*G |
| 103 | T*T*GACGACGTCGTCA*A*A*G*G*G |
| 104 | T*C*GACGTAGACGTCT*T*T*G*G*G |
| 105 | T*C*GACGTAGACGTTT*A*G*G*G*G |
| 106 | T*C*ATCGATATCGATT*T*T*G*G*G |
| 108 | T*C*GACGTAGACGATCGATGGG |
| 109 | T*C*GACGAC*T*T*GACGAC*T*T*G*A*C*G*G*G |
| 111 | T*T*ATCGATATCGATA*T*C*G*A*T*G*G*G |
| 112 | T*T*ATCGATATCGATT*T*A*A*A*G*G*G |
| 113 | T*C*ATCGATTTATCGATTTGACGTT |
| 114 | T*C*ATCGA*T*ATCGA*T*G*A*C*G*G*G*G |
| 115 | T*C*ATCGATATCGATGGG |
| 116 | T*C*GTCGTTGTCGT*T*G*A*C*G*G*G |
| 117 | T*C*G*TCGTT*T*T*G*TCGTT*T*T*G*A*C*G*G*G |
| 118 | T*C*GTCGTTGTCGTTG*A*C*G*A*C*G*G*G |

In above formula * indicates the stereoisomer by phosphate backbone modification. CG of the section corresponding to 5'-$X_1$CpG $X_2$-3 in above formula means unmethylated CpG without phosphate backbone modifications. The examples of phosphate backbone modifications are phosphorothioate backbone modifications, phosphorodithioate backbone modifications, or phosphoroamidate backbone modifications. In these phosphate backbone modifications, phosphorothioate backbone modifications are preferred. phosphorothioate backbone modifications means that converting one of the two nonbridging oxygen atoms bonding to phosphorus atoms comprising phosphodiester bond of neighbor nucleotides into sulfur atoms. At least one of the * is S-form stereoisomer. Here, S-form stereoisomer means, as described above, stereoisomer that takes S-form when their atoms or bases introduced instead of oxygen atoms are sulfur atoms.

The oligonucleotide of the present invention is preferred that it is one of the nucleotides described above, and phosphate backbone modifications which exist in at least one of the sites other than CpG motif are oligonucleotides including phosphorothioate. That is, as explained above, it is preferred that the oligonucleotide has phosphorothioate backbone modification also in the sites other than CpG. In this case, as explained above, S-form stereoisomer is preferred. However, in the present invention, the oligonucleotides with at least one unmodified phosphorothioate backbone is preferred than the oligonucleotides that all parts of the sequence are phosphorothioated.

Synthetic Method of Nucleotides

The synthetic method for nucleotides is publicly known. The nucleotides in present invention can be produced by the publicly known method. For example, it can adopt that the methods disclosed in JP patent No. 450870 and WO 2010/064146 pamphlet.

The other examples of the method for synthesizing nucleotide are introduced in U.S. Pat. No. 4,942,646 official report and U.S. Pat. No. 5,912,332. The latter, the use of the solid support attachment linker to parallel synthesis or generic solid support, such as phosphate salt attaching controlled pore glass.

Furthermore, nucleotide can be produced by the method e.g. disclosed in U.S. Pat. No. 4,383,534 A. For example, It can be produced by β-cyanoethyl phosphoroamidate method (S. L. Beaucage, M. H. Caruthers, Tetrahedron Lett. 1981, 22, 1859-62) and nucleoside H-phosphonate method (Per J. Garegg et al., Tetrahedron Lett. 1986, 27, 4051-4; Brian C. Froehler et al., Nucl Acid Res 1986, 14, 5399-407; Per J. Garegg et al., Tetrahedron Lett. 1988, 27, 4055-8; Barbara L. Gaffney et al., Tetrahedron Lett., 29, 2619-22). These chemicals can be synthesized by a variety of automated nucleic acid synthesizers available in the market. These nucleic acids are called synthetic nucleic acid. Alternatively, it is possible to generate nucleic acids of the present invention on a large scale in a plasmid. (Sambrook T. et al., Molecular Cloning: A Laboratory Manual, Cold Spring Harbor Laboratory Press, New York, 1989) The nucleic acid of this invention can be separated into smaller pieces or administered whole. The nucleic acid is produced from nucleic acid sequence (e.g. genomic sequence and cDNA sequence) with the use of known techniques (e.g. techniques using restriction enzymes, exonuclease or endonuclease) The nucleic acid that has been prepared in this way is called isolated nucleic acid. An isolated nucleic acid, in general, is a nucleic acid which is separated from components which naturally are normally associated. For example, the isolated nucleic acid is a nucleic acid that is separated from the cells, nucleus, mitochondria and chromatin. The combination motif nucleic acid of the present invention includes both synthesized combination motif nucleic acids and isolated combination motif nucleic acids.

The combination motif oligonucleotides, if necessary, have a relatively resistant to degradation (e.g., are stabilized) are preferred in the use of in vivo. A "stabilized nucleic acid molecule" means a nucleic acid molecule that is relatively resistant for in vivo degradation (e.g., exonuclease or endonuclease). The nucleic acid stabilization is achieved through the phosphate backbone modification. The stabilized nucleic acid that is preferred in the present invention has a modified backbone. This modification of the nucleic acid backbone provides increasing the activity of the combination motif oligonucleotide when administered in vivo. In some cases, the combination motif oligonucleotides with phosphorothioate bond provide maximum activity and protect the nucleic acid from degradation by intracellular exonucleases and cellular endonucleases. Other modified nucleic acids, modified phosphodiester nucleic acids, combinations of phosphodiester nucleic acids and phosphorothioate nucleic acids (i.e. chimeric), methylphosphonate, methylphosphorothioate, phosphorodithioate, p-ethoxy, and combinations thereof mentioned are.

The modified backbones (e.g., phosphorothioates) can be synthesized by using automated techniques employing either phosphoramidate chemistry or H-phosphonate chemistry. Aryl-phosphonate and alkyl-phosphonates can be generated, for example, as described in U.S. Pat. No. 4,469,863. And alkylphosphotriester (charged oxygen is alkylated as described in U.S. Pat. No. 5,023,243 and EP patent No. 092,574) can be produced using commercially available reagents by automated solid-phase synthesis. Methods for making modifications and substitutions of other DNA backbone have been disclosed. (e.g., Uhlmann E and Peyman A, Chem. Rev. 1990, 90, 544; Goodchild J., Bioconjugate Chem. 1990, 1, 165).

The oligonucleotides obtained by synthesis may be purified by known methods, e.g., purified, deprotected, desalted and dialyzed by reversed phase HPLC. In this way, the oligonucleotides of the present invention can be isolated and purified.

This invention provides composition with one of the above oligonucleotides. This composition is a medicine composition. The composition contains an effective amount of any of the oligonucleotides described above and it may contain appropriate known carrier. The carrier may be a solvent such as water or alcohol. The carrier can be optional excipients, diluents, fillers, salts, buffers, stabilizers, solubilizers, lipids or other substance which is well known for medicine compositions in the art.

The adjuvant for an anti-tumor agent is an adjuvant used in an anti-tumor agent. The anti-tumor agent is called as immunity-inducing agent or immune activation agent. The anti-tumor agent means an agent for inducing immune cells which secrete cytokines and the like in response to a certain antigen. The term "anti-tumor activity" means the ability to induce immune cells that secrete cytokines such as interferon in vivo. The examples of anti-tumor agent are agents for activating the induction of immunity against various cancers. The present invention also provides a cancer therapeutic agent or a cancer prophylactic agent. The anti-tumor agent may comprise components having immunity-inducing activity effects as an active ingredient in addition to the adjuvant that described above. Furthermore, the anti-tumor agent may comprise oligonucleotides in the adjuvant described above as an active ingredient.

For example, by using a known ELISPOT assay and the like, it is possible to confirm whether the oligonucleotides have anti-tumor activity.

Specifically, for example, the oligonucleotides to be assessed the anti-tumor activity was administrated to a living organism. Cells such as peripheral blood mononuclear cells was sampled from this organism. Then, the cells were co-cultured with the oligonucleotide. The amount of production of cytokinins in the cell is determined using specific antibodies. In this way, it is possible to measure the number of immune cells in the cells. Therefore, it is possible to assess the anti-tumor activity.

The tumor that is the target of anti-tumor agents include known tumors. The examples of the tumor are long bones of adamantinoma, adenoma, ameloblastoma, astrocytoma, cholangiocarcinoma, bladder cancer, bone cancer, bone marrow cancer, brain cancer, breast cancer, bronchogenic lung cancer, cervical cancer, cervical cancer, chondroma, choriocarcinoma, colon cancer, colorectal cancer, cystic adenocarcinoma, embryonal cancer, endometrial cancer, ependymoma, esophageal cancer, fibroma, follicular thymoma, gallbladder cancer, gastric cancer, glioblastoma, glioma, head and neck cancer, cancer of the heart, hepatocellular carcinoma, cancer in the peritoneal cavity, intestinal cancer, carcinoma of the kidney, larynx cancer, lipoma, liver cancer, lung cancer, cancer of the lymph nodes, cancer of the lymphatic vessels, malignant glioma, mesenthelioma, menigioma, medullary carcinoma, fibroids, neuroblastoma, non-small cell bronchogenic/lung, esophageal cancer, osteosarcoma, ovarian cancer, pancreatic cancer, papillary carcinoma, papillary adenocarcinoma, papillary thymoma, pheochromocytoma, prostate cancer, rectal cancer, kidney cancer, renal cell carcinoma, ureter cancer, abura-sengan, seminoma, skin cancer, small cell lung cancer, small intestine cancer, soft tissue cancer, spleen cancer, squamous cell carcinoma, gastric cancer, teratoma, testicular cancer, testicular cancer, thymoma, thyroid cancer, thyroid tumors and endometrial cancer.

This invention also provides a vaccine adjuvant with oligonucleotide described above. The vaccine adjuvant, if necessary, may contain a pharmaceutically acceptable carrier. JP Patent No. 4126252 discloses vaccine adjuvant with oligonucleotide. The vaccine adjuvant with the oligonucleotide of this invention can include the disclosed elements in this publication properly.

The oligonucleotide of this invention may be formulated as a pharmaceutical composition in a pharmaceutically acceptable carrier. This oligonucleotide may be administrated to a subject directly or with a nucleic acid delivery complex. The nucleic acid delivery complex means a nucleic acid which is associated (e.g., ionic bond or covalent bond, or encapsulated in the way) with a targeting way (e.g., molecules which generate high affinity bond to target cells (e.g., surface of B cell) and/or increase in cellular uptake by target cells.). The examples of the nucleic acid delivery complex are nucleic acid associated with sterols such as cholesterol, lipids (e.g., cationic lipids, virosomes or liposomes) or target cell specific bonding factors (egg, ligands recognized by target cell specific receptor). Preferred complex can be enough stable in vivo to prevent from significant de-coupling before the internalization by the target cell. But the complex can be cleavage under appropriate conditions in the cells so that the nucleic acid is released in a functional form.

This oligonucleotide and/or the antigen and/or other therapeutic agents can be administrated separately (e.g. in saline or buffer solution), and may also be administered using any known delivery vehicles.

Dose of the compounds described herein for mucosal delivery or topical delivery to the tumor is typically in the range of 0.1 µg/dose to 10 mg/dose. The doses depend on whether it is administered daily, weekly, or monthly, and in any other time. More typically, mucosal doses or local doses are in the range of 10 µg/dose to 5 mg/dose. The most typically, it is 100 µg/dose to 1 mg/dose, and the administrations of 2-4 times are performed apart for a few days or a few weeks. More typically, dose is in the range of 1 µg/dose to 10 mg/dose, most typically, in the range of 10 µg dose to 1 mg/dose. Then, the administrations are performed daily or weekly. The dose of the compounds described herein for parenteral delivery in order to induce an anti-tumor response, is typically 5 to 10,000-fold more than effective mucosal dose for vaccine adjuvant or immune stimulating applied. More typically, it is 10 to 1,000-fold greater, and most typically 20 to 100 times greater. In case of that the oligonucleotide is administered in combination with other therapeutic agents or administered using specialized delivery vehicles, the dose of the compounds described herein for parenteral delivery is typically in the range of about 0.1 μg/dose to 10 mg/dose. The doses depend on whether it is administered daily, weekly, or monthly, and in any other time. More typically parenteral doses for these purposes is in the range of about 10 μg/dose to 5 mg/dose. The most typically, it is about 100 μg/dose to 1 mg/dose, and the administrations of 2-4 times are performed apart for a few days or a few weeks. However, in some embodiments, parenteral doses for these purposes may be used in the 5 to 10,000-fold greater range than the typical doses described above.

In the present specification, the term "effective amount" means the required or sufficient amount to achieve the desired biological effect. For example, an effective amount of a chiral nucleic acid for treating an disease means the amount required to treat the disease. Combined with the teachings provided herein, by selecting the various active compounds and weighing factors (For example, potency, relative bioavailability, patient body weight, severity of adverse side-effects and preferred mode of administration), the effective prevention regimen and the effective therapeutic regimen, which are very effective to treat a particular subject without causing substantial toxicity, can be plan. The effective amount for any particular application may vary depending on factors, such as disease or condition being treated, the particular oligonucleotide being administered, antigen, subject size, and the severity of the disease and conditions. A skilled in the art can be empirically determined the effective amount of a particular oligonucleotide and/or antigen and/or other therapeutic agents without the need for undue experiments.

A therapeutically effective amount for any of the compounds described herein can first be determined based on the knowledge obtained in animal experiments. An effective dose for the treatment also can be determined based on the data about the CpG oligonucleotide which has been tested in human (human clinical trials has been started) and the data when the mucosal or local administration of known compounds having similar pharmacological activities [For example, other mucosal adjuvants (for example, LT and other antigens for vaccination)]. For parenteral administration, it is necessary to use higher dose. The applied dose can be adjusted based on the relative bioavailability and potency of the compounds administered. Adjusting the dose to achieve the maximal efficacy using the methods and other methods is well known in the art. In addition, a skilled person can easily adjust the dose.

When administered, formulation of the present invention is dissolved in a pharmaceutically demand solutions. The solution conventionally may include salts of pharmaceutically acceptable concentrations, buffering agents, preservatives, compatible carriers, adjuvants, and optionally other therapeutic ingredients.

For use in therapy, the oligonucleotide of the effective amount may be administered to a subject using any manner for delivering the nucleic acids to desired surface (for example, a tumor lesion, a mucosal surface and a systemically surface). Administering the pharmaceutical compositions of this invention may be accomplished by any means known to those skilled in the art. Preferred routes of administration are oral route, parenteral route, intramuscular route, subcutaneous route, intradermal route, intranasal route, the intratracheal route, inhalation routes, ocular route, sublingual, vaginal routes, rectal route, and the like, but not limited those listed herein.

For oral administration, the compounds (i.e., oligonucleotides, antigens, and other therapeutic agents) can be easily prepared by combining the active compound with known pharmaceutically acceptable carriers in the art. Such carriers enable the compounds of the present invention to be formulated as tablets to be taken orally by a subject to be targeted, pills, dragees, capsules, liquids, gels, syrups, slurries, suspensions and the like. The pharmaceutical preparations for oral administration may be obtained as solid excipient by adding suitable auxiliaries if necessary, subsequently grounding the resulting mixture and forming the tablet cores or the dragee cores by processing the mixture of granules. In particular, suitable excipients are fillers [for example, sugar (lactose, sucrose, mannitol and sorbitol); cellulose preparations (for example, corn starch, wheat starch, Rice starch, potato starch, gelatin, tragacanth gum, methyl cellulose, hydroxypropyl methyl-cellulose, sodium carboxymethyl-cellulose) and/or polyvinylpyrrolidone (PVP)]. If necessary, the disintegrating agents [for example, cross-linked polyvinyl pyrrolidone, agar, alginic acid or a salt thereof (for example, sodium alginate)] may be added. If necessary, the oral formulations may also be administered in saline or buffer solution to neutralize the acidic internal state. In addition, the oral formulations may be administered without any carriers.

The dragee cores are provided with suitable coatings. For this purpose, concentrated sugar solutions can be used. If necessary, the concentrated sugar solutions may contain gum arabic, talc, polyvinyl pyrrolidone, carbopol gel, polyethylene glycol and/or titanium dioxide, lacquer solutions, suitable organic solvents or solvent mixtures. In order to identify or characterize different combinations of active compound doses, dyestuffs or pigments may be added to the tablets or the dragee coatings.

Examples of pharmaceutical preparations which can be administered orally are a fabricated capsule of gelatin, and a soft sealed capsule made of gelatin and a plasticizer (for example, glycerol or sorbitol). The capsule may contain the active ingredient, if necessary, mixed with fillers (for example, lactose), binders (for example, starch) and/or lubricants (for example, talc or magnesium stearate) and stabilizers. In the soft capsule, the active compounds may be dissolved or suspended in suitable liquids (for example, fatty oils, liquid paraffin, or liquid polyethylene glycol). In addition, the stabilizer may be added. Microspheres formulated for oral administration may also be used. Such microspheres have been well known in the art. All formulations for oral administration may be used in appropriate dosage.

For oral administration, the compositions may take the form of tablets or lozenges formulated in conventional manner.

For inhalation administration, the compounds of the present invention may be administered by aerosol spray from pressurized packs or a nebulizer using a suitable propellant (for example, dichlorodifluoromethane, trichlorofluoromethane, dichlorotetrafluoroethane, carbon dioxide or other suitable gas) as with a conventional usage. When using a pressurized aerosol, the dosage unit can be determined by providing a valve to deliver a metered amount. For use in an inhaler or insufflator, such gelatin capsules and cartridges, which contain a powder mixture of the compound and a suitable powder base, may be provided.

If the compound should be delivered systemically, the compound can be provided in a form that can be administered parenterally by injection (for example, bolus injection or continuous infusion). The formulations for injection may be provided in unit dosage form (for example, an ampoule or multi-dose containers) with preservative agent. The compounds may take such forms as solutions, emulsions or suspension in oily or aqueous vehicles. In addition, they may contain the formulations (for example, suspending agents, stabilizing agents and/or dispersing agents).

Pharmaceutical formulations for parenteral administration include aqueous solutions of the active compounds which are water soluble. In addition, suspensions of the active compounds may be provided as appropriate oily injection suspensions. Suitable lipophilic solvents or vehicles include fatty oils (for example, sesame oil), synthetic fatty acid esters for example, ethyl oleate or triglycerides), or liposomes. Aqueous injection suspensions may contain substances which increase the viscosity of the suspension (for example, sodium carboxymethyl cellulose, sorbitol, or dextran). In order to prepare highly concentrated solutions, the suspension may also include agents that increase the solubility of the appropriate stabilizers or compounds thereof as necessary.

Alternatively, the active compounds may be in powder form which can be configured prior to use with a suitable vehicle (for example, sterile pyrogen-free water).

The compounds may be provided in the form for rectal or vaginal administration (for example, suppositories or retention enemas which may contain conventional suppository bases such as cocoa butter or other glycerides).

In addition to the above, the compounds may also be provided as a depot preparation. Such long acting formulations may be provided by using a suitable polymeric or hydrophobic materials (for example, as an emulsion in an acceptable oil), by using an ion exchange resin or by using poorly soluble derivatives (such as salts poorly soluble).

The pharmaceutical compositions may also include carriers or excipients which is a suitable solid or gel phase. Examples of such carriers or excipients include calcium carbonate, calcium phosphate, various sugars, starches, cellulose derivatives, gelatin, and polymers (for example, polyethylene glycol), but not limited thereto.

Suitable liquid pharmaceutical preparation form or solid pharmaceutical preparation forms are micro-encapsulated, chelated, coated on microscopic gold particles, included in liposomes, contained in the aerosol to be sprayed, included in the pellet for implantation into the skin, dried form in sharp on the object for scratching the skin, aqueous solution for inhalation or saline solution. In addition, the pharmaceutical compositions includes granules, powders, tablets, coated tablets, (micro) capsules, suppositories, syrups, emulsions, suspensions, creams, drops or preparations, which can release the active compound a long period of time. As described above, the formulations contain the excipients, the additives and/or the adjuvants (for example, disintegrants, binders, coating agents, sweetening agents, lubricants, flavoring agents, sweeteners, or solubilized agents) conventionally. The pharmaceutical compositions are suitable for use in a variety of drug delivery systems. Brief review of methods for drug delivery is mentioned in Langer (1990) Science 249: 1527-33 (which is incorporated herein by reference).

The oligonucleotide and that containing other therapeutic agent and/or antigen as necessary may be administered without being any processed, or may be administered in the form of a pharmaceutically acceptable salt. When administered in the form of a pharmaceutically acceptable salt, the salt should be pharmaceutically acceptable. However, the pharmaceutically acceptable salt may be used to prepare the pharmaceutically acceptable salts. Examples of such salts are the followings, but not limited thereto: HCl, hydrobromic acid, sulfuric acid, nitric acid, phosphoric acid, maleic acid, acetic acid, salicylic acid, p-toluene sulfonic acid, salt tartaric acid, citric acid, methane sulfonic acid, formic acid, malonic acid, succinic acid, naphthalene-2-sulfonic acid and benzene sulfonic acid. In addition, such salts may be prepared as alkali metal salts or alkaline earth metal salts (for example, sodium salts of carboxylic acid, potassium salt or calcium salt).

Examples of the suitable buffering agents are followings: acetic acid and its salt (1-2% w/v); citric acid and its salt (1-3% w/v); boric acid and its salt (0.5-2.5% w/v); and phosphoric acid and its salt (0.8-2% w/v). Examples of the suitable preservatives are followings: benzalkonium chloride (0.003-0.03% w/v); chlorobutanol (0.3-0.9% w/v); parabens (0.01-0.25% w/v), and thimerosal (0.004-0.02% w/v).

The pharmaceutical compositions of the present invention may contain an effective amount of the oligonucleotide, the antigen and/or other agents in a pharmaceutically acceptable carrier as necessary. The term "pharmaceutically acceptable carrier" means one or more compatible filler, diluent, or encapsulating agent which is solid or liquid and is suitable for administration to humans or other vertebrates. The term "carrier" means a natural or synthetic, organic or inorganic component which is added to in order to facilitate the application of the active ingredient. Components of the pharmaceutical compositions can be mixed with the compounds of this invention and each component in a manner that the components do not interact with each other.

For the treatment of individual subjects, different capacities of the pharmaceutical compositions of the present invention are required based on activity of the compound, manner of administration, purpose of the immunization (i.e., prophylactic immunization or immunotherapy), the nature and severity of the disorder, the age of the patient and weight of the patient. Administration of a desired dose may be performed by administering an amount corresponding to dosage units at a time or by administering a smaller amount multiple times.

Examples of other delivery systems include time-release system, delayed release system, or sustained release system. Such systems may avoid repeated administrations of the compound, and may increase the convenience to the subject and the physician. Many types of release delivery systems are available, and are known to those skilled in the art. Examples of the release delivery systems include a polymer-based system (for example, poly (lactide-glycolide), copoly oxalate, polycaprolactone, polyesteramides, polyorthoesters, polyhydroxybutyric acid, and polyanhydrides). For example, microcapsules of the polymer containing the pharmaceutical compositions are described in U.S. Pat. No. 5,075,109. The delivery systems also include non-polymeric system. Examples of the non-polymeric system are followings: lipids (sterols (for example, cholesterol, cholesterol ester), and fatty acids or natural fats (for example, monoglycerides, diglycerides, and triglycerides) and the like); hydrogel release systems; silastic system; peptide-based systems; wax coating; compressed tablets using conventional binders and excipients; partial fused to the implant. In particular, the system includes the followings, but not limited thereto: (a) an erosion-based system which the agent of the present invention is contained in a form located in the matrix (U.S. Pat. No. 4,452,775, U.S. Pat. No. 4,675,189 and U.S. Pat. No. 5,736,152); (b) a diffusion system which the active ingredient penetrate at a controlled rate from the polymer (U.S. Pat. No. 3,854,480, U.S. Pat. No. 5,133,974 and U.S. Pat. No. 5,407,686). In addition, pump-based hardware delivery systems can be used. Some of them are adapted for implantation.

The invention is further illustrated by the following examples. The following examples are should not be construed as further limiting. Throughout this specification, all of the contents of the cited documents are incorporated herein.

Working Example 1

Synthesis of Chiral CpG Oligonucleic Acid

CpG Oligonucleic Acid (Mixture)

The oligonucleic acid (mixture) which had been synthesized using phosphoramidite method and purified using HPLC were purchased from GeneDesign, Inc.

Synthesis of the CpG oligonucleotide of which the three-dimensional structure is modified.

Extension of nucleic acid chain was performed by repeating the following steps (i)-(iv).

(i) 3% DCA (dichloroacetic acid)/$CH_2Cl_2$ (15 sec), (ii) Condensation reaction [A mixture of 0.1 M monomer solution in MeCN (See below) and 1 M PhIMT (Trifluoromethanesulfonic acid N-phenylimidazolium) solution in MeCN in ratio 1:1, 5 min], (iii) Capping reaction [A mixture of 0.5 M $CF_3$Colm in THF and 1 M DMAN (1,8-bis(dimethylamino)naphthalene)) in THF in ratio 1:1, 30 sec], (iv) Sulfurization reaction (0.1 M DDTT in MeCN, 90 sec) or oxidization reaction (0.02 M $I_2$ in $H_2O$-Pyridine-THF solution, 15 sec).

After the chain elongation of nucleic acid, a solid phase carrier was collected in 1.5 ml microtube. The solid phase carrier was treated with high concentrated aqueous ammonia (1.2 ml, 55 degrees, 48 hours). The solid phase carrier was removed by filtration. A filtrate was dried in reduced pressure, and dissolved in water (1.0 ml). Then, the oligomer was isolated and purified by using a reversed-phase HPLC.

A procedure for adjusting 0.1 M monomer solution in MeCN (in case of Rp-Th).

Thymidylic acid H-phosphonate monoester (25 μmol) was azeotropic-dried with dehydrated pyridine and dehydrated toluene. it was dissolved in MeCN-CMP (N-Cyanomethylpiperidine) solution (9:1, v/v; 250 μL). Subsequently, $Ph_3PCl_2$ (62.5 μmol) was added, and the solution was stirred for 10 min. Then, AA-L (30 μmol; AA-D was used when Sp form was selected.) was added, and the solution was stirred for 10 min. In this way, the monomer solution was obtained.

In the description above, DDTT, AA-L and AA-D mean the abbreviated designation of the following compounds respectively. The obtained oligonucleic acids are shown in Table 1.

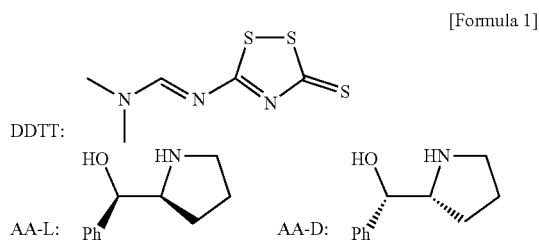

[Formula 1]

TABLE 3

| Seq. No. | Sequence |
|---|---|
| 1 | T*C*GTCGTT*T*T*GTCGTT*T*T*GTCGGG |
| 2 | G*G*GTCGTT*T*T*GTCGTT*T*T*GTCGGG |
| 3 | T*C*AACGTT*T*C*AACGTT*T*T |
| 4 | T*C*AACGTT*T*C*AACGTT*T*T*GG |
| 5 | T*C*AACGTT*T*C*AACGTT*G*G |
| 6 | T*C*AACGTT*T*C*AACGTT*G*G*G*G |
| 7 | T*C*AACGTT*T*T*AACGTT*T*T*AACGGG |
| 8 | T*C*AACGTT*T*A*ACGTT*T*T |
| 9 | T*C*AACGT*TAACGTT*T*T |
| 10 | T*C*AACGTT*T*A*AACGTT*T*A*AACGGG |
| 11 | T*C*AAGGTTAACCTTAACGGG |
| 12 | T*C*GACGTT*T*T*GACGTT*T*T*GACGGG |
| 13 | TsCsGACGTTsTsTsGACGTTsTsTsGACGGG |
| 14 | TrCrGACGTTrTrTrGACGTTrTrTrGACGGG |
| 15 | G*G*GACGT*T*T*TGACGT*T*T*TGACGGGGG |
| 16 | T*C*GACGT*T*T*TGACGT*T*T*TGACGT*T*T*TGACGGG |
| 17 | T*C*GACGT*T*GACGT*T*GACGGG |
| 18 | TsCsGACGTsTsGACGTsTsGACGGG |
| 19 | TrCrGACGTrTrGACGTrTrGACGGG |
| 20 | T*C*GACGT*T*GACGT*T*GACGT*T*GACGGG |
| 21 | T*C*GACGTT*T*A*AACGTT*T*A*AACGTT*T*A*AACGGG |
| 22 | T*C*GACGTT*T*A*AACGTT*T*A*GACGTT*T*A*AACGGG |
| 23 | T*C*GACGTTAACGTTAACGTTAACGGG |
| 24 | GGGACGTT*T*A*AACGTCTAGACGGG |
| 25 | T*C*GACGT*ACGT*ACGT*ACGGG |
| 26 | T*C*GACGTT*T*T*GACGTT*T*T*G*A*C*G*G*G |
| 27 | TsCsGACGTTsTsTsGACGTTsTsTsGsAsCsGsG |
| 28 | TrCrGACGTTrTrTrGACGTTrTrTrGrArCrGrGrG |
| 29 | T*C*GACGTT*T*T*GACGTT*T*T*GACGG*G*G |

TABLE 4

| 30 | T*C*GACGTT*T*T*GACGTT*T*T*GACGT*G*G |
| 31 | T*C*GACGTT*T*T*GACGTT*T*T*GACGTG*G*G |
| 32 | T*C*GACGTT*T*T*GACGTT*T*T*G*A*C*G*G*G |
| 33 | T*C*GACGTT*T*GACGTT*T*T*GACGG*G*G*G |
| 34 | TsCsGACGTTsTsTsGACGTTsTsTsGACGGsGsGsGsG |
| 35 | TrCrGACGTTrTrTrGACGTTrTrTTGACGGrGrGrGrG |
| 36 | T*C*GACGTT*T*T*GACGTT*T*T*GACG*G*G*G*G |

TABLE 4-continued

| | |
|---|---|
| 37 | T*C*GACGT*T*GACGT*T*GACGTG*G*G |
| 38 | G*G*T*G*C*ATCGAT*G*C*A*G*G*G*G*G*G |
| 39 | T*C*ATCGAT*T*T*ATCGAT*T*T*ATCGGG |
| 40 | G*G*T*G*C*GACGAT*G*C*A*G*G*G*G*G*G |
| 41 | G*G*G*G*GACGATCGTCGGG*G*G*G |
| 42 | G*G*GACGATATCGTCG*G*G*G*G |
| 43 | G*G*GACGACGTCGTCG*G*G*G*G |
| 44 | GsGsGACGAGGTCGTCGsGsGsGsGsG |
| 45 | GrGrGACGACGTCGTCGrGrGrGrGrG |
| 46 | G*G*GGGACGATCGTCG*G*G*G*G |
| 47 | G*G*GACGCGCGTCG*G*G*G*G*G |
| 48 | G*G*G*G*TCGTTCG*G*G*G |

TABLE 5-1

| Seq. No. | Sequence |
|---|---|
| 49 | T*C*ATCGAT*T*T*ATCGAT*T*T*A*A*C*G*G*G |
| 50 | T*C*GACGTTTTGACGTT*T*T*G*A*C*G*G*G |
| 51 | T*C*GACGTTTTGACGTTTT*G*A*C*G*G*G |
| 52 | T*C*GACGT*T*GACGT*T*GACGG*G |
| 53 | T*C*GACGT*T*GACGT*T*GACG*G*G |
| 54 | T*C*GACGT*T*GACGT*T*GACGG*G*G |
| 55 | T*C*GACGT*T*GACGT*T*GACT*G |
| 56 | T*C*GACGT*T*GACGT*T*G*A*C*G*G*G |
| 57 | T*C*GACGTTGACGT*T*G*A*C*G*G*G |
| 58 | T*C*ATCGATATCGA*T*G*A*C*G*G*G |
| 59 | T*C*GACGT*T*GACGT*T*GACG*G*G*G |
| 60 | T*C*GACGTT*T*T*GACGTT*T*T*G*G*G*G |
| 61 | T*C*GACGTT*T*T*GACGTT*T*T*G*A*G*G*G |
| 62 | T*C*GACGTT*T*T*GACGTT*T*T*G*T*G*G*G |
| 63 | T*C*G*ACGTT*G*ACGTT*G*A*C*G*G*G |
| 64 | C*C*GACGTT*T*T*GACGTT*T*T*GACG*G*G |
| 65 | T*C*GACGTT*T*A*GACGTT*T*A*GACG*G*G |
| 66 | T*C*GACGTT*T*T*GACGTT*T*T*GACG*A*A |
| 67 | T*C*GACGTT*T*T*GACGTT*T*T*GACG*T*T |
| 68 | T*C*AACGTT*T*T*AACGTT*T*T*GACG*G*G |
| 69 | T*C*GACGTT*T*T*GACGTT*T*T*GGG |
| 70 | T*C*GACGTT*T*T*GACGTT*T*T*GACGTTGG |
| 71 | T*C*GACGTT*GACGTT*G*G*G |
| 72 | T*C*GACGTT*T*T*G*ACGTT*T*T*G*ACG*G*G |

TABLE 5-1-continued

| Seq. No. | Sequence |
|---|---|
| 73 | T*C*G*A*CGTT*T*T*G*ACGTTTTGACGGG |
| 74 | T*C*G*ACGTT*T*T*G*ACGTT*T*T*G*ACG*G |
| 75 | T*C*GACGTA*GACGTA*GACG*G*G |
| 76 | T*A*GACGAT*T*C*GTCGTC*T*A*GACG*G |
| 77 | T*A*GACGA*C*GTCGT*A*GACG*G*G |
| 78 | T*C*G*ACGTTT*T*G*ACGTT*T*T*G*A*C*G*G*G |
| 79 | T*C*G*ACGTT*T*T*T*A*ACGAC*T*T*G*A*C*G*G*G |

TABLE 5-2

80 T*C*G*ACGTTT*T*AACGAC*T*T*G*A*C*G*G*G
81 T*C*ATCGAT*T*T*ATCGAT*T*T*GACG*G*G
82 T*C*ATCGAT*T*T*ATCGAT*T*T*ATCGA*T*G*G*G
83 T*C*ATCGAT*T*T*ATCGAT*T*T*AT*C*G*G*G
84 T*C*ATCGAT*T*T*ATCGAT*T*T*ATCGAT*T*T*ATCG*G*G
85 T*C*ATCGAT*T*T*ATCGAT*T*T*ATCGAT*T*T*A*T*C*G*G*G
86 T*C*ATCGAT*T*T*ATCGAT*T*T*ATCGA*T*C*G*G*G
87 T*T*ATCGAT*T*T*ATCGAT*T*T*G*A*C*G*G*G
88 T*C*ATCGATATCGAT*T*T*G*A*C*G*G*G
89 TCATCGAT*T*T*ATCGAT*T*T*A*T*C*G*G*G
90 T*C*ATCGAT*T*T*ATCGAT*T*T*G*A*C*G*A*T
91 T*C*GACGT*T*GACGT*T*GACGT*T*G*G*G
92 T*C*G*ACGT*T*G*ACGT*T*G*A*C*G*G*G
93 T*C*A*TCGAT*T*T*A*TCGAT*T*T*G*A*C*G*G*G
94 T*C*A*TCGAT*A*TCGAT*G*ACGT*T*T*G*G*G
95 T*C*GACGTTTGACGTTT*G*A*C*G*G*G
96 T*C*ATCGAT*T*T*ATCGAT*T*T*A*T*C*G*G*G
97 G*G*GACGATATCGTCG*G*G*G*G
98 G*G*GACGAC*G*TCGTCG*G*G*G*G
99 G*G*GACGACGTCGTCG*G*G*G*G
100 T*C*GACGACGTCGTCG*G*G*G*G*G

TABLE 5-3

101 T*C*GACGACGTCGTCT*T*T*G*G*G
102 T*A*GACGACGTCGTCT*T*T*G*G*G
103 T*T*GACGACGTCGTCA*A*A*G*G*G
104 T*C*GACGTAGACGTCT*T*T*G*G*G
105 T*C*GACGTAGACGTTT*A*G*G*G
106 T*C*ATCGATATCGATT*T*T*G*G*G

TABLE 5-3-continued

```
107 T*T*ATCGATATCGATA*A*A*G*G*G
108 T*C*GACGTAGACGATCGA*T*G*G*G
109 T*C*GACGAC*T*T*GACGAC*T*T*G*A*C*G*G*G
110 T*C*GACGAC*T*T*GTCGTC*T*T*G*A*C*G*G*G
111 T*T*ATCGATATCGATA*T*C*G*A*T*G*G*G
112 T*T*ATCGATATCGATT*T*A*A*A*G*G*G
113 T*C*ATCGAT*T*T*ATCGAT*T*T*G*A*C*G*T*T
114 T*C*ATCGA*T*ATCGA*T*G*A*C*G*G*G
115 T*C*ATCGAT*ATCGA*T*G*G*G
116 T*C*GTCGTTGTCGT*T*G*A*C*G*G*G
117 T*C*G*TCGTT*T*T*G*TCGTT*T*T*G*A*C*G*G*G
118 T*C*GTCGTTGTCGTTG*A*C*G*A*C*G*G*G
119 T*C*G*T*C*G*T*T*T*T*G*T*C*G*T*T*T*T*G*T*C*G*T*T
```

In above tables, oligonucleotides of SEQ ID NO: 119 is a known compound (Compound 119).

In above table 1, * indicates the position that the S-form phosphorothioate backbone modification were induced into the backbone. In above table, "s" indicates the S-form phosphorothioate modification. In above table, "r" indicates the R-form phosphorothioate modification.

Working Example 2

Induction of Production of IFN-α in Simian Peripheral Blood Mononuclear Cells (PBMC)

The blood derived from Macaca fascicularis which has tested negative for B virus, diluted to 3 times with Hanks' Balanced Salt Solution. Then, the sample was layered on Ficoll-Paque PLUS centrifugation medium and centrifuged (2,600 rpm, 30 min). A fraction containing the peripheral blood mononuclear cells (PBMC) was obtained. After the PBMC was washed with RPMI medium (1% penicillin and streptomycin), the PBMC was suspended in RPMI medium (10% FBS, 1% penicillin and streptomycin) at a cell density of $3 \times 10^6$ cells/ml. The cells were cultured with various oligonucleic acids (mixture containing oligo DNA and DOTAP in a ratio of 1:3.2) in 96-well round-bottom plate for 17-24 hours using 5% $CO_2$ incubator. After the cultivation, cell culture supernatant was obtained by centrifuging (500 rpm, 5 min) the culture medium. Then, the concentration of IFN-α in the cell culture supernatant was measured using ELISA kit (PBL Assay Science).

The result was shown in Table 2 and Table 3. Table 2 indicates the IFN-α production induced by the oligonucleotide of the present invention in simian peripheral blood mononuclear cells. This result was obtained from the experiments using the oligonucleic acids of SEQ ID No.: 1-48.

TABLE 6

Table 2
Inducing effect by the oligonucleotide
of the present invention in IFN-α production
in simian peripheral blood mononuclear
cells (PBMC)

| Seq. No. | IFN α (pg/mL) | |
|---|---|---|
|  | Average | ±SE |
| 4 | 2151 | 1259.46 |
| 6 | 1767 | 1176.08 |
| 26 | 2404 | 306.42 |
| 33 | 850 | 417.75 |
| 42 | 1214 | 532.80 |
| 43 | 3776 | 1429.12 |
| 47 | 297 | 132.99 |

Table 3 indicates the IFN-α production induced by the oligonucleotide of the present invention in simian peripheral blood mononuclear cells. This result was obtained from the experiments using the oligonucleic acids of SEQ ID No: 49-118. The results in Table 3 were shown using relative values with the value in the case of using the oligonucleotide having the sequence (tcgtcgttttgtcgttttgtcgtt) of SEQ ID No. 119 (conventional nucleotide: Compound 119).

TABLE 7-1

Table 3
Inducing effect by the oligonucleotide of the present invention in
IFN-α production in simian peripheral blood mononulearcells (PBMC)

| Seq. No. | Sequence (* indicates the position of S-form phosphorothinate backbone modification.) | Ratio | ±SE | Number of samples |
|---|---|---|---|---|
| 49 | T*C*ATCGAT*T*T*ATCGAT*T*T*A*A*C*G*G*G | 195 | 40 | 4 |
| 50 | T*C*GACGTTTTGACGTT*T*T*G*A*C*G*G*G | 241 | 32 | 4 |
| 51 | T*C*GACGTTTTGACGTTTT*G*A*C*G*G*G | 265 | 52 | 3 |
| 56 | T*C*GACGT*T*GACGT*T*G*A*C*G*G*G | 210 | 59 | 6 |
| 57 | T*C*GACGTTGACGT*T*G*A*C*G*G*G | 269 | 71 | 3 |
| 58 | T*C*ATCGATATCGA*T*G*A*C*G*G*G | 255 | 42 | 4 |
| 60 | T*C*GACGTT*T*T*GACGTT*T*T*G*G*G*G*G | 123 | 38 | 5 |
| 61 | T*C*GACGTT*T*T*GACGTT*T*T*G*A*G*G*G | 123 | 30 | 5 |
| 62 | T*C*GACGTT*T*T*GACGTT*T*T*G*T*G*G*G | 117 | 17 | 5 |
| 63 | T*C*G*ACGTT*G*ACGTT*G*A*C*G*G*G | 155 | 29 | 3 |

TABLE 7-1-continued

Table 3
Inducing effect by the oligonucleotide of the present invention in
IFN-α production in simian peripheral blood mononulearcells (PBMC)

| Seq. No. | Sequence (* indicates the position of S-form phosphorothinate backbone modification.) | Ratio | ±SE | Number of samples |
|---|---|---|---|---|
| 78 | T*C*G*ACGTTT*T*G*ACGTT*T*T*G*A*C*G*G | 98 | 6 | 3 |
| 79 | T*C*G*ACGTT*T*T*T*A*ACGAC*T*T*G*A*C*G*G | 142 | 26 | 3 |
| 80 | T*C*G*ACGTTT*T*AACGAC*T*T*G*A*C*G*G | 223 | 22 | 3 |
| 82 | T*C*ATCGAT*T*T*ATCGAT*T*T*ATCGA*T*G*G | 263 | 38 | 4 |
| 83 | T*C*ATCGAT*T*T*ATCGAT*T*T*AT*C*G*G | 308 | 53 | 4 |
| 85 | T*C*ATCGAT*T*T*ATCGAT*T*T*ATCGAT*T*T*A*T*C*G*G | 170 | 21 | 4 |
| 86 | T*C*ATCGAT*T*T*ATCGAT*T*T*ATCGAT*A*T*C*G*G | 170 | 25 | 4 |
| 87 | T*T*ATCGAT*T*T*ATCGAT*T*T*G*A*C*G*G | 208 | 86 | 3 |
| 88 | T*C*ATCGATATCGAT*T*T*G*A*C*G*G | 288 | 135 | 3 |
| 89 | TGATCGAT*T*T*ATCGAT*T*T*A*T*C*G*G | 279 | 45 | 3 |
| 90 | T*C*ATCGAT*T*T*ATCGAT*T*T*G*A*C*G*A*T | 374 | 205 | 3 |
| 91 | T*C*GACGT*T*GACGT*T*GACGT*T*G*G | 135 | 41 | 5 |
| 92 | T*C*G*ACGT*T*G*ACGT*T*G*A*C*G*G | 97 | 25 | 3 |
| 93 | T*C*A*TCGAT*T*T*A*TCGAT*T*T*G*A*C*G*G | 109 | 34 | 3 |
| 94 | T*C*A*TCGAT*A*TCGAT*G*ACGT*T*T*G*G | 103 | 7 | 2 |
| 95 | T*C*GACGTTTGACGTTT*G*A*C*G*G | 222 | 37 | 4 |
| 96 | T*C*ATCGAT*T*T*ATCGAT*T*T*A*T*C*G*G | 129 | 35 | 3 |
| 98 | G*G*GACGAC*G*TCGTCG*G*G*G*G | 138 | 107 | 3 |
| 99 | G*G*GACGACGTCGTCG*G*G*G*G | 230 | 87 | 4 |

TABLE 7-2

| | | | |
|---|---|---|---|
| 101 | T*C*GACGACGTCGTCT*T*T*G*G*G | 404 | 52 3 |
| 102 | T*A*GACGACGTCGTCT*T*T*G*G*G | 387 | 126 3 |
| 103 | T*T*GACGACGTCGTCA*A*A*G*G*G | 302 | 64 5 |
| 104 | T*C*GACGTAGACGTCT*T*T*G*G*G | 354 | 75 4 |
| 105 | T*C*GACGTAGACGTTT*A*G*G*G*G | 297 | 65 4 |
| 106 | T*C*ATCGATATCGATT*T*T*G*G*G | 224 | 26 4 |
| 108 | T*C*GACGTAGACGATCGA*T*G*G*G | 370 | 70 4 |
| 109 | T*C*GACGAC*T*T*GACGAC*T*T*G*A*C*G*G | 235 | 76 3 |
| 111 | T*T*ATCGATATCGATA*T*C*G*A*T*G*G | 200 | 8 4 |
| 112 | T*T*ATCGATATCGATT*T*A*A*A*G*G | 257 | 40 4 |
| 113 | T*C*ATCGAT*T*T*ATCGAT*T*T*G*A*C*G*T*T | 209 | 27 4 |
| 114 | T*C*ATCGA*T*ATCGA*T*G*A*C*G*G*G | 155 | 37 3 |
| 115 | T*C*ATCGAT*ATCGA*T*G*G*G | 95 | 12 2 |
| 116 | T*C*GTCGTTGTCGT*T*G*A*C*G*G | 235 | 23 4 |
| 117 | T*C*G*TCGTT*T*T*G*TCGTT*T*T*G*A*C*G*G*G | 177 | 61 4 |
| 118 | T*C*GTCGTTGTCGTTG*A*C*G*A*C*G*G*G | 88 | 14 4 |

Using the nucleotide having the sequence of SEQ ID No: 119 (conventional nucleotide: Compound 119), the concentration of IFN-α was measured in the same manner as in above example 2. The results are shown in Table 4.

TABLE 8

Table 4
Concentration of IFN-α

| IFN-α (ng/mL) | ±SE |
|---|---|
| 52.2 | 6.2 |

Working Example 3
Effect on the Mouse Spleen Cell Proliferation
Experimental Procedure
Isolation of Mouse Spleen Cells A spleen was obtained from 10-13-week-old BALB/cAnNCrlCrlj mouse (purchased from Charles River Japan, Inc.). Then, this spleen was used for isolation of spleen cells.

The spleen was ground using a needle in a sterile PBS. The cell suspension was passed through a cell strainer of 70 μm and the filtrate was centrifuged. In order to remove the red blood cells, a red blood cell lysis solution was added to the cells. The cells was washed with PBS. The resulting cells was used for the measurement as mouse spleen cells.

Measurements of the Spleen Cell Proliferation (BrdU Assay)

The mouse spleen cells were suspended in RPMI medium (10% FBS, 100 IU/ml penicillin and 100 μg/ml streptomycin) at a cell density of $1\times10^5$ cells/ml. The cells were seeded in 96-well flat-bottom plates at a concentration of 50 μl/well. Various compounds were diluted to 2-fold concentration of the final concentration using RPMI medium. These diluted compounds were added to the cells by this 50 μl/well. Then, the cells were cultured for 20-24 hours. After the cultivation, the spleen cell proliferation was measured usingCell Proliferation ELISA, BrdU (colorimetric) kit (Roche Diagnostics). The measurement was performed according to the manufacturer's instructions. The result were shown in FIG. 5.

TABLE 9-1

Table 5
The result of measurement
of cell prolification

| Seq. No. | BrdU |
|---|---|
| 4 | 13% |
| 6 | 18% |
| 26 | 106% |
| 33 | 11% |
| 42 | 17% |
| 43 | 27% |
| 47 | 159% |
| 49 | 12% |
| 50 | 26% |
| 51 | 27% |
| 56 | 14% |
| 57 | 17% |
| 58 | 7% |
| 60 | 90% |
| 61 | 108% |
| 62 | 130% |
| 63 | 53% |
| 78 | 272% |
| 79 | 250% |

TABLE 9-2

| | |
|---|---|
| 80 | 66% |
| 82 | 8% |
| 83 | 8% |
| 85 | 10% |
| 86 | 9% |
| 87 | 8% |
| 88 | 6% |
| 89 | 9% |
| 90 | 15% |
| 91 | 13% |
| 92 | 12% |
| 93 | 8% |
| 94 | 8% |
| 95 | 21% |
| 96 | 8% |
| 98 | 19% |
| 99 | 9% |
| 101 | 13% |
| 102 | 5% |
| 103 | 5% |
| 104 | 14% |
| 105 | 3% |

TABLE 9-2-continued

| | |
|---|---|
| 106 | 17% |
| 108 | 8% |
| 109 | 4% |
| 111 | 15% |
| 112 | 8% |
| 113 | 8% |
| 114 | 3% |
| 115 | 8% |
| 116 | 4% |
| 117 | 58% |
| 118 | 11% |

The results were shown using a relative value in case that the value of the reference compound (Compound 119) is evaluate as 100%. All compounds induced the proliferation of mouse spleen cells.

Working Example 4

Cytokine production profile in simian peripheral blood mononuclear cells (PBMC) The blood derived from Macaca fascicularis which has tested negative for B virus, diluted to 2 times with Hanks' Balanced Salt Solution. Then, the sample was layered on Ficoll-Paque PLUS centrifugation medium and centrifuged (2,600 rpm, 30 min). A fraction containing the peripheral blood mononuclear cells (PBMC) was obtained. After the PBMC was washed with RPMI medium (100 IU/ml penicillin and 100 μg/ml streptomycin), the PBMC was suspended in RPMI medium (10% FBS, 100 IU/ml penicillin and 100 μg/ml streptomycin) at a cell density of $3\times10^6$ cells/ml. The cells were cultured with various compounds (mixture containing CpG oligonucleotide and DOTAP in a ratio of 1:3.2) in 96-well round-bottom plate for 16-20 hours using 5% $CO_2$ incubator. After the cultivation, cell culture supernatant was obtained by centrifuging (500 rpm, 5 min) the culture medium. Then, in order to obtain the cytokine profile in the cell culture supernatant, 7 kinds of cytokine, i.e., IFN-γ, IL-4, IL-6, IL-10, IL-12/23 (p40), IL-8 and TNF-α were measured using Milliplex MAP Kit Non-Human Primate Cytokine Magnetic Beads Panel(Merck).

Result

The results of the cytokine measurements are shown using a relative value in case that the value of the reference compound (Compound 119) is evaluate as 100%. All compounds strongly induced the production of Th1 cytokine (IFN-γ) in simian peripheral blood mononuclear cells.

TABLE 10-1

Table 6
Cytokine profile when the oligonucleotide of the present invention was used.

| Seq. No. | IFN-γ | IL-12 (p40) | TNF-α | IL-6 | IL-4 | IL-8 | IL-10 |
|---|---|---|---|---|---|---|---|
| 4 | 120 | 72 | 45 | 56 | L | 245 | 22 |
| 6 | 15 | 47 | 22 | 33 | L | 55 | 20 |
| 26 | 102 | 52 | 49 | 58 | L | 191 | 51 |
| 33 | 54 | 58 | 32 | 40 | L | 97 | 38 |
| 42 | 40 | 54 | 31 | 42 | L | 87 | 45 |
| 43 | — | — | — | — | — | — | — |
| 47 | — | — | — | — | — | — | — |
| 49 | 63 | 65 | 62 | 65 | L | 201 | 52 |
| 50 | 3 | 109 | 113 | 74 | L | | 296 |
| 51 | 19 | 50 | 54 | 74 | L | 123 | 74 |
| 56 | 223 | 77 | 83 | 53 | L | 157 | 21 |
| 57 | 97 | 76 | 84 | 57 | L | 49 | 45 |
| 58 | 26 | 40 | 34 | 42 | L | 73 | 39 |
| 60 | 91 | 38 | 163 | 75 | L | 189 | 46 |

TABLE 10-1-continued

Table 6
Cytokine profile when the oligonucleotide of the present invention was used.

| Seq. No. | IFN-γ | IL-12 (p40) | TNF-α | IL-6 | IL-4 | IL-8 | IL-10 |
|---|---|---|---|---|---|---|---|
| 61 | 276 | 50 | 56 | 49 | L | 106 | 31 |
| 62 | 418 | 48 | 83 | 55 | L | 137 | 44 |
| 63 | 37 | 57 | 53 | 75 | L | 127 | 50 |
| 78 | 147 | 117 | 161 | 135 | L | 1194 | 48 |
| 79 | 62 | 71 | 95 | 128 | L | 320 | 213 |
| 80 | 68 | 57 | 53 | 90 | L | 124 | 143 |
| 82 | 40 | 113 | 128 | 97 | L | 143 | 54 |
| 83 | 50 | 46 | 51 | 60 | L | 377 | 38 |
| 85 | 88 | 57 | 60 | 67 | L | 292 | 49 |

TABLE 10-2

| | | | | | | | |
|---|---|---|---|---|---|---|---|
| 86 | 71 | 54 | 48 | 60 | L | 131 | 41 |
| 87 | 16 | 31 | 20 | 36 | 41 | 20 | 27 |
| ~~88~~ | ~~15~~ | ~~54~~ | ~~36~~ | ~~69~~ | ~~L~~ | ~~81~~ | ~~−70~~ |
| 89 | 41 | 60 | 34 | 68 | L | 75 | 50 |
| 90 | 44 | 83 | 59 | 89 | L | 114 | 55 |
| 91 | 31 | 43 | 34 | 47 | L | 90 | 43 |
| 92 | 24 | 50 | 22 | 31 | L | 43 | 29 |
| 93 | 38 | 64 | 40 | 63 | L | 77 | 66 |
| 94 | 13 | 43 | 30 | 49 | L | 30 | 59 |
| 95 | 65 | 32 | 31 | 48 | L | 103 | 27 |
| 96 | 79 | 65 | 71 | 55 | L | 275 | 40 |
| 98 | 20 | 45 | 62 | 48 | L | 53 | 28 |
| 99 | 82 | 75 | 101 | 51 | L | 193 | 22 |
| 101 | 11.5 | L | L | 46.3 | L | 151.1 | 40.1 |
| 102 | 8.2 | L | L | 42.1 | L | 128.6 | 53.9 |
| 103 | 36 | 45 | 32 | 45 | 52 | 97 | 28 |
| 104 | 34 | 32 | 23 | 43 | L | 87 | 28 |
| 105 | 116 | 68 | 52 | 60 | L | 241 | 44 |
| 106 | 18 | 44 | 25 | 38 | L | 41 | 34 |
| 108 | 80 | 55 | 35 | 74 | L | 59 | 64 |
| 109 | 29 | 42 | 37 | 55 | L | 141 | 41 |
| 111 | 18 | 45 | 30 | 42 | L | 56 | 38 |
| 112 | 12 | 34 | 20 | 37 | L | 48 | 26 |
| 113 | 96 | 76 | 71 | 74 | L | 104 | 35 |
| 114 | 10 | 53 | 23 | 34 | L | 93 | 24 |
| 115 | 24 | 36 | 23 | 33 | L | 197 | 21 |
| 116 | 26 | 45 | 23 | 42 | 50 | 69 | 22 |
| 117 | 124 | 72 | 82 | 68 | 45 | 197 | 64 |
| 118 | 59 | 44 | 22 | 38 | L | 105 | 21 |

L indicates that the value of measurement is below the detection limit.

Working Example 5

Measurement of Cytotoxic Activity in Mouse NK Cells

Administration of the Compound

A variety of oligo nucleic acid (20 μg/body) were administered once intraperitoneally to C57BL/6J mouse (purchased from Charles River Japan, Inc.) The blood was sampled before the administration, 1 hour after the administration, 4 hours after the administration and at autopsy (about 24 hours after the administration). These samples were used for the measurement of cytokine in serum.

Measurement of Cytotoxic Activity of Natural Killer (NK) Cell

Isolation of Mouse Spleen Cells

A spleen was obtained from 8-week-old C57BL/6J mouse (purchased from Charles River Japan, Inc.). Then, this spleen was used for isolation of spleen cells. The spleen was ground using a needle in a sterile PBS. The cell suspension was passed through a cell strainer of 70 μm and the filtrate was centrifuged. In order to remove the red blood cells, a red blood cell lysis solution was added to the cells. The cells was washed with PBS. The resulting cells was used for the measurement as mouse spleen cells.

Measurement of Cytotoxic Activity

In cytotoxic activity measurement, using the mouse spleen cells was used as effector cells. In addition, the YAC-1 I was used as target cells. The target cell was stained with calcein. Then, the fluorescence intensity of calcein released from target cells that have been injured by the effector cells was measuring. The value indicating the cytotoxic activity was calculated using the following equation.

Cytotoxic activity (%)=(Test−Background−Spontaneous)/(Maximum Rerease−Background−Spontaneous).

Staining of Target Cells with Calcein-AM $1.5 \times 10^6$ cells of target cells were suspended in 2.5 mL of growth medium: RPMI+RPMI+100 IU/ml penicillin+100 μg/ml streptomycin. 25 μl of 1 mg/ml Calcein-AM solution was added to the cell suspension. The cell suspension was mixed 2-3 times with invert. The cell suspension was incubated twice at 5% $CO_2$ incubator for 15 minutes. After incubation, the cell suspension were centrifuged (1100 rpm, 5 min) and the supernatant was removed. The precipitated cells were suspended in the growth medium at a concentration of $2 \times 10^5$ cells/ml. The resulting cell suspension was used as the target cell solution.

Preparation of the Effector Cells

The isolated mouse spleen cells were suspended in the growth medium at a concentration of $1 \times 10^7$ cells/ml. The resulting cell suspension was used as the effector cell solution.

Procedure of Seeding of Cells

The target cell and the effector cell were seeded in 96 well U bottom plate. The composition of the medium and the ratio of the target cell solution and the effector cell solution was shown below. The plate was incubated at 5% $CO_2$ incubator for 4 hours. Then, the fluorescence intensity of the culture supernatant was measured.

TABLE 11

Composition of the medium

| Composition | Background | Spontaneous | Maximum Release | Test (E:T = 100:1) |
|---|---|---|---|---|
| Growth medium (μL) | 150 | 100 | 50 | — |
| 0.1% Triton solution (μL) | — | — | 50 | — |
| Target cell (μL) | — | 50 | 50 | 50 |
| Effector cell (μL) | — | — | — | 100 |

Background: fluorescence intensity of growth medium itself.

Spontaneous: calcein fluorescence intensity target cells to release naturally.

Maximum Release: calcein fluorescence intensity is released when the target cells were injured with Triton Test: calcein fluorescence intensity target cells are being injured released by effector cells.

Result

The result was shown in FIG. 1. FIG. 1 is a diagram showing the activity of NK cells. FIG. 1 showed the result in groups administrated compound 56, compound 57, compound 82, compound 101 or compound 109, and the result in non-administration group, respectively from left. In the group administrated Sp form stereoisomer of the compounds 56, 57, 82, 103 or 109, the activity of NK cells were enhanced compared to that of the non-administration group (Naive) (FIG. 1).

Working Example 6

The effect on tumor growth in mouse tumor-bearing model

Experimental Procedure

Preparation of Tumor-Bearing Model Mouse and Administration of the Compound

In order to prepare the tumor-bearing mouse, the $3\times10^6$ cells of FM3A cells were inoculated subcutaneously into 7 week old C3H/He mouse. The tumor volume was measured 14 days after the cell inoculation. Administration solution of the compounds of the present invention (30 μg/individual) or saline (control group) were administered within the tumor.

Measurement of Tumor Volume

Using an electronic caliper once, the diameter of the tumor was measured once −11, −7, −4, −1, 0, 2, 4, 7, 9, 11, 14, 16, 18, 21, 23, 25, 28 and 29 days after the administration of the compound. The tumor volume was calculated according to the following formula.

Tumor volume ($mm^3$)=major axis (mm)×[short diameter (mm)]$^2$/2

Result

Figure 2:
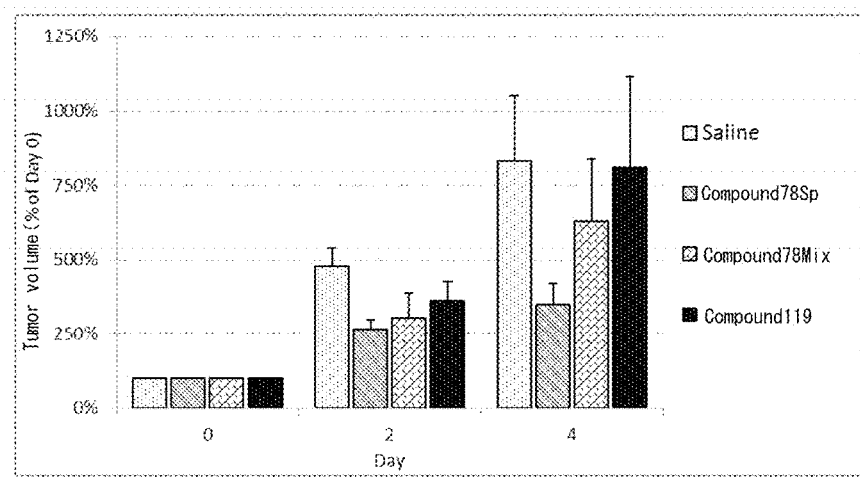
FIG. 2 is a graph showing tumor volume.

The result was shown in FIG. 2. FIG. 2 is a diagram showing the tumor volume. FIG. 2 showed the result in groups administrated saline, compound 78 (S form), Sp form and Rp form mixture and compound 119, respectively from left. Sp form and Rp form mixture is the compound which has the same sequence as compound 78 and that some of Sp type stereoisomer in compound 78 is replaced with Rp type stereoisomer. Compound 119 was used as a reference compound. In the group administrated compound 78, the tumor volume was reduced compared to that in the groups administrated saline or the reference compound. Further, considering the effect of the stereoisomers in the compound 78, Sp stereoisomer showed significant tumor growth inhibitory effect than Sp form and Rp form mixture (Mix).

Working Example 7

The effect on tumor growth in mouse tumor-bearing model

Experimental Procedure

Preparation of Tumor-Bearing Model Mouse and Administration of the Compound

In order to prepare the tumor-bearing mouse, the $2\times10^6$ cells of B15F10 cells and the solution which comprises the compounds (Compound 78) of the present invention (30 μg/individual) were inoculated into 6 week old C57BL/6J mouse. To the control group, saline or the solution which comprises positive control nucleotide (Compound 119) (30 μg/individual) were inoculated.

Measurement of Tumor Volume

Using an electronic caliper once, the diameter of the tumor was measured once 7, 9, 11, 14, 16, 18, 21, 23, 25, 28, 30, 32 and 34 days after the administration of the compound. The tumor volume was calculated according to the following formula.

Tumor volume ($mm^3$)=major axis (mm)×[short diameter (mm)]$^2$/2

The Calculation of the Survival Rate

From the initial administration date (day 0) to the autopsy day (day 34), feed and general conditions were observed. In analyzing the condition, when the tumor diameter was measured to exceed 20 mm (4000 $mm^3$ as tumor volume) in measuring the tumor volume, the animal was asserted to be dying. Then the animal was to be autopsied and was treated as death. Survival rate was calculated according to the following calculation equation.

Survival rate (%)=deaths (animals)/survivors (animals)×100

Result

Figure 3:
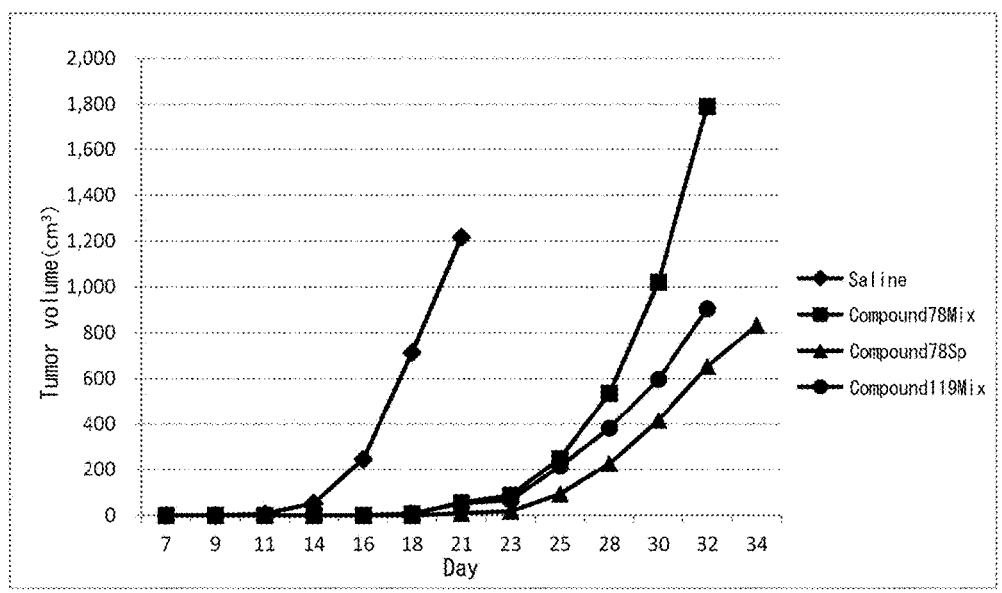
FIG. 3 is a graph showing the growth rate of tumors in tumor-bearing mice that have been administered various compounds.

In the compound 78 group, the growth rate of the tumor was significantly reduced compared to saline group. Further, when compared the effect of stereoisomer by means of the compound 78, the Sp stereoisomer showed clear tumor growth inhibition effect compared to the mixture (Mix) or the positive control nucleotide (Compound 119) (See FIG. 3).

Figure 4:
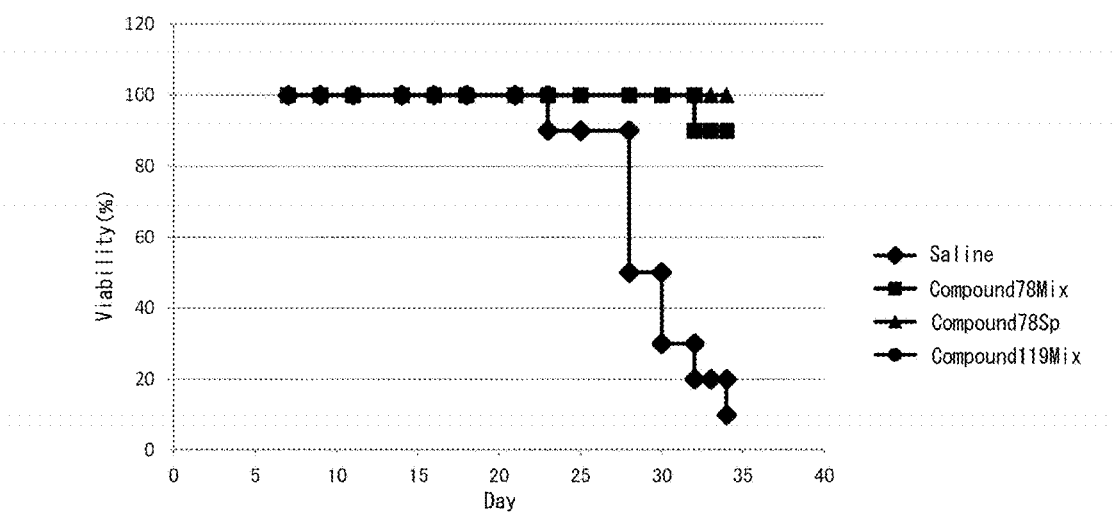
FIG. 4 is a graph showing the survival rate of tumor-bearing mice that have been administered various compounds.

Regarding survival rate, the compound of the present invention group (Compound 78 and Sp type stereoisomer of compound 78) and positive comparison nucleotide (Compound 119) group have remarkable high survival rate compared to saline group. When investigating effect of stereoisomer by means of compound 78, Sp stereoisomer group has remarkably high survive rate compared to mixture group (Mix) (FIG. 4).

INDUSTRIAL APPLICABILITY

The present invention can be utilized in the field of pharmaceutical industry.

The invention claimed is:

1. An adjuvant comprising an oligonucleotide which comprises two to four CpG motifs each represented by 5'-$X_1$CpG$X_2$-3' and has a length of 14 to 32 nucleotides,
   wherein each CpG is a non-methylated CpG without a modified phosphate backbone;
   wherein the $X_1$ is A;
   wherein the $X_2$ is T;
   wherein the 3' end side of at least two CpG motifs are independently connected to a nucleic acid moiety comprising a phosphorothioate linkage,
   wherein linkages at both the 3' end and the 5' end of the oligonucleotide are S type phosphorothioate linkages;
   wherein the oligonucleotide comprises at least one linkage that is not a phosphorothioate linkage outside of the CpG motif; and
   wherein the oligonucleotide comprises a 5'-ACpGTT$^{SP}$T$^{SP}$-3' motif, wherein each SP represents an S type phosphorothioate linkage.

2. An agent which comprises the adjuvant of claim 1.

3. A method for treating a tumor, comprising administering to a subject suffering therefrom an adjuvant comprising an oligonucleotide which comprises two to four CpG motifs each represented by 5'-$X_1$CpG$X_2$-3' and has a length of 14 to 32 nucleotides,
   wherein each CpG is a non-methylated CpG without a modified phosphate backbone;
   wherein the $X_1$ is A;
   wherein the $X_2$ is T;
   wherein the 3' end side of at least two CpG motifs are independently connected to a nucleic acid moiety comprising a phosphorothioate linkage,
   wherein linkages at both the 3' end and the 5' end of the oligonucleotide are S type phosphorothioate linkages;
   wherein the oligonucleotide comprises at least one linkage that is not a phosphorothioate linkage outside of the CpG motif; and
   wherein the oligonucleotide comprises a 5'-ACpGTT$^{SP}$T$^{SP}$-3' motif, wherein each SP represents an S type phosphorothioate linkage.

4. A method for treating a tumor, comprising administering to a subject suffering therefrom an agent of claim 2.

* * * * *